(12) United States Patent
Kumamoto et al.

(10) Patent No.: US 8,216,974 B2
(45) Date of Patent: Jul. 10, 2012

(54) FLUORINE-CONTAINING ORGANOSULFUR COMPOUND AND PESTICIDAL COMPOSITION COMPRISING THE SAME

(75) Inventors: Koji Kumamoto, Toyonaka (JP); Hiroyuki Miyazaki, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 360 days.

(21) Appl. No.: 12/670,376

(22) PCT Filed: Jul. 25, 2008

(86) PCT No.: PCT/JP2008/063819
§ 371 (c)(1),
(2), (4) Date: Jan. 22, 2010

(87) PCT Pub. No.: WO2009/014268
PCT Pub. Date: Jan. 29, 2009

(65) Prior Publication Data
US 2010/0197794 A1 Aug. 5, 2010

(30) Foreign Application Priority Data
Jul. 26, 2007 (JP) .................................. 2007-194295

(51) Int. Cl.
*A01N 37/18* (2006.01)
*A01N 41/10* (2006.01)
*A01P 7/00* (2006.01)
*C07C 233/08* (2006.01)

(52) U.S. Cl. ............ 504/110; 564/162; 568/27; 568/28; 568/38; 568/41; 568/75; 568/77; 568/308; 568/425

(58) Field of Classification Search .................. 504/110; 564/162; 568/27, 28, 38, 41, 75, 77, 308, 568/425
See application file for complete search history.

(56) References Cited

FOREIGN PATENT DOCUMENTS
JP 2005-179321 A 7/2005

OTHER PUBLICATIONS

International Searching Authority (Form PCT/IB/373) and Written Opinion of the International Searching Authority (Form PCT/ISA/237) issued on Jan. 26, 2010 in PCT/JP2008/063819.
Database WPI Week 200560, Thomson Scientific, London, GB; AN, 2005-585455, XP002493506, pp. 1-8.

*Primary Examiner* — Sreeni Padmanabhan
*Assistant Examiner* — Sahar Javanmard
(74) *Attorney, Agent, or Firm* — Birch, Stewart, Kolasch & Birch, LLP

(57) ABSTRACT

There is provided a fluorine-containing organosulfur compound having an excellent controlling effect on arthropod pests represented by the formula (I): wherein G represents an oxygen atom or a sulfur atom; $R^2$ represents a C1-C4 chain hydrocarbon group which is optionally substituted with a halogen atom, etc.; $R^3$ and $R^4$ independently represent a C1-C4 chain hydrocarbon group or a hydrogen atom; $R^5$ represents a C1-C5 haloalkyl group containing at least one fluorine atom, or a fluorine atom; $R^6$ represents a halogen atom, a cyano group, a nitro group or a $-(G^1)q-R^8$ group; $R^7$ represents an amino group etc.; $R^8$ represents a C1-C4 chain hydrocarbon group which is optionally substituted with a halogen atom; m represents an integer of 0 to 5; n represents an integer of 0 to 2; p represents 0 or 1; q represents 0 or 1; and $G^1$ represents an oxygen atom etc.

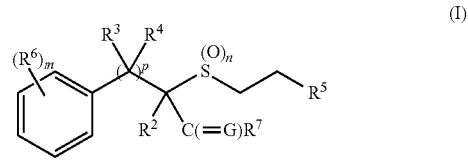

(I)

8 Claims, No Drawings

FLUORINE-CONTAINING ORGANOSULFUR COMPOUND AND PESTICIDAL COMPOSITION COMPRISING THE SAME

TECHNICAL FIELD

The present invention relates to a fluorine-containing organosulfur compound and a pesticidal composition comprising the compound.

BACKGROUND ART

Hitherto, many pesticidal compositions for controlling arthropod pests have been developed and used practically. Further, JP-A 2005-179321 discloses a certain halogen-containing organosulfur compound.

DISCLOSURE OF INVENTION

An object of the present invention is to provide a novel compound having an excellent controlling effect on arthropod pests and its use.

The present inventors have intensively studied to find out a compound having an excellent controlling effect on arthropod pests. As a result, they have found that a fluorine-containing organosulfur compound represented by the following formula (I) has an excellent controlling effect on arthropod pests such as harmful insects or harmful mites. Thus, the present invention has been completed.

That is, the present invention provides:
(1) A fluorine-containing organosulfur compound represented by the formula (I):

$$(R^6)_m \text{—Ar—} C(R^3)(R^4)_p \text{—} C(R^2)(C(=G)R^7) \text{—} S(O)_n \text{—} R^5 \quad (I)$$

wherein G represents an oxygen atom or a sulfur atom;
$R^2$ represents a halogen atom, a hydrogen atom, or a C1-C4 chain hydrocarbon group which is optionally substituted with a halogen atom;
$R^3$ and $R^4$ independently represent a C1-C4 chain hydrocarbon group or a hydrogen atom;
$R^5$ represents a fluorine atom, or a C1-C5 haloalkyl group containing at least one fluorine atom;
$R^6$ represents a halogen atom, a cyano group, a nitro group, or a -($G^1$)q-$R^8$ group;
$R^7$ represents an amino group, a C1-C4 alkylamino group which is optionally substituted with a halogen atom, a di(C1-C4 alkyl)amino group which is optionally substituted with a halogen atom, or a C2-C5 cyclic amino group;
$R^8$ represents a C1-C4 chain hydrocarbon group which is optionally substituted with a halogen atom;
m represents an integer of 0 to 5, provided that $R^6$'s are optionally the same as or different from each other when m is from 2 to 5;
n represents an integer of 0 to 2;
p represents 0 or 1;
q represents 0 or 1; and
$G^1$ represents an oxygen atom, a sulfur atom, a —SO— group, or —SO$_2$— group (hereinafter, referred to as "the compound of the present invention");

(2) The fluorine-containing organosulfur compound according to the above (1), wherein p is 0;
(3) The fluorine-containing organosulfur compound according to the above (1) or (2), wherein G is an oxygen atom;
(4) The fluorine-containing organosulfur compound according to the above (1) or (2), wherein G is an oxygen atom and $R^7$ is an amino group;
(5) The fluorine-containing organosulfur compound according to any one of the above (1) to (4), wherein $R^2$ is a halogen atom;
(6) The fluorine-containing organosulfur compound according to any one of the above (1) to (5), wherein n is 2;
(7) A pesticidal composition comprising the fluorine-containing organosulfur compound according to any one of the above (1) to (6) as an active ingredient; and
(8) A method of controlling an arthropod pest which comprises applying an effective amount of the fluorine-containing organosulfur compound according to any one of the above (1) to (6) to the arthropod pest or a place where the arthropod pest inhabits.

ILLUSTRATIVE EMBODIMENT FOR CARRYING OUT THE INVENTION

The expression "C1-C4" or the like, as used herein, means the total number of carbon atoms constituting each substituent group.

Examples of the "halogen atom" include a fluorine atom, a chlorine atom and a bromine atom.

Examples of the "C1-C4 chain hydrocarbon group which is optionally substituted with a halogen atom" include a C1-C4 alkyl group which is optionally substituted with a halogen atom, such as a methyl group, an ethyl group, a propyl group, a 1-methylethyl group (hereafter, sometimes, referred to as an i-propyl group), a 1,1-dimethylethyl group (hereafter, sometimes, referred to as a t-butyl group), a chloromethyl group, a fluromethyl group, a difluoromethyl group, a trifluoromethyl group, a 2,2,2-trifluoroethyl group, a 1,1,2,2-tetrafluoroethyl group, or a 1,1,2,2,2-pentafluoroethyl group; a C2-C4 alkenyl group which is optionally substituted with a halogen atom, such as a vinyl group, a 2,2-difluorovinyl group, a 1,2,2-trifluorovinyl group, a 1-propenyl group, a 2-propenyl group, a 3,3-difluoro-2-propenyl group, a 1-methyl-2-propenyl group, a 2-methyl-2-propenyl group, a 1-butenyl group, or a 2-butenyl group; and a C2-C4 alkynyl group which is optionally substituted with a halogen atom, such as an ethynyl group, a 1-propynyl group, a 3,3,3-trifluoro-1-propynyl group, a 2-propynyl group, a 1-methyl-2-propynyl group, a 1-butynyl, a 2-butynyl, or a 3-butynyl group.

Examples of the "C1-C4 chain hydrocarbon group" include a C1-C4 alkyl group such as a methyl group, an ethyl group, a propyl group, a 1-methylethyl group (hereafter, sometimes, referred to as an i-propyl group), or a 1,1-dimethylethyl group (hereafter, sometimes, referred to as a t-butyl group); a C2-C4 alkenyl group such as a vinyl group, a 1-propenyl group, a 2-propenyl group, a 1-methyl-2-propenyl group, a 2-methyl-2-propenyl group, a 1-butenyl group or a 2-butenyl group; and a C2-C4 alkynyl group such as an ethynyl group, a 1-propynyl group, a 2-propynyl group, a 1-methyl-2-propynyl group, a 1-butynyl group, a 2-butynyl group or a 3-butynyl group.

Examples of the "C1-C5 haloalkyl group containing at least one fluorine atom" include a fluoromethyl group, a difluoromethyl group, a trifluoromethyl group, a 1-fluoroethyl group, a 2-fluoroethyl group, a 1,1-difluoroethyl group, a 2,2-difluoroethyl group, a 2,2,2-trifluoroethyl group, a 1,1,2,2,2-pentafluoroethyl group, a 1-fluoropropyl group, a 1,1- difluoropropyl group, a 2-fluoropropyl group, a 2,2-difluoropropyl group, a 3-fluoropropyl group, a 3,3-difluoropropyl group, a 3,3,3-trifluoropropyl group, a 1,1,2,2,3,3,3-heptafluoropropyl group, a 2,2,3,3,3-pentafluoropropyl group, a 2,2,2-trifluoro-(1-trifluoromethyl)ethyl group, a 1,2,2,2-tetrafluoro-trifluoro-(1-trifluoromethyl)ethyl group, a 2,2,3,3-tetrafluoropropyl group, a 1-fluorobutyl group, a 1,1-difluorobutyl group, a 2-fluorobutyl group, a 2,2-difluorobutyl group, a 3-fluorobutyl group, a 3,3-difluorobutyl group, a 4-fluorobutyl group, a 4,4-difluorobutyl group, a 4,4,4-trifluorobutyl group, a 3,3,4,4,4-pentafluorobutyl group, a 2,2,3,4,4-pentafluorobutyl group, a 2,2,3,3,4,4,4-heptafluorobutyl group, a 1-fluoropentyl group, a 1,1-difluoropentyl group, a 2-fluoropentyl group, a 2,2-difluoropentyl group, a 3-fluoropentyl group, a 3,3-difluoropentyl group, a 4-fluoropentyl group, a 4,4-difluoropentyl group, a 5-fluoropentyl group, a 5,5-difluoropentyl group, a 5,5,5-trifluoropentyl group, a 4,4,5,5,5-pentafluoropentyl group, a 3,3,4,4,5,5,5-heptafluoropenyl group, a 2,2,3,3,4,4,5,5-octafluoropenyl group, and a 2,2,3,3,4,4,5,5,5-nonafluoropentyl group.

Examples of the "-$(G^1)_q$-$R^8$ group" wherein q is 0 include a methyl group, an ethyl group, a 1-methylethyl group, a 1-ethylethyl group, a 1,1-dimethylethyl group, a propyl group, a 1-methylpropyl group, a butyl group, a fluoromethyl group, a chloromethyl group, a bromomethyl group, a iodomethyl group, a difluoromethyl group, a chlorodifluoromethyl group, a bromodifluoromethyl group, a trifluoromethyl group, a dichloromethyl group, a trichloromethyl group, a 1-chloroethyl group, a 1-bromoethyl group, a 1-fluoroethyl group, a 2-chloroethyl group, a 2-bromoethyl group, a 2-fluoroethyl group, a 2,2-difluoroethyl group, a 2,2,2-trifluoroethyl group, a 2,2,2-trichloroethyl group, a pentafluoroethyl group, a 2,2,2-trifluoro-1-chloroethyl group, a 3-fluoropropyl group, a 3-chloropropyl group, a 1-fluoro-1-methylethyl group, a 1-chloro-1-methylethyl group, a 2-chloro-1,1-dimethylethyl group, a 2-fluoro-1,1-dimethylethyl group, a heptafluoropropyl group, a 1,1,2,2,3,3-hexafluoropropyl group, a 4-chlorobutyl group, a 4-fluorobutyl group, a vinyl group, a 1-methylvinyl group, a 1-propenyl group, a 1-methyl-1-propenyl group, a 2-methyl-1-propenyl group, a 2-propenyl group, a 1-methyl-2-propenyl group, a 2-methyl-2-propenyl group, a 2,2-difluorovinyl group, a 2-chloro-2-propenyl group, a 3,3-dichloro-2-propenyl group, a 2-bromo-2-propenyl group, a 3,3-dibromo-2-propenyl group, a 2-fluoro-2-propenyl group, a 3,3-difluoro-2-propenyl group, an ethynyl group, a 1-propynyl, and a 3,3,3-trifluoro-1-propynyl group.

Examples of the "-$(G^1)_q$-$R^8$ group" wherein q is 1 and $G^1$ is an oxygen atom include a methoxy group, an ethoxy group, a propoxy group, a trifluoromethoxy group, a bromodifluoromethoxy group, a difluoromethoxy group, a chlorodifluoromethoxy group, a pentafluoroethoxy group, a 2,2,2-trifluoroethoxy group, and a 1,1,2,2-tetrafluoroethoxy group.

Examples of the "-$(G^1)_q$-$R^8$ group" wherein q is 1 and $G^1$ is a sulfur atom include a methylthio group, an ethylthio group, a trifluoromethylthio group, a chlorodifluoromethylthio group, a bromodifluoromethylthio group, a dibromofluoromethylthio group, a 2,2,2-trifluoroethylthio group, a 1,1,2,2-tetrafluoroethylthio group, and a pentafluoroethylthio group.

Examples of the "-$(G^1)_q$-$R^8$ group" wherein q is 1 and $G^1$ is a —SO— group include a methylsulfinyl group, an ethylsulfinyl group, and a trifluoromethylsufinyl group.

Examples of the "-$(G^1)_q$-$R^8$ group" wherein q is 1 and $G^1$ is a —$SO_2$— group include a methylsulfonyl group, an ethylsulfonyl group, and a trifluoromethylsufonyl group.

Examples of the "C1-C4 alkylamino group which is optionally substituted with a halogen atom" include an N-methylamino group, an N-ethylamino group, an N-propylamino group, an N-(1-methylethyl)amino group, and an N-(2,2,2-trifluoroethyl)amino group.

Examples of the "di(C1-C4 alkyl)amino group which is optionally substituted with a halogen atom" include an N,N-dimethylamino group, an N-ethyl-N-methylamino group, an N,N-diethylamino group, an N-methyl-N-propylamino group, an N-ethyl-N-propylamino group, an N,N-dipropylamino group, an N-methyl-N-(1-methylethyl)amino group, an N-ethyl-N-(1-methylethyl)amino group, an N,N-di(1-methylethyl)amino group, an N-methyl-N-(2,2,2-trifluoroethyl)amino group, and an N-ethyl-N-(2,2,2-trifluoroethyl)amino group.

Examples of the "C2-C5 cyclic amino group" include a 1-aziridino group, a 1-azetidinyl group, a 1-pyrrolidinyl group, a 1-piperidinyl group, and a 1-morpholinyl group.

Specific examples of the compound of the present invention include:

a fluorine-containing organosulfur compound represented by the formula (I) wherein G is an oxygen atom;

a fluorine-containing organosulfur compound represented by the formula (I) wherein G is an oxygen atom and $R^7$ is a C1-C4 alkylamino group which is optionally substituted with a halogen atom or a di(C1-C4 alkyl)amino group which is optionally substituted with a halogen atom;

a fluorine-containing organosulfur compound represented by the formula (I) wherein G is an oxygen atom and $R^7$ is an amino group;

a fluorine-containing organosulfur compound represented by the formula (I) wherein G is a sulfur atom;

a fluorine-containing organosulfur compound represented by the formula (I) wherein G is a sulfur atom and $R^7$ is a C1-C4 alkylamino group which is optionally substituted with a halogen atom or a di(C1-C4 alkyl)amino group which is optionally substituted with a halogen atom;

a fluorine-containing organosulfur compound represented by the formula (I) wherein G is a sulfur atom and $R^7$ is an amino group;

a fluorine-containing organosulfur compound represented by the formula (I) wherein $R^2$ is a C1-C4 alkyl group which is optionally substituted with a halogen atom, a C2-C4 alkenyl group which is optionally substituted with a halogen atom, a C2-C4 alkynyl group which is optionally substituted with a halogen atom, a halogen atom or a hydrogen atom;

a fluorine-containing organosulfur compound represented by the formula (I) wherein $R^2$ is a hydrogen atom;

a fluorine-containing organosulfur compound represented by the formula (I) wherein $R^2$ is a halogen atom;

a fluorine-containing organosulfur compound represented by the formula (I) wherein $R^2$ is a fluorine or chlorine atom;

a fluorine-containing organosulfur compound represented by the formula (I) wherein $R^2$ is a C1-C4 chain hydrocarbon group which is optionally substituted with a halogen atom;

a fluorine-containing organosulfur compound represented by the formula (I) wherein $R^2$ is a C1-C4 alkyl group which is optionally substituted with a halogen atom;

a fluorine-containing organosulfur compound represented by the formula (I) wherein $R^2$ is a methyl group;

a fluorine-containing organosulfur compound represented by the formula (I) wherein $R^2$ is a C2-C4 alkenyl group which is optionally substituted with a halogen atom;

a fluorine-containing organosulfur compound represented by the formula (I) wherein $R^2$ is a C2-C4 alkynyl group which is optionally substituted with a halogen atom;

a fluorine-containing organosulfur compound represented by the formula (I) wherein $R^3$ and $R^4$ are independently a C1-C4 alkyl group or a hydrogen atom;
a fluorine-containing organosulfur compound represented by the formula (I) wherein $R^3$ and $R^4$ are hydrogen atoms;
a fluorine-containing organosulfur compound represented by the formula (I) wherein $R^3$ and $R^4$ are C1-C4 chain hydrocarbon groups;
a fluorine-containing organosulfur compound represented by the formula (I) wherein $R^3$ and $R^4$ are C1-C4 alkyl groups;
a fluorine-containing organosulfur compound represented by the formula (I) wherein $R^3$ is a C1-C4 alkyl group and $R^4$ is a hydrogen atom;
a fluorine-containing organosulfur compound represented by the formula (I) wherein $R^3$ is a methyl group and $R^4$ is a hydrogen atom;
a fluorine-containing organosulfur compound represented by the formula (I) wherein $R^5$ is a fluorine atom;
a fluorine-containing organosulfur compound represented by the formula (I) wherein $R^5$ is a C1-C5 haloalkyl group containing at least one fluorine atom;
a fluorine-containing organosulfur compound represented by the formula (I) wherein $R^5$ is a fluoromethyl group;
a fluorine-containing organosulfur compound represented by the formula (I) wherein $R^5$ is a trifluoromethyl group;
a fluorine-containing organosulfur compound represented by the formula (I) wherein $R^5$ is a 1,1,2,2,2-pentafluoroethyl group;
a fluorine-containing organosulfur compound represented by the formula (I) wherein $R^5$ is a 1,1,2,2,3,3,3-heptafluoropropyl group;
a fluorine-containing organosulfur compound represented by the formula (I), wherein $R^6$ is a halogen atom, a cyano group, a nitro group, a C1-C4 alkyl group which is optionally substituted with a halogen atom, a C2-C4 alkenyl group which is optionally substituted with a halogen atom, a C2-C4 alkynyl group which is optionally substituted with a halogen atom, a C1-C4 alkoxy group which is optionally substituted with a halogen atom, a C1-C4 alkylthio group which is optionally substituted with a halogen atom, a C1-C4 alkylsulfinyl group which is optionally substituted with a halogen atom, or a C1-C4 alkylsulfonyl group which is optionally substituted with a halogen atom;
a fluorine-containing organosulfur compound represented by the formula (I) wherein p is 0;
a fluorine-containing organosulfur compound represented by the formula (I) wherein p is 1;
a fluorine-containing organosulfur compound represented by the formula (I) wherein m is 1;
a fluorine-containing organosulfur compound represented by the formula (I) wherein m is 1 and $R^6$ is a chlorine atom as a substituent at the 4-position;
a fluorine-containing organosulfur compound represented by the formula (I) wherein m is 1 and $R^6$ is a halogen atom as a substituent at the 4-position;
a fluorine-containing organosulfur compound represented by the formula (I) wherein m is 1 and $R^6$ is a trifluoromethyl group as a substituent at the 4-position;
a fluorine-containing organosulfur compound represented by the formula (I) wherein m is 1 and $R^6$ is an ethynyl group as a substituent at the 4-position;
a fluorine-containing organosulfur compound represented by the formula (I) wherein m is 1 and $R^6$ is a nitro group as a substituent at the 4-position;
a fluorine-containing organosulfur compound represented by the formula (I) wherein m is 1 and $R^6$ is a cyano group as a substituent at the 4-position;
a fluorine-containing organosulfur compound represented by the formula (I) wherein m is 2;
a fluorine-containing organosulfur compound represented by the formula (I) wherein m is 2 and one of $R^6$'s is a halogen atom as a substituent at the 4-position;
a fluorine-containing organosulfur compound represented by the formula (I) wherein m is 3;
a fluorine-containing organosulfur compound represented by the formula (I) wherein m is 3 and one of $R^6$'s is a halogen atom as a substituent at the 4-position;
a fluorine-containing organosulfur compound represented by the formula (I) wherein m is 3 and all of $R^6$'s are halogen atoms;
a fluorine-containing organosulfur compound represented by the formula (I) wherein m is 4;
a fluorine-containing organosulfur compound represented by the formula (I) wherein m is 5;
a fluorine-containing organosulfur compound represented by the formula (I) wherein n is 0;
a fluorine-containing organosulfur compound represented by the formula (I) wherein n is 1;
a fluorine-containing organosulfur compound represented by the formula (I) wherein n is 2;
a fluorine-containing organosulfur compound represented by the formula (I) wherein G is an oxygen atom, $R^7$ is an amino group and $R^2$ is a hydrogen atom;
a fluorine-containing organosulfur compound represented by the formula (I) wherein G is an oxygen atom, $R^7$ is an amino group and $R^2$ is a methyl group;
a fluorine-containing organosulfur compound represented by the formula (I) wherein G is an oxygen atom, $R^7$ is an amino group and $R^2$ is a halogen atom;
a fluorine-containing organosulfur compound represented by the formula (I) wherein G is an oxygen atom, $R^7$ is an amino group, and $R^2$ is a fluorine or chlorine atom;
a fluorine-containing organosulfur compound represented by the formula (I) wherein G is a sulfur atom, $R^7$ is an amino group and $R^2$ is a hydrogen atom;
a fluorine-containing organosulfur compound represented by the formula (I) wherein G is a sulfur atom, $R^7$ is an amino group and $R^2$ is a methyl group;
a fluorine-containing organosulfur compound represented by the formula (I) wherein G is a sulfur atom, $R^7$ is an amino group and $R^2$ is a halogen atom;
a fluorine-containing organosulfur compound represented by the formula (I) wherein G is a sulfur atom, $R^7$ is an amino group, and $R^2$ is a fluorine or chlorine atom;
a fluorine-containing organosulfur compound represented by the formula (I) wherein p is 0, G is an oxygen atom, $R^7$ is an amino group, and $R^2$ is a hydrogen atom;
a fluorine-containing organosulfur compound represented by the formula (I) wherein p is 0, G is an oxygen atom, $R^7$ is an amino group, and $R^2$ is a methyl group;
a fluorine-containing organosulfur compound represented by the formula (I) wherein p is 0, G is an oxygen atom, $R^7$ is an amino group, and $R^2$ is a halogen atom;
a fluorine-containing organosulfur compound represented by the formula (I) wherein p is 0, G is an oxygen atom, $R^7$ is an amino group, and $R^2$ is a fluorine or chlorine atom;
a fluorine-containing organosulfur compound represented by the formula (I) wherein p is 0, G is a sulfur atom, $R^7$ is an amino group, and $R^2$ is a hydrogen atom;
a fluorine-containing organosulfur compound represented by the formula (I) wherein p is 0, G is a sulfur atom, $R^7$ is an amino group, and $R^2$ is a methyl group;

a fluorine-containing organosulfur compound represented by the formula (I) wherein p is 0, G is a sulfur atom, $R^7$ is an amino group, and $R^2$ is a halogen atom; and a fluorine-containing organosulfur compound represented by the formula (I) wherein p is 0, G is a sulfur atom, $R^7$ is an amino group, and $R^2$ is a fluorine or chlorine atom.

Further, the present invention provides an intermediate compound for producing the compound of the present invention (hereafter, referred to as the intermediate compound of the present invention) which is useful in a process for producing the compound of the present invention as described later by a method described hereinafter, and which is represented by the formula (II):

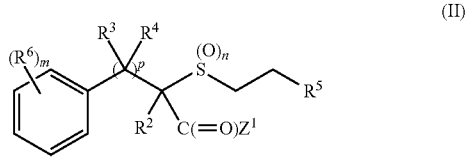

wherein, $Z^1$ represents a halogen atom, hydroxyl group or a C1-C5 alkoxy group;

$R^2$ represents a C1-C4 chain hydrocarbon group which is optionally substituted with a halogen atom, a halogen atom or a hydrogen atom;

$R^3$ and $R^4$ independently represent a C1-C4 chain hydrocarbon group or a hydrogen atom;

$R^5$ represents a C1-C5 haloalkyl group containing at least one fluorine atom, or a fluorine atom;

$R^6$ represents a halogen atom, a cyano group, a nitro group or a $-(G^1)_q-R^8$ group;

$R^8$ represents a C1-C4 chain hydrocarbon atom which is optionally substituted with a halogen atom;

m represents an integer of 0 to 5, provided that $R^6$'s are optionally the same as or different from each other when m is 2 to 5;

n represents an integer of 0 to 2;

p represents 0 or 1;

q represents 0 or 1; and $G^1$ represents an oxygen atom, a sulfur atom, a —SO— group or a —SO$_2$— group.

Specific examples of the intermediate compound of the present invention include:

a compound represented by the formula (II) wherein $Z^1$ is a halogen atom;

a compound represented by the formula (II) wherein $Z^1$ is a hydroxyl group;

a compound represented by the formula (II) wherein $Z^1$ is a C1-C5 alkoxy group;

a compound represented by the formula (II) wherein $Z^1$ is a methoxy group;

a compound represented by the formula (II) wherein $R^2$ is a hydrogen atom;

a compound represented by the formula (II) wherein $R^2$ is a halogen atom;

a compound represented by the formula (II) wherein $R^2$ is a fluorine or chlorine atom;

a compound represented by the formula (II) wherein $R^2$ is a C1-C4 chain hydrocarbon group which is optionally substituted with a halogen atom;

a compound represented by the formula (II) wherein $R^2$ is a C1-C4 alkyl group which is optionally substituted with a halogen atom;

a compound represented by the formula (II) wherein $R^2$ is a methyl group;

a compound represented by the formula (II) wherein $R^2$ is a C2-C4 alkenyl group which is optionally substituted with a halogen atom;

a compound represented by the formula (II) wherein $R^2$ is a C2-C4 alkynyl group which is optionally substituted with a halogen atom;

a compound represented by the formula (II) wherein $R^3$ and $R^4$ are hydrogen atoms;

a compound represented by the formula (II) wherein $R^3$ and $R^4$ are C1-C4 chain hydrocarbon groups;

a compound represented by the formula (II) wherein $R^3$ and $R^4$ are C1-C4 alkyl groups;

a compound represented by the formula (II) wherein $R^3$ is an alkyl group, and $R^4$ is a hydrogen atom;

a compound represented by the formula (II) wherein $R^3$ is a methyl group, and $R^4$ is a hydrogen atom;

a compound represented by the formula (II) wherein $R^5$ is a fluorine atom;

a compound represented by the formula (II) wherein $R^5$ is a C1-C5 haloalkoxy group containing at least one fluorine atom;

a compound represented by the formula (II) wherein $R^5$ is a fluoromethyl group;

a compound represented by the formula (II) wherein $R^5$ is a trifluoromethyl group;

a compound represented by the formula (II) wherein $R^5$ is a 1,1,2,2,2-pentafluoroethyl group;

a compound represented by the formula (II) wherein $R^5$ is a 1,1,2,2,3,3,3-heptafluoropropyl group;

a compound represented by the formula (II) wherein p is 0;

a compound represented by the formula (II) wherein p is 1;

a compound represented by the formula (II) wherein m is 1;

a compound represented by the formula (II) wherein m is 1, and $R^6$ is a chlorine atom as a substituent at the 4-position;

a compound represented by the formula (II) wherein m is 1, and $R^6$ is a halogen atom as a substituent at the 4-position;

a compound represented by the formula (II) wherein m is 1, and $R^6$ is a trifluoromethyl group as a substituent at the 4-position;

a compound represented by the formula (II) wherein m is 1, and $R^6$ is an ethynyl group as a substituent at the 4-position;

a compound represented by the formula (II) wherein m is 1, and $R^6$ is a nitro group as a substituent at the 4-position;

a compound represented by the formula (II) wherein m is 1, and $R^6$ is a cyano group as a substituent at the 4-position;

a compound represented by the formula (II) wherein m is 2;

a compound represented by the formula (II) wherein m is 2, and one of $R^6$'s is a halogen atom as a substituent at the 4-position;

a compound represented by the formula (II) wherein m is 3;

a compound represented by the formula (II) wherein m is 3, and one of $R^6$+s is a halogen atom as a substituent at the 4-position;

a compound represented by the formula (II) wherein m is 3, and all $R^6$'s are halogen atoms;

a compound represented by the formula (II) wherein m is 4;

a compound represented by the formula (II) wherein m is 5;

a compound represented by the formula (II) wherein n is 0;

a compound represented by the formula (II) wherein n is 1; and a compound represented by the formula (II) wherein n is 2.

Then, processes for producing the compound of the present compound are explained.

Production Process 1

A compound represented by the formula (I-2) (hereinafter, referred to as the compound (I-2)), which is the compound of the present invention wherein $R^2$ is a C1-C4 chain hydrocarbon group which is optionally substituted with a halogen atom, can be produced by reacting a compound represented by the formula (I-1) (hereinafter, referred to as the compound (I-1)) with a compound represented by the formula (a) (hereinafter, referred to as the compound (a)) as shown below:

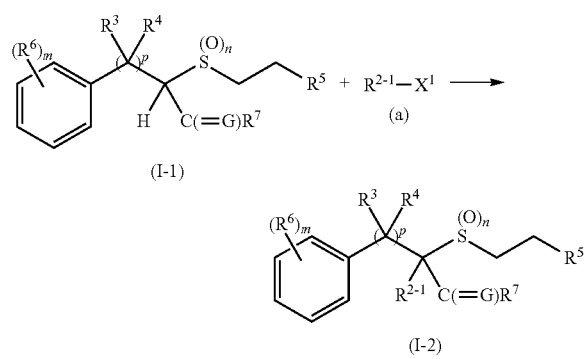

wherein $R^3$, $R^4$, $R^5$, $R^6$, $R^7$, G, p, m and n are as defined above, $R^{2-1}$ represents a C1-C4 alkyl group, a C2-C4 alkenyl group which is optionally substituted with a halogen atom, or a C2-C4 alkynyl group which is optionally substituted with a halogen atom, and $X^1$ represents a leaving group such as a chlorine atom, a bromine atom, an iodine atom, a methanesulfonyl group, a p-toluenesulfonyl group or a trifluoromethanesulfonyl group.

The reaction is usually carried out in the presence of a base in a solvent.

Examples of the solvent used in the reaction include ethers such as diethyl ether, tetrahydrofuran or dimethoxyethane, acid amides such as N,N-dimethylformamide, organic sulfurs such as dimethyl sulfoxide or sulfolane, aliphatic hydrocarbons such as hexane or heptane, aromatic hydrocarbons such as toluene or xylene, halogenated hydrocarbons such as 1,2-dichloroethane or chlorobenzene, water, and a mixture thereof.

Examples of the base used in the reaction include inorganic bases such as sodium hydride, sodium hydroxide, potassium hydroxide or potassium carbonate, alkali metal alkoxides such as sodium methoxide or potassium tert-butoxide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (I-1).

The amount of the compound (a) used in the reaction is usually 1 to 10 mol per 1 mol of the compound (I-1).

The reaction temperature is usually in a range of −50 to 100° C., and the reaction time is usually 1 to 24 hours.

After completion of the reaction, the compound (I-2) can be isolated, for example, by pouring a reaction mixture into water and extracting the resulting mixture with an organic solvent, followed by concentration. The isolated compound (I-2) can be further purified by chromatography, recrystallization or the like, if necessary.

Production Process 2

A compound represented by the formula (I-3) (hereinafter, referred to as the compound (I-3)), which is the compound of the present invention wherein $R^2$ is a halogen atom, can be produced by reacting the compound (I-1) with a halogenating agent (b) in the presence of a base as shown below:

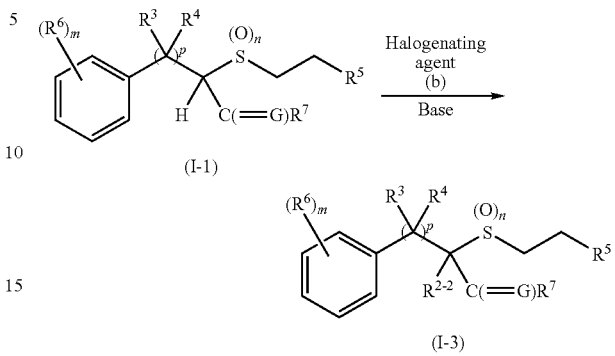

wherein $R^3$, $R^4$, $R^5$, $R^6$, $R^7$, G, p, m and n are as defined above, and $R^{2-2}$ represents a halogen atom.

The reaction is usually carried out in the presence of a base in a solvent.

Examples of the solvent used in the reaction include ethers such as diethyl ether, tetrahydrofuran or dimethoxyethane, acid amides such as N,N-dimethylformamide, organic sulfurs such as dimethyl sulfoxide or sulfolane, aliphatic hydrocarbons such as hexane or heptane, aromatic hydrocarbons such as toluene or xylene, halogenated hydrocarbons such as 1,2-dichloroethane or chlorobenzene, water, and a mixture thereof.

Examples of the base used in the reaction include inorganic bases such as sodium hydride, sodium hydroxide, potassium hydroxide or potassium carbonate, alkali metal alkoxides such as sodium methoxide or potassium tert-butoxide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (I-1).

Examples of the halogenating agent (b) used in the reaction include halogenated hydrocarbons such as carbon tetrachloride or hexachloroethane, halogens such as fluorine, chlorine, bromine or iodine, N-halogenated succinimide such as N-chlorosuccinimide, N-bromosuccinimide or N-iodosuccinimide, N-fluoropyridinium salts such as 1-fluoro-2,4,6-trimethylpyrridinium trifluoromethane sulfonate or 1,1'-difluoro-2,2'-bipyridinium bistetrafluoroborate, and inorganic salts such as copper (II) chloride or copper (II) bromide.

The amount of the halogenating agent (b) used in the reaction is usually 1 to 10 mol per 1 mol of the compound (I-1).

The reaction temperature is usually in a range of −100 to 100° C., and the reaction time is usually 1 to 24 hours.

After completion of the reaction, the compound (I-3) can be isolated, for example, by pouring a reaction mixture into water and extracting the resulting mixture with an organic solvent, followed by concentration. The isolated compound (I-3) can be further purified by chromatography, recrystallization or the like, if necessary.

Production Process 3

The compound (I-3)) can be produced by reacting the compound (I-1) with a halogenating agent (c) as shown below:

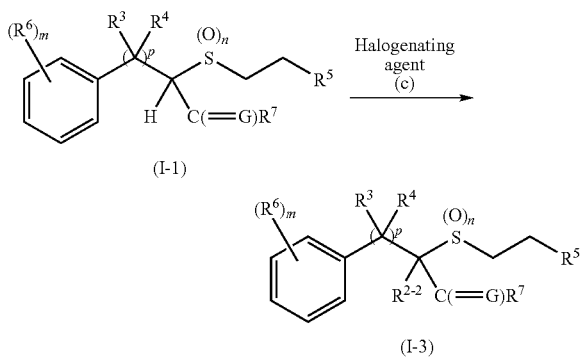

(I-1)

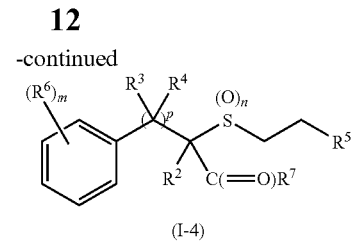

(I-4)

wherein $R^2$, $R^3$, $R^4$, $R^5$, $R^6$, $R^7$, p, m and n are as defined above, and $X^2$ represents a halogen atom.

The reaction is usually carried out in a solvent in the presence of a base.

Examples of the solvent used in the reaction include acid amides such as N,N-dimethylformamide, ethers such as diethyl ether or tetrahydrofuran, organic sulfurs such as dimethyl sulfoxide or sulfolan, halogenated hydrocarbons such as chloroform, dichloromethane, 1,2-dichloroethane or chlorobenzene, aromatic hydrocarbons such as toluene or xylene, water, and a mixture thereof.

Examples of the base used in the reaction include inorganic bases such as sodium hydride, sodium hydroxide, potassium hydroxide or potassium carbonate, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (f).

The amount of the compound (g) used in the reaction is usually 1 to 10 mol per 1 mol of the compound (f).

The reaction temperature is usually in a range of −20 to 100° C., and the reaction time is usually 1 to 24 hours.

After completion of the reaction, the compound (I-4) can be isolated, for example, by pouring a reaction mixture into water and extracting the resulting mixture with an organic solvent, followed by concentration. The isolated compound (I-4) can be further purified by chromatography, recrystallization or the like, if necessary.

Production Process 5

The compound (I-4) can be produced by reacting a compound represented by the formula (d) (hereinafter, referred to as the compound (d)) with the compound (g) as shown below:

(I-3)

wherein $R^3$, $R^4$, $R^5$, $R^6$, $R^7$, $R^{2-2}$, G, p, m and n are as defined above.

The reaction is usually carried out without a solvent or in a solvent.

Examples of the solvent used in the reaction include halogenated hydrocarbons such as chloroform, carbon tetrachloride, 1,2-dichloroethane, dichloromethane or dichlorobenzene, aromatic hydrocarbons such as toluene or xylene, aliphatic nitriles such as acetonitrile or propionitrile, aliphatic carboxylic acids such as acetic acid, carbon disulfide, water, and a mixture thereof.

Examples of the halogenating agent (c) used in the reaction include halogens such as fluorine, chlorine, bromine or iodine, hydrogen halide such as hydrogen fluoride, hydrogen chloride, hydrogen bromide or hydrogen iodide, sulfur halide compounds such as thionyl chloride, thionyl bromide or sulfuryl chloride, and phosphorus halide compounds such as phosphorus trichloride, phosphorus tribromide, phosphorus pentachloride or phosphorus oxychloride.

The amount of the halogenating agent (c) used in the reaction is usually 1 to 10 mol per 1 mol of the compound (I-1).

The reaction temperature is usually in a range of −100 to 200° C., and the reaction time is usually 1 to 24 hours.

After completion of the reaction, the compound (I-3) can be isolated, for example, by pouring a reaction mixture into water and extracting the resulting mixture with an organic solvent, followed by concentration. The isolated compound (I-3) can be further purified by chromatography, recrystallization or the like, if necessary.

Production Process 4

A compound represented by the formula (I-4) (hereinafter, referred to as the compound (I-4)), which is the compound of the present invention wherein G is an oxygen atom, can be produced by reacting a compound represented by the formula (f) (hereinafter, referred to as the compound (f)) with a compound represented by the formula (g) (hereinafter, referred to as the compound (f)) as shown below:

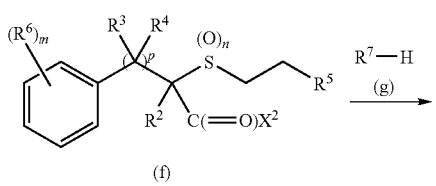

(f)

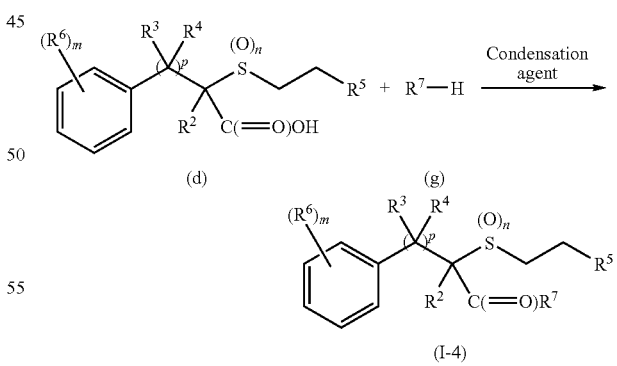

wherein $R^2$, $R^3$, $R^4$, $R^5$, $R^6$, $R^7$, p, m and n are as defined above.

The reaction is usually carried out in the presence of a condensation agent in a solvent.

Examples of the solvent used in the reaction include acid amides such as N,N-dimethylformamide, ethers such as diethyl ether or tetrahydrofuran, organic sulfurs such as dimethyl sulfoxide or sulfolan, halogenated hydrocarbons such as chloroform, dichloromethane, 1,2-dichloroethane or chlorobenzene, and aromatic hydrocarbons such as toluene or xylene.

Examples of the condensation agent used in the reaction include dicyclohexylcarbodiimide, N-(3-dimethylaminopropyl)-N'-ethylcarbodiimide and carbonyldiimidazole.

The amount of the condensation agent used in the reaction is usually 1 to 10 mol per 1 mol of the compound (d).

The amount of the compound (g) used in the reaction is usually 1 to 10 mol per 1 mol of the compound (d).

The reaction temperature is usually in a range of −20 to 100° C., and the reaction time is usually 1 to 24 hours.

After completion of the reaction, the compound (I-4) can be isolated, for example, by pouring a reaction mixture into water and extracting the resulting mixture with an organic solvent, followed by concentration. The isolated compound (I-4) can be further purified by chromatography, recrystallization or the like, if necessary.

Production Process 6

A compound represented by the formula (I-1-1) (hereinafter, referred to as the compound (I-1-1)), which is the compound of the present invention wherein $R^2$ is a hydrogen atom and p is 1, can be produced by reacting a compound represented by the formula (h) (hereinafter, referred to as the compound (h)) with a compound represented by the formula (i) (hereinafter, referred to as the compound (i)) as shown below:

wherein $R^3$, $R^4$, $R^5$, $R^6$, $R^7$, G, $X^1$, m and n are as defined above.

The reaction is usually carried out in the presence of a base in a solvent.

Examples of the solvent used in the reaction include acid amides such as N,N-dimethylformamide, ethers such as diethyl ether or tetrahydrofuran, organic sulfurs such as dimethyl sulfoxide or sulfolan, halogenated hydrocarbons such as chloroform, dichloromethane, 1,2-dichloroethane or chlorobenzene, aromatic hydrocarbons such as toluene or xylene, water, and a mixture thereof.

Examples of the base used in the reaction include inorganic bases such as sodium hydride, sodium hydroxide, potassium hydroxide or potassium carbonate, alkali metal alkoxides such as sodium methoxide or potassium tert-butoxide, alkali metal amides such as lithium diisopropylamide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (i).

The amount of the compound (h) used in the reaction is usually 1 to 10 mol per 1 mol of the compound (i).

The reaction temperature is usually in a range of −100 to 100° C., and the reaction time is usually 1 to 24 hours.

After completion of the reaction, the compound (I-1-1) can be isolated, for example, by pouring a reaction mixture into water and extracting the resulting mixture with an organic solvent, followed by concentration. The isolated compound (I-1-1) can be further purified by chromatography, recrystallization or the like, if necessary.

Production Process 7

The compound (I-4) can be produced by, for example, reacting a compound represented by the formula (q) (hereinafter, referred to as the compound (q)) with the compound (g) as shown below:

wherein $R^2$, $R^3$, $R^4$, $R^5$, $R^6$, $R^7$, p, m and n are as defined above, and $R^9$ represents a C1-C5 alkyl group.

The reaction is usually carried out in a solvent.

Examples of the solvent used in the reaction include acid amides such as N,N-dimethylformamide, ethers such as diethyl ether or tetrahydrofuran, organic sulfurs such as dimethyl sulfoxide or sulfolan, halogenated hydrocarbons such as chloroform, dichloromethane, 1,2-dichloroethane or chlorobenzene, aromatic hydrocarbons such as toluene or xylene, and alcohols such as methanol or ethanol.

The amount of the compound (g) used in the reaction is usually 1 to 10 mol per 1 mol of the compound (q).

The reaction temperature is usually in a range of −20 to 100° C., and the reaction time is usually 1 to 24 hours.

After completion of the reaction, the compound (I-4) can be isolated, for example, by pouring a reaction mixture into water and extracting the resulting mixture with an organic solvent, followed by concentration. The isolated compound (I-4) can be further purified by chromatography, recrystallization or the like, if necessary.

Production Process 8

A compound represented by the formula (I-6) (hereinafter, referred to as the compound (I-6)), which is the compound of the present invention wherein G is a sulfur atom, can be produced by reacting the compound (I-4) with a sulfurizing agent (k) as shown below:

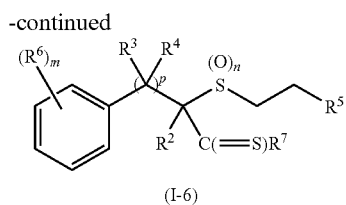

(I-6)

wherein $R^2$, $R^3$, $R^4$, $R^5$, $R^6$, $R^7$, p, m and n are as defined above.

The reaction is usually carried out in a solvent.

Examples of the solvent used in the reaction include halogenated hydrocarbons such as chloroform, dichloromethane, 1,2-dichloroethane or chlorobenzene, and aromatic hydrocarbons such as toluene or xylene.

Examples of the sulfurizing agent (k) used in the reaction include inorganic sulfur compounds such as hydrogen sulfide or diphosphorus pentasulfide, and organosulfur compounds such as 2,4-bis(4-methoxyphenyl)-1,3-dithia-2,4-diphosphetane 2,4-disulfide.

The amount of the sulfurizing agent (k) used in the reaction is usually 0.5 to 10 mol per 1 mol of the compound (I-4).

The reaction temperature is usually in a range of 0 to 250° C., and the reaction time is usually 1 to 72 hours.

After completion of the reaction, the compound (I-6) can be isolated, for example, by pouring a reaction mixture into water and extracting the resulting mixture with an organic solvent, followed by concentration. The isolated compound (I-6) can be further purified by chromatography, recrystallization or the like, if necessary.

Production Process 9

A compound represented by the formula (I-7) (hereinafter, referred to as the compound (I-7)), which is the compound of the present invention wherein n is 0, can be produced by reacting a compound represented by the formula (1) (hereinafter, referred to as the compound (1)) with a compound represented by the formula (m) (hereinafter, referred to as the compound (m)) as shown below:

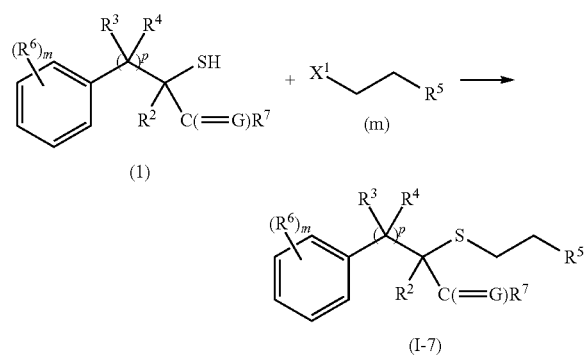

wherein $R^2$, $R^3$, $R^4$, $R^5$, $R^6$, $R^7$, G, $X^1$, p and m are as defined above.

The reaction is usually carried out in the presence of a base in a solvent.

Examples of the solvent used in the reaction include acid amides such as N,N-dimethylformamide, ethers such as diethyl ether or tetrahydrofuran, organic sulfurs such as dimethyl sulfoxide or sulfolane, halogenated hydrocarbons such as chloroform, dichloromethane, 1,2-dichloroethane or chlorobenzene, aromatic hydrocarbons such as toluene or xylene, alcohols such as methanol or ethanol, water, and a mixture thereof.

Examples of the base used in the reaction include inorganic bases such as sodium hydride, potassium hydride, sodium hydroxide, potassium hydroxide or potassium carbonate, alkali metal alkoxides such as sodium methoxide or potassium tert-butoxide, alkali metal amides such as lithium diisopropylamide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (1).

The amount of the compound (m) used in the reaction is usually 1 to 10 mol per 1 mol of the compound (1).

The reaction temperature is usually in a range of −20 to 100° C., and the reaction time is usually 1 to 24 hours.

After completion of the reaction, the compound (I-7) can be isolated, for example, by pouring a reaction mixture into water and extracting the resulting mixture with an organic solvent, followed by concentration. The isolated compound (I-7) can be further purified by chromatography, recrystallization or the like, if necessary.

Production Process 10

The compound (I-7) can be produced by reacting a compound represented by the formula (n) (hereinafter, referred to as the compound (n)) with a compound represented by the formula (o) (hereinafter, referred to as the compound (o)) as shown below:

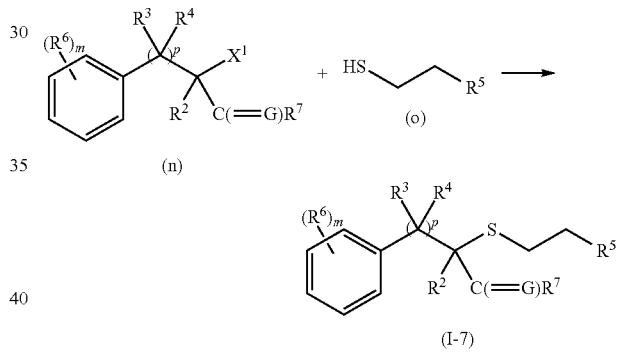

wherein $R^2$, $R^3$, $R^4$, $R^5$, $R^6$, $R^7$, G, $X^1$, p and m are as defined above.

The reaction is usually carried out in the presence of a base in a solvent.

Examples of the solvent used in the reaction include acid amides such as N,N-dimethylformamide, ethers such as diethyl ether or tetrahydrofuran, organic sulfurs such as dimethyl sulfoxide or sulfolane, halogenated hydrocarbons such as chloroform, dichloromethane, 1,2-dichloroethane or chlorobenzene, aromatic hydrocarbons such as toluene or xylene, alcohols such as methanol or ethanol, water, and a mixture thereof.

Examples of the base used in the reaction include inorganic bases such as sodium hydride, potassium hydride, sodium hydroxide, potassium hydroxide or potassium carbonate, alkali metal alkoxides such as sodium methoxide or potassium tert-butoxide, alkali metal amides such as lithium diisopropylamide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (n).

The amount of the compound (o) used in the reaction is usually 1 to 10 mol per 1 mol of the compound (n).

The reaction temperature is usually in a range of −20 to 100° C., and the reaction time is usually 1 to 24 hours.

After completion of the reaction, the compound (I-7) can be isolated, for example, by pouring a reaction mixture into water and extracting the resulting mixture with an organic solvent, followed by concentration. The isolated compound (I-7) can be further purified by chromatography, recrystallization or the like, if necessary.

Production Process 11

A compound represented by the formula (I-8) (hereinafter, referred to as the compound (I-8)), which is the compound of the present invention wherein n is 1 or 2, can be produced by reacting the compound (I-7) with an oxidizing agent (x) as shown below:

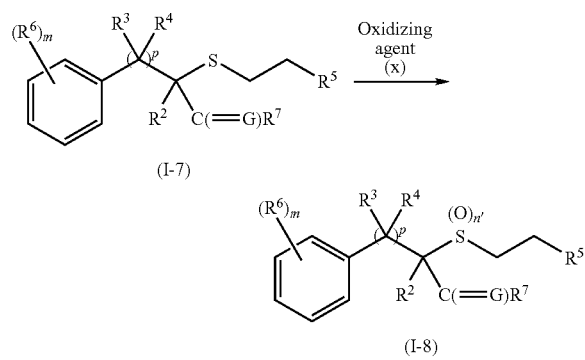

wherein $R^2$, $R^3$, $R^4$, $R^5$, $R^6$, $R^7$, G, p and m are as defined above, and n' represents 1 or 2.

The reaction is usually carried out in a solvent.

Examples of the solvent used in the reaction include halogenated hydrocarbons such as chloroform, dichloromethane, 1,2-dichloroethane or chlorobenzene, aromatic hydrocarbons such as toluene or xylene, aliphatic carboxylic acids such as acetic acid or trifluoroacetic acid, alcohols such as methanol or ethanol, water, and a mixture thereof.

Examples of the oxidizing agent (x) used in the reaction include organic peroxides such as peracetic acid, trifuloroperacetic acid or m-chloroperbenzoic acid, halogens such as chlorine or bromine, halogen-containing imides such as N-chlorosuccinimide, halides such as perchloric acid (or a salt thereof) or periodic acid (or a salt thereof), permanganates such as potassium permanganate, chromates such as potassium chromate, and hydrogen peroxide.

The amount of the oxidizing agent (x) used in the reaction is usually 1 to 10 mol per 1 mol of the compound (I-7).

The reaction temperature is usually in a range of −50 to 200° C., and the reaction time is usually 1 to 72 hours.

After completion of the reaction, the compound (I-8) can be isolated, for example, by pouring a reaction mixture into water and extracting the resulting mixture with an organic solvent, followed by concentration. The isolated compound (I-8) can be further purified by chromatography, recrystallization or the like, if necessary.

Then, reference processes for producing the intermediate compound of the present compound are explained.

Reference Process 1

The compound (d) can be produced by hydrolyzing the compound (q) as shown below:

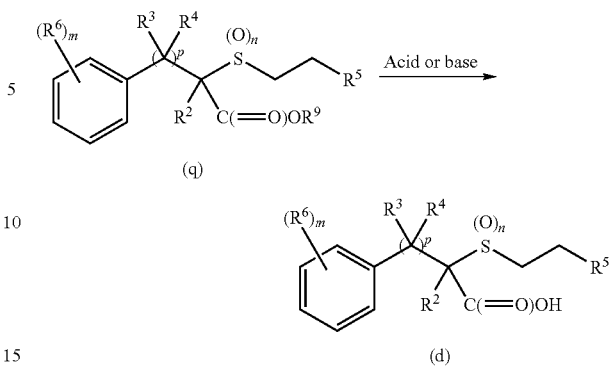

wherein $R^2$, $R^3$, $R^4$, $R^5$, $R^6$, $R^9$, p, m and n are as defined above.

The reaction is usually carried out in an organic solvent in the presence of an acid or a base, and water.

Examples of the solvent used in the reaction include acid amides, ethers such as diethyl ether or tetrahydrofuran, organic sulfurs such as dimethyl sulfoxide or sulfolane, halogenated hydrocarbons such as chloroform, dichloromethane, 1,2-dichloroethane or chlorobenzene, aromatic hydrocarbons such as toluene or xylene, aliphatic hydrocarbons such as acetic acid or formic acid, alcohols such as methanol or ethanol, and a mixture thereof.

Examples of the base used in the reaction include inorganic bases such as sodium hydroxide or potassium hydroxide.

Examples of the acid used in the reaction include inorganic acids such as hydrochloric acid or sulfuric acid.

The amount of the acid or base used in the reaction is usually 1 to 10 mol per 1 mol of the compound (q).

The reaction temperature is usually in a range of −20 to 100° C., and the reaction time is usually 1 to 24 hours.

After completion of the reaction, the compound (d) can be isolated, for example, by extracting a reaction mixture with an organic solvent after, if necessary, adding water and/or an acid to the reaction mixture, followed by concentration. The isolated compound (d) can be further purified by chromatography, recrystallization or the like, if necessary.

Reference Process 2

A compound represented by the formula (q-2) (hereinafter, referred to as the compound (q-2)), which is the compound (q) wherein $R^2$ is a C1-C4 chain hydrocarbon group which is optionally substituted with a halogen atom, can be produced by reacting a compound represented by the formula (q-1) (hereinafter, referred to as the compound (q-1)) which is the compound (q) wherein $R^2$ is a hydrogen atom with the compound (a) as shown below:

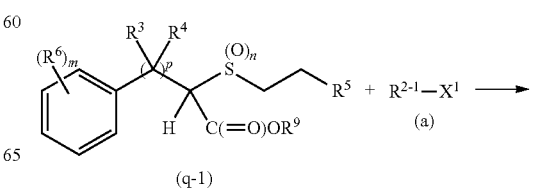

-continued

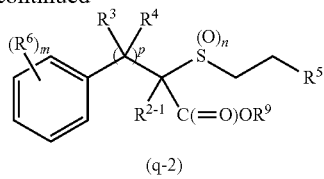

(q-2)

wherein $R^{2-1}$, $R^3$, $R^4$, $R^5$, $R^6$, $R^9$, $X^1$, p, m and n are as defined above.

The reaction is usually carried out in the presence of a base in a solvent.

Examples of the solvent used in the reaction include ethers such as diethyl ether, tetrahydrofuran or dimethoxyethane, acid amides such as N,N-dimethylformamide, organic sulfurs such as dimethyl sulfoxide or sulfolane, aliphatic hydrocarbons such as hexane or heptane, aromatic hydrocarbons such as toluene or xylene, halogenated hydrocarbons such as 1,2-dichloroethane or chlorobenzene, water, and a mixture thereof.

Examples of the base used in the reaction include inorganic bases such as sodium hydride, sodium hydroxide, potassium hydroxide or potassium carbonate, alkali metal alkoxides such as sodium methoxide or potassium tert-butoxide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (q-1).

The amount of the compound (a) used in the reaction is usually 1 to 10 mol per 1 mol of the compound (q-1).

The reaction temperature is usually in a range of −50 to 100° C., and the reaction time is usually 1 to 24 hours.

After completion of the reaction, the compound (q-2) can be isolated, for example, by pouring a reaction mixture into water and extracting the resulting mixture with an organic solvent, followed by concentration. The isolated compound (q-2) can be further purified by chromatography, recrystallization or the like, if necessary.

Reference Process 3

A compound represented by the formula (q-3) (hereinafter, referred to as the compound (q-3)), which is the compound (q) wherein $R^2$ is a halogen atom, can be produced by reacting the compound (q-1) with halogenating agent (b) in the presence of a base as shown below:

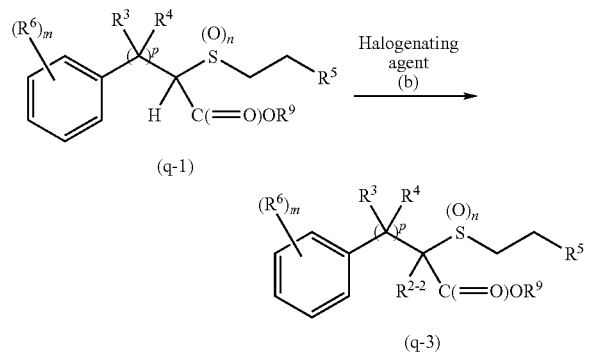

wherein $R^{2-2}$, $R^3$, $R^4$, $R^5$, $R^6$, $R^9$, p, m and n are as defined above.

The reaction is usually carried out in a solvent in the presence of a base.

Examples of the solvent used in the reaction include ethers such as diethyl ether, tetrahydrofuran or dimethoxyethane, acid amides such as N,N-dimethylformamide, organic sulfurs such as dimethyl sulfoxide or sulfolane, aliphatic hydrocarbons such as hexane or heptane, aromatic hydrocarbons such as toluene or xylene, halogenated hydrocarbons such as 1,2-dichloroethane or chlorobenzene, water, and a mixture thereof.

Examples of the base used in the reaction include inorganic bases such as sodium hydride, sodium hydroxide, potassium hydroxide or potassium carbonate, alkali metal alkoxides such as sodium methoxide or potassium tert-butoxide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (q-1).

Examples of the halogenating agent (b) used in the reaction include halogenated hydrocarbons such as carbon tetrachloride or hexachloroethane, halogens such as fluorine, chlorine, bromine or iodine, N-halogenated succinimide such as N-chlorosuccinimide, N-bromosuccinimide or N-iodosuccinimide, N-fluoropyridinium salts such as 1-fluoro-2,4,6-trimethylpyridinium trifluoromethane sulfonate or 1,1'-difluoro-2,2'-bipyridinium bistetrafluoroborate, and inorganic salts such as copper (II) chloride or copper (II) bromide.

The amount of the halogenating agent (b) used in the reaction is usually 1 to 10 mol per 1 mol of the compound (q-1).

The reaction temperature is usually in a range of −100 to 100° C., and the reaction time is usually 1 to 24 hours.

After completion of the reaction, the compound (q-3) can be isolated, for example, by pouring a reaction mixture into water and extracting the resulting mixture with an organic solvent, followed by concentration. The isolated compound (q-3) can be further purified by chromatography, recrystallization or the like, if necessary.

Reference Process 4

The compound (q-3) can be produced by reacting a compound (q-1) with the halogenating agent (c) as shown below:

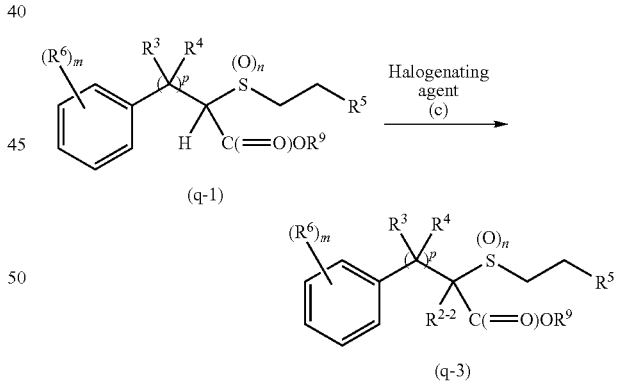

wherein $R^{2-2}$, $R^3$, $R^4$, $R^5$, $R^6$, $R^9$, p, m and n are as defined above.

The reaction is usually carried out with or without a solvent.

Examples of the solvent used in the reaction include halogenated hydrocarbons such as chloroform, carbon tetrachloride, 1,2-dichloroethane or chlorobenzene, aromatic hydrocarbons such as toluene or xylene, aliphatic nitriles such as acetonitrile or propionitrile, aliphatic carboxylic acids such as acetic acid, carbon disulfide, water, and a mixture thereof.

Examples of the halogenating agent (c) used in the reaction include halogens such as fluorine, chlorine, bromine or iodine, hydrogen halide such as hydrogen fluoride, hydrogen chloride, hydrogen bromide or hydrogen iodide, sulfur halide compounds such as thionyl chloride, thionyl bromide or sulfuryl chloride, and phosphorus halide compounds such as phosphorus trichloride, phosphorus tribromide, phosphorus pentachloride or phosphorus oxychloride.

The amount of the halogenating agent (c) used in the reaction is usually 1 to 10 mol per 1 mol of the compound (q-1).

The reaction temperature is usually in a range of −100 to 200° C., and the reaction time is usually 1 to 24 hours.

After completion of the reaction, the compound (q-3) can be isolated, for example, by pouring a reaction mixture into water and extracting the resulting mixture with an organic solvent, followed by concentration. The isolated compound (q-3) can be further purified by chromatography, recrystallization or the like, if necessary.

Reference Process 5

A compound represented by the formula (q-4) (hereinafter, referred to as the compound (q-4)), which is the compound (q) wherein $R^2$ is a C1-C4 chain hydrocarbon group or hydrogen atom and p is 0, can be produced by reacting a compound represented by the formula (r) (hereinafter, referred to as the compound (r)) with a compound represented by the formula (s) (hereinafter, referred to as the compound (s)) as shown below:

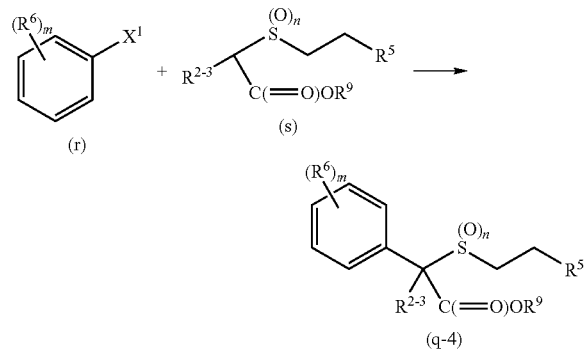

wherein $R^5$, $R^6$, $R^9$, $X^1$, m, n and X are as defined above, and $R^{2-3}$ represents a C1-C4 chain hydrocarbon group or hydrogen atom.

The reaction is usually carried out in an organic solvent in the presence of a base.

Examples of the solvent used in the reaction include acid amides such as N,N-dimethylformamide, ethers such as diethyl ether, 1,4-dioxane or tetrahydrofuran, and organic sulfurs such as dimethyl sulfoxide or sulfolane.

Examples of the base used in the reaction include inorganic bases such as sodium hydride, potassium hydride, sodium hydroxide, potassium hydroxide, potassium carbonate or cesium carbonate, alkali metal alkoxides such as sodium methoxide or potassium tert-butoxide, and alkali metal amides such as lithium diisopropylamide.

The amount of the base used in the reaction is usually 1 to 10 mol per 1 mol of the compound (s).

The amount of the compound (r) used in the reaction is usually 1 to 10 mol per 1 mol of the compound (s).

The reaction temperature is usually in a range of −20 to 200° C., and the reaction time is usually 1 to 24 hours.

After completion of the reaction, the compound (q-4) can be isolated, for example, by pouring a reaction mixture into water and extracting the resulting mixture with an organic solvent, followed by concentration. The isolated compound (q-4) can be further purified by chromatography, recrystallization or the like, if necessary.

Reference Process 6

The compound (q-4) can be produced by reacting the compound (r) with the compound (s) in the presence of a metal catalyst (y) as shown below:

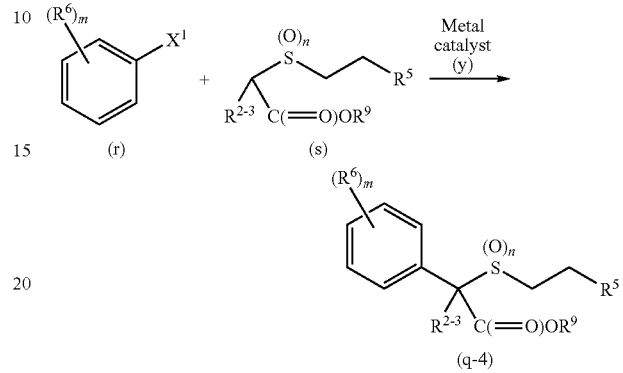

wherein $R^{2-3}$, $R^5$, $R^6$, $R^9$, $X^1$, m and n are as defined above.

The reaction is usually carried out in an organic solvent in the presence of a base and a catalyst.

Examples of the solvent used in the reaction include acid amides such as N,N-dimethylformamide, ethers such as diethyl ether, 1,4-dioxane or tetrahydrofuran, and organic sulfurs such as dimethyl sulfoxide or sulfolane.

Examples of the base used in the reaction include inorganic bases such as sodium hydride, potassium hydride, sodium hydroxide, potassium hydroxide, potassium carbonate or cesium carbonate, alkali metal alkoxides such as sodium methoxide or potassium tert-butoxide, and alkali metal amides such as lithium diisopropylamide.

The amount of the base used in the reaction is usually 1 to 10 mol per 1 mol of the compound (s).

The amount of the compound (r) used in the reaction is usually 1 to 10 mol per 1 mol of the compound (s).

Examples of the metal catalyst (y) used in the reaction include palladium complexes such as tetrakis(triphenylphosphine) palladium(0) or tris(dibenzylideneacetone) dipalladium(0) chloroform complex, and copper(I) halides such as copper(I) bromide or copper(I) iodide.

The amount of the metal catalyst (y) used in the reaction is usually 0.001 to 0.5 mol per 1 mol of the compound (s).

The reaction temperature is usually in a range of −20 to 200° C., and the reaction time is usually 1 to 24 hours.

After completion of the reaction, the compound (q-4) can be isolated, for example, by pouring a reaction mixture into water and extracting the resulting mixture with an organic solvent, followed by concentration. The isolated compound (q-4) can be further purified by chromatography, recrystallization or the like, if necessary.

Reference Process 7

A compound represented by the formula (q-5) (hereinafter, referred to as the compound (q-5)), which is the compound (q) wherein $R^2$ is a C1-C4 chain hydrocarbon group or a hydrogen atom and p is 1, can be produced by reacting the compound (s) with the compound (h) as shown below:

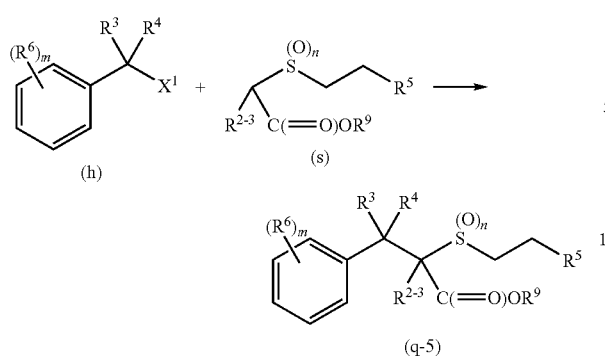

wherein $R^{2-3}$, $R^3$, $R^4$, $R^5$, $R^6$, $R^9$, $X^1$, m and n are as defined above.

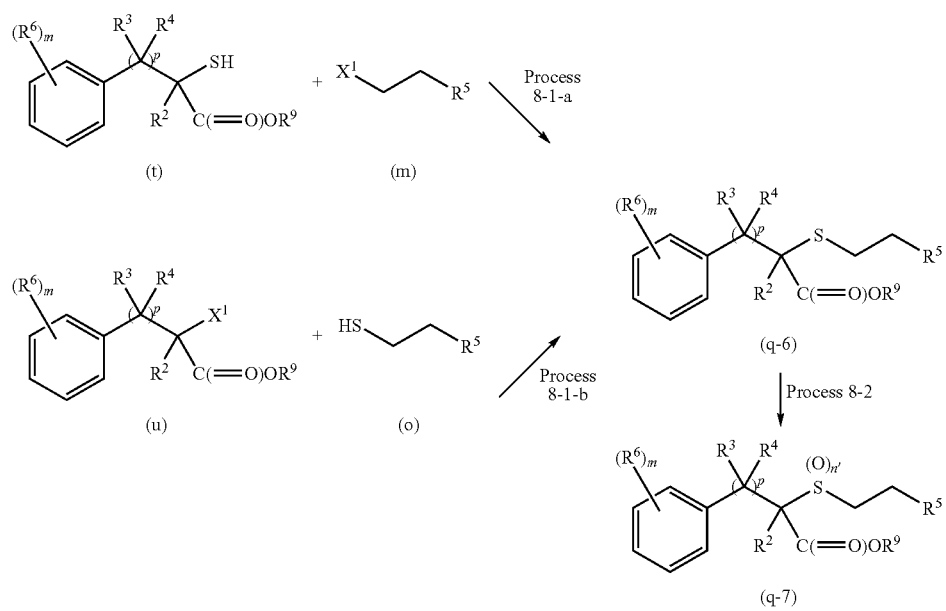

The reaction is usually carried out in a solvent in the presence of a base.

Examples of the solvent used in the reaction include acid amides such as N,N-dimethylformamide, ethers such as diethyl ether, 1,4-dioxane or tetrahydrofuran, organic sulfurs such as dimethyl sulfoxide or sulfolane, halogenated hydrocarbons such as chloroform, dichloromethane, 1,2-dichloroethane or chlorobenzene, aromatic hydrocarbons such as toluene or xylene, alcohols such as methanol or ethanol, water, and a mixture thereof.

Examples of the base used in the reaction include inorganic bases such as sodium hydride, potassium hydride, sodium hydroxide, potassium hydroxide, potassium carbonate or cesium carbonate, alkali metal alkoxides such as sodium thoxide or potassium tert-butoxide, alkali metal amides such as lithium diisopropylamide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (s).

The amount of the compound (h) used in the reaction is usually 1 to 10 mol per 1 mol of the compound (s).

The reaction temperature is usually in a range of −100 to 150° C., and the reaction time is usually 1 to 24 hours.

After completion of the reaction, the compound (q-5) can be isolated, for example, by pouring a reaction mixture into water and extracting the resulting mixture with an organic solvent, followed by concentration. The isolated compound (q-5) can be further purified by chromatography, recrystallization or the like, if necessary.

Reference Process 8

A compound represented by the formula (q-6) (hereinafter, referred to as the compound (q-6)) which is the compound (q) wherein n is 0 and a compound represented by the formula (q-7) (hereinafter, referred to as the compound (q-7)) which is the compound (q) wherein n is 1 or 2 can be produced by the following method:

wherein $R^2$, $R^3$, $R^4$, $R^5$, $R^6$, $R^9$, G, $X^1$, p, m and n are as defined above.

Process 8-1-a:

The compound (q-6) can be produced by reacting a compound represented by the formula (t) (hereinafter, referred to as the compound (t)) with the compound (m).

The reaction is usually carried out in a solvent in the presence of a base.

Examples of the solvent used in the reaction include acid amides such as N,N-dimethylformamide, ethers such as diethyl ether, 1,4-dioxane or tetrahydrofuran, organic sulfurs such as dimethyl sulfoxide or sulfolane, halogenated hydrocarbons such as chloroform, dichloromethane, 1,2-dichloroethane or chlorobenzene, aromatic hydrocarbons such as toluene or xylene, alcohols such as methanol or ethanol, water, and a mixture thereof.

Examples of the base used in the reaction include inorganic bases such as sodium hydride, potassium hydride, sodium hydroxide, potassium hydroxide, potassium carbonate or cesium carbonate, alkali metal alkoxides such as sodium methoxide or potassium tert-butoxide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (t).

The amount of the compound (m) used in the reaction is usually 1 to 10 mol per 1 mol of the compound (t).

The reaction temperature is usually in a range of −20 to 150° C., and the reaction time is usually 1 to 24 hours.

After completion of the reaction, the compound (q-6) can be isolated, for example, by pouring a reaction mixture into water and extracting the resulting mixture with an organic solvent, followed by concentration. The isolated compound (q-6) can be further purified by chromatography, recrystallization or the like, if necessary.

Process 8-1-b:

The compound (q-6) can be also produced by reacting a compound represented by the formula (u) (hereinafter, referred to as the compound (u)) with the compound (o).

The reaction is usually carried out in a solvent in the presence of a base.

Examples of the solvent used in the reaction include acid amides such as N,N-dimethylformamide, ethers such as diethyl ether, 1,4-dioxane or tetrahydrofuran, organic sulfurs such as dimethyl sulfoxide or sulfolane, halogenated hydrocarbons such as chloroform, dichloromethane, 1,2-dichloroethane or chlorobenzene, aromatic hydrocarbons such as toluene or xylene, alcohols such as methanol or ethanol, water, and a mixture thereof.

Examples of the base used in the reaction include inorganic bases such as sodium hydride, potassium hydride, sodium hydroxide, potassium hydroxide, potassium carbonate or cesium carbonate, alkali metal alkoxides such as sodium methoxide or potassium tert-butoxide, and organic bases such as triethylamine, 1,4-diazabicyclo[2.2.2]octane or 1,8-diazabicyclo[5.4.0]-7-undecene.

The amount of the base used in the reaction is usually 1 to 10 mol per 1 mol of the compound (u).

The amount of the compound (o) used in the reaction is usually 1 to 10 mol per 1 mol of the compound (u).

The reaction temperature is usually in a range of −20 to 150° C., and the reaction time is usually 1 to 24 hours.

After completion of the reaction, the compound (q-6) can be isolated, for example, by pouring a reaction mixture into water and extracting the resulting mixture with an organic solvent, followed by concentration. The isolated compound (q-6) can be further purified by chromatography, recrystallization or the like, if necessary.

Process 8-2:

The compound (q-7) can be produced by reacting the compound (q-6) with the oxidizing agent (x).

The reaction is usually carried out in a solvent.

Examples of the solvent used in the reaction include halogenated hydrocarbons such as chloroform, dichloromethane, 1,2-dichloroethane or chlorobenzene, organic hydrocarbons such as toluene or xylene, aliphatic carboxylic acids such as acetic acid or trifluoroacetic acid, alcohols such as methanol or ethanol, water, and a mixture thereof.

Examples of the oxidizing agent (x) used in the reaction include organic peroxides such as peracetic acid, trifuloroperacetic acid or m-chloroperbenzoic acid, halogens such as chlorine or bromine, halogen-containing imides such as N-chlorosuccinimide, halides such as perchloric acid (or a salt thereof) or periodic acid (or a salt thereof), permanganates such as potassium permanganate, chromates such as potassium chromate, and hydrogen peroxide.

The amount of the oxidizing agent (x) used in the reaction is usually 1 to 10 mol per 1 mol of the compound (q-6).

The reaction temperature is usually in a range of −50 to 200° C., and the reaction time is usually 1 to 72 hours.

After completion of the reaction, the compound (q-7) can be isolated, for example, by pouring a reaction mixture into water and extracting the resulting mixture with an organic solvent, followed by concentration. The isolated compound (q-7) can be further purified by chromatography, recrystallization or the like, if necessary.

Reference Process 9

The compound (f) can be produced by reacting the compound (d) with a halogenating agent (e) as shown below:

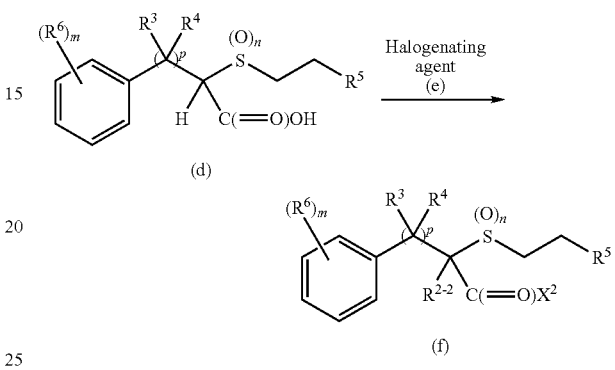

wherein $R^2$, $R^3$, $R^4$, $R^5$, $R^6$, $X^2$, p, m and n are as defined above.

The reaction is carried out without a solvent or in a solvent.

Examples of the solvent used in the reaction include halogenated hydrocarbons such as chloroform, dichloromethane, 1,2-dichloroethane or chlorobenzene, and aromatic hydrocarbons such as toluene or xylene.

Examples of the halogenating agent (e) include oxalyl chloride, thionyl chloride, thionyl bromide, phosphorus trichloride, phosphorus tribromide and phosphorus pentachloride.

The amount of the halogenating agent (e) used in the reaction is usually 1 to 10 mol per 1 mol of the compound (d).

The reaction temperature is usually in a range of −20 to 150° C., and the reaction time is usually 1 to 24 hours.

After completion of the reaction, the compound (f) can be isolated by concentration or the like. The isolated compound (f) can be further purified by distillation or the like, if necessary.

Examples of arthropod pests on which the compound of the present invention exhibits a controlling effect include harmful insects and harmful mites, and more specifically, the following arthropods.

Hemiptera:

Planthoppers (Delphacidae) such as small brown planthopper (*Laodelphax striatellus*), brown rice planthopper (*Nilaparvata lugens*), or white-backed rice planthopper (*Sogatella furcifera*); leafhoppers (Deltocephalidae) such as green rice leafhopper (*Nephotettix cincticeps*), green rice leafhopper (*Nephotettix virescens*), or tea green leafhopper (*Empoasca onukii*); aphids (Aphididae) such as cotton aphid (*Aphis gossypii*), green peach aphid (*Myzus persicae*), cabbage aphid (*Brevicoryne brassicae*), piraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), or mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), or stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), or citrus spiny white fly (*Aleurocanthus spiniferus*); scales (Coccidae) such as California red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), or white peach scale (*Pseudaulacaspis pentagona*); lace bugs (Tingidae); cimices such as *Cimex lectularius*; psyllids (Psyllidae); etc.

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), or bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., or *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes honmai.*), oriental tea tortrix (*Homona magnanima*), apple tortrix (*Archips fuscocupreanus*), or codling moth (*Cydia pomonella*); leafblotch miners (Gracillariidae) such as tea leafroller (*Caloptilia theivora*), or apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., or *Euproctis* spp.; yponomeutid moths (Yponomeutidae) such as diamondback (*Plutella xylostella*); gelechiid moths (Gelechiidae) such as pink bollworm (*Pectinophora gossypiella*), or potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), or webbing clothes moth (*Tineola bisselliella*); etc.

Thysanoptera:

Thrips (Thripidae) such as yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.

Diptera:

Culices such as common mosquito (*Culex pipiens pallens*), *Cluex tritaeniorhynchus*, or *Cluex quinquefasciatus*; *Aedes* spp. such as yellow fever mosquito (*Aedes aegypti*), or Asian tiger mosquito (*Aedes albopictus*); *Anopheles* spp. such as *Anopheles sinensis*; chironomids (Chironomidae); house flies (Muscidae) such as *Musca domestica*, or *Muscina stabulans*; blow flies (Calliphoridae); flesh flies (Sarcophagidae); little house flies (Fanniidae); anthomyiid flies (Anthomyiidae) such as seedcorn fly (*Delia platura*), or onion fly (*Delia antiqua*); leafminer flies (Agromyzidae) such as rice leafminer (*Agromyza oryzae*), little rice leafminer (*Hydrellia griseola*), tomato leafminer (*Liriomyza sativae*), legume leafminer (*Liriomyza trifolii*), or garden pea leafminer (*Chromatomyia horticola*); gout flies (Chloropidae) such as rice stem maggot (*Chlorops oryzae*); fruit flies (Tephritidae) such as melon fly (*Dacus cucurbitae*), or Mediterranean fruit fly (*Ceratitis capitata*); Drosophilidae; humpbacked flies (Phoridae) such as *Megaselia spiracularis*; moth flies (Psychodidae) such as *Clogmia albipunctata*; Simuliidae; Tabanidae such as horsefly (*Tabanus trigonus*); stable flies, etc.

Coleoptera:

Corn root worms (*Diabrotica* spp.) such as Western corn root worm (*Diabrotica virgifera virgifera*), or Sourthern corn root worm (*Diabrotica undecimpunctata howardi*); scarabs (Scarabaeidae) such as cupreous chafer (*Anomala cuprea*), soybean beetle (*Anomala rufocuprea*), or Japanese beetle (*Popillia japonica*); weevils such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), or hunting billbug (*Sphenophorus venatus*); darkling beetles (Tenebrionidae) such as yellow mealworm (*Tenebrio molitor*), or red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), or Colorado potato beetle (*Leptinotarsa decemlineata*); dermestid beetles (Dermestidae) such as varied carper beetle (*Anthrenus verbasci*), or hide beetle (*Dermestes maculates*); deathwatch beetles (Anobiidae) such as cigarette beetle (*Lasioderma serricorne*); *Epilachna* such as Twenty-eight-spotted ladybird (*Epilachna vigintioctopunctata*); bark beetles (Scolytidae) such as powder-post beetle (*Lyctus brunneus*), or pine shoot beetle (*Tomicus piniperda*); false powder-post beetles (Bostrychidae); spider beetles (Ptinidae); longhorn beetles (Cerambycidae) such as white-spotted longicorn beetle (*Anoplophora malasiaca*); click beetles (*Agriotes* spp.); *Paederus fuscipens*, etc.

Orthoptera:

Asiatic locust (*Locusta migratoria*), African mole cricket (*Gryllotalpa africana*), rice grasshopper (*Oxya yezoensis*), rice grasshopper (*Oxya japonica*), Gryllidae, etc.

Shiphonaptera:

Cat flea (*Ctenocephalides felis*), dog flea (*Ctenocephalides canis*), human flea (*Pulex irritans*), oriental rat flea (*Xenopsylla cheopis*), etc.

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), etc.

Hymenoptera:

Ants (Formicidae) such as pharaoh ant (*Monomorium pharaosis*), negro ant (*Formica fusca japonica*), black house ant (*Ochetellus glaber*), *Pristomyrmex pungens*, *Pheidole noda*, leaf-cutting ant (*Acromyrmex* spp.), or fire ant (*Solenopsis* spp.); hornets (Vespidae); bethylid wasps (Betylidae); sawflies (Tenthredinidae) such as cabbage sawfly (*Athalia rosae*), or *Athalia japonica*, etc.

Blattodea:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*);

Isoptera:

Termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumesis*, *Glyptotermes nakajimai*, *Glyptotermes fuscus*, *Glyptotermes kodamai*, *Glyptotermes kushimensis*, Japanese dampwood termite (*Hodotermopsis*

*japonica*), *Coptotermes guangzhoensis*, *Reticulitermes miyatakei*, eastern subterranean termite (*Reticulitermes flavipes amamianus*), *Reticulitermes* sp., *Nasutitermes takasagoesis*, *Pericapritermes nitobei*, or *Sinocapritermes mushae*, etc.

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), or *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, or apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis*, *Haemaphysalis flava*, *Dermacentor taiwanicus*, American dog tick (*Dermacentor variabilis*), *Ixodes ovatus*, *Ixodes persulcatus*, black leg tick (*Ixodes scapularis*), lone star tick (*Amblyomma americanum*), *Boophilus microplus*, or *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*); acarid mites (Acaridae) such as mold mite (*Tyrophagus putrescentiae*), or *Tyrophagus similis*; house dust mites (Pyroglyphidae) such as *Dermatophagoides farinae*, or *Dermatophagoides ptrenyssnus*; cheyletide mites (Cheyletidae) such as *Cheyletus eruditus*, *Cheyletus malaccensis*, or *Cheyletus moorei*; parasitoid mites (Dermanyssidae) such as tropical rat mite (*Ornithonyssus bacoti*), northern fowl mite (*Ornithonyssus sylviarum*), or poultry red mite (*Dermanyssus gallinae*); chiggers (Trombiculidae) such as *Leptotrombidium akamushi*; spiders (Araneae) such as Japanese foliage spider (*Chiracanthium japonicum*), or redback spider (*Latrodectus hasseltii*), etc.

Chilopoda: house centipede (*Thereuonema hilgendorfi*), *Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginates*, *Limax flavus*, etc.

Although the pesticidal composition of the present invention may be the compound of the present invention itself, the pesticidal composition of the present invention usually comprises the compound of the present invention in combination with a solid carrier, a liquid carrier and/or a gaseous carrier, and if necessary, a surfactant or other pharmaceutical additives and takes the form of an emulsifiable concentrate, an oil solution, a shampoo formulation, a flowable formulation, a dust, a wettable powder, a granule, a paste formulation, a microcapsule formulation, a foam formulation, an aerosol formulation, a carbon dioxide gas formulation, a tablet, a resin formulation or the like. The pesticidal composition of the present invention may be processed into a poison bait, a mosquito coil, an electric mosquito mat, a smoking pesticide, a fumigant or a sheet, and then be used.

The pesticidal composition of the present invention usually contains 0.1 to 95% by weight of the compound of the present invention.

Examples of the solid carrier include finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), chemical fertilizers (e.g., ammonium sulfate, ammonium phosphate, ammonium nitrate, ammonium chloride, urea, etc.) and the like.

Examples of the liquid carrier include aromatic or aliphatic hydrocarbons (e.g., xylene, toluene, alkylnaphthalene, phenylxylylethane, kerosene, light oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone etc.), nitriles (e.g., acetonitrile, isobutyronitrile etc.), sulfoxides (e.g., dimethyl sulfoxide etc.), acid amides (e.g., N,N-dimethylformamide, N,N-dimethylacetamide etc.), vegetable oils (e.g., soybean oil, cottonseed oil etc.), vegetable essential oils (e.g., orange oil, hyssop oil, lemon oil, etc.), water and the like.

Examples of the gaseous carrier include butane gas, chlorofluorocarbon, LPG (liquefied petroleum gas), dimethyl ether, carbon dioxide gas and the like.

Examples of the surfactant include alkyl sulfate salts, alkyl sulfonate salts, alkylaryl sulfonate salts, alkyl aryl ethers and their polyoxyethylated derivatives, polyethylene glycol ethers, polyhydric alcohol esters, and sugar alcohol derivatives.

Examples of other pharmaceutical additives include a binder, a dispersant, a stabilizer and the like, and specific examples thereof include casein, gelatin, polysaccharides (e.g., starch, gum arabic, cellulose derivatives, alginic acid, etc.), lignin derivatives, bentonite, saccharides, synthetic water-soluble polymers (e.g., polyvinyl alcohol, polyvinylpyrrolidone, polyacrylic acid, etc.), PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids, and fatty acid esters.

Examples of a base material for a resin formulation include vinyl chloride polymers, polyurethane and the like. To the base material, if necessary, a plasticizer such as phthalate (e.g., dimethyl phthalate, dioctyl phthalate, etc.), adipate, stearic acid or the like may be added. The resin formulation is obtained by kneading the compound of the present invention into the base material using a conventional kneading apparatus, followed by molding such as injection molding, extrusion molding, press molding or the like. The resulting resin formulation may be formed into the shape of a plate, a film, a tape, a net, a string or the like via a further step of molding, cutting, or the like, if necessary. These resin formulations may be used, for example, in the form of an animal collar, an animal ear tag, a sheet formulation, a lead, or a horticultural post.

Examples of a base material of a poison bait include cereal powder, vegetable oil, sugar, crystalline cellulose and the like. To the base material, if necessary, an antioxidant such as dibutylhydroxytoluene or nordihydroguaiaretic acid, a preservative such as dehydroacetic acid, an agent for preventing children or pets from erroneously eating such as hot pepper powder, a pest-attractive perfume such as cheese perfume, onion perfume or peanut oil or the like may be added.

The pesticidal composition of the present invention can be applied, for example, to arthropod pests directly and/or a place where arthropod pests inhabit (e.g., plants, animals, soil, etc.).

The pesticidal composition of the present invention can be used at crop lands such as cultivated lands, paddy fields, lawns and orchards. The pesticidal composition of the present invention can control arthropod pests at crop lands without causing drug damage to crop plants which are cultivated at the crop lands, in some cases.

Examples of such crop plants are listed below.

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers and ornamental plants;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The aforementioned crop plants include those to which resistance to an HPPD inhibitor such as isoxaflutole, an ALS inhibitor such as imazethapyr or thifensulfuron-methyl, an EPSP synthesizing enzyme inhibitor, a glutamine synthesizing enzyme inhibitor, an acetyl CoA carboxylase inhibitor, or an herbicide such as bromoxynil has been imparted by a classical breeding method or a genetic engineering technique.

Examples of the crop plant to which the resistance has been imparted by a classical breeding method include Clearfield (registered trademark) canola which is resistant to an imidazolinone herbicide such as imazethapyr, and STS soybean which is resistant to a sulfonylurea ALS inhibitor herbicide such as thifensulfuron-methyl, as well as SR corn which is resistant to an acetyl CoA carboxylase inhibitor such as trione oxime hebicides or aryloxyphenoxypropionic acid herbicides. For example, a crop plant to which the resistance to an acetyl CoA carboxylase inhibitor has been imparted is found in Proc. Natl. Acad. Sci. USA, 1990, vol. 87, p. 7175-7179. In addition, a mutant acetyl CoA carboxylase which is resistant to an acetyl CoA carboxylase inhibitor is described in Weed Science, vol. 53, p. 728-746, 2005. When a gene encoding the mutant acetyl CoA carboxylase is introduced into a crop plant by a genetic engineering technique or when a mutation related to impartation of the acetyl CoA carboxylase resistance is introduced into a gene encoding acetyl CoA carboxylase of a crop plant, a crop plant resistant to an acetyl CoA carboxylase inhibitor can be produced. Further, nucleic acids for introduction of a base substitution mutation can be introduced into the cells of a crop plant by chimeraplasty (see, Gura T. 1999, Repairing the Genome's Spelling Mistakes, Science 285: 316-318) to induce a site-directed amino acid substitution mutation in the gene which is targeted by an acetyl CoA carboxylase inhibitor or herbicide of the crop plant, and thereby a crop plant resistant to an acetyl CoA carboxylase inhibitor or herbicide can be produced.

Examples of the crop plant to which the resistance has been imparted by a genetic engineering technique include corn cultivars which are resistant to glyphosate and glufosinate. Some of such corn cultivars are sold under the trade name of RoundupReady (registered trademark) and LibertyLink (registered trademark).

The aforementioned crop plants include those to which ability to produce an insecticidal toxin, for example a selective toxin known to be produced by *Bacillus*, has been imparted by a genetic engineering technique.

Examples of the insecticidal toxin which is produced by such a genetically engineered plant include insecticidal proteins derived from *Bacillus cereus* and *Bacillus popilliae*; δ-endotoxins derived from *Bacillus thuringiensis*, such as Cry1Ab, Cry1Ac, Cry1F, Cry1Fa2, Cry2Ab, Cry3A, Cry3Bb1 or Cry9C; insecticidal proteins derived from *Bacillus thuringiensis*, such as VIP 1, VIP 2, VIP 3 or VIP 3A; insecticidal proteins derived from nematodes; toxins produced by animals such as scorpion toxins, spider toxins, bee toxins or insect-specific nerve toxins; fungal toxins; plant lectin; agglutinin; protease inhibitors such as trypsin inhibitors, serine protease inhibitors, patatin, cystatin, or papain inhibitors; ribosome-inactivating proteins (RIP) such as ricin, corn-RIP, abrin, saporin, or briodin; steroid metabolizing enzymes such as 3-hydroxysteroid oxidase, ecdysteroid-UDP-glucosyltransferase, or cholesterol oxidase; ecdysone inhibitors; HMG-CoA reductase; ion channel inhibitors such as sodium channel inhibitors or calcium channel inhibitors; juvenile hormone esterase; diuretic hormone receptors; stilbene synthase; bibenzyl synthase; chitinase; and glucanase.

The insecticidal toxin which is produced by such a genetically engineered plant also includes hybrid toxins of different insecticidal proteins, for example, δ-endotoxins such as Cry1Ab, Cry1Ac, Cry1F, Cry1Fa2, Cry2Ab, Cry3A, Cry3Bb1 or Cry9C and insecticidal proteins such as VIP 1, VIP 2, VIP 3 or VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-0 374 753, WO 93/07278, WO 95/34656, EP-A-0 427 529, EP-A-451878, WO 03/052073, and the like.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Herculex I (registered trademark) (a corn cultivar expressing Cry1Fa2 toxin and phosphinothricin N-acetyltransferase (PAT) for imparting resistance to gluphosinate), NuCOTN33B (registered trademark) (a cotton cultivar expressing Cry1Ac toxin), Bollgard I (registered trademark) (a cotton cultivar expressing Cry1Ac toxin), Bollgard II (registered trademark) (a cotton cultivar expressing Cry1Ac and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (registered trademark) (GA21 glyphosate-resistance character), Agrisure CB Advantage (registered trademark) (Btll corn borer (CB) character), Protecta (registered trademark), and the like.

The aforementioned crop plants include those to which ability to produce an anti-pathogen substance has been imparted by a genetic engineering technique.

Examples of the anti-pathogen substance include PR proteins (PRPs described in EP-A-0 392 225); ion channel inhibitors such as sodium channel inhibitors, or calcium channel inhibitors (e.g. KP1, KP4, KP6 toxins etc. produced by viruses); stilbene synthase; bibenzyl synthase; chitinase; glucanase; substances produced by microorganisms such as peptide antibiotics, heterocycle-containing antibiotics, or protein factors involved in plant disease-resistance (as described in WO 03/000906); and the like. Such anti-pathogen substances and genetically engineered plants which produce the anti-pathogen substances are described in EP-A-0 392 225, WO 05/33818, EP-A-0 353 191, and the like.

When the pesticidal composition of the present invention is used for controlling pests in agriculture and forestry, the application amount is usually 1 to 10,000 g/ha, preferably 10 to 500 g/ha of the compound of the present invention as the active ingredient. When the pesticidal composition of the present invention is the form of an emulsifiable concentrate, a wettable powder, a flowable formulation or a microcapsule formulation, it is usually used after dilution with water so as to have the compound of the present invention as an active ingredient concentration of 0.01 to 1,000 ppm. When the pesticidal composition of the present invention is the form of a dust or a granule, it is usually used as it is. The pesticidal composition of the present invention may be sprayed directly to plants to be protected from arthropod pests. Alternatively, soil can be treated with the pesticidal composition of the present invention to control arthropod pests living in the soil. Seedbeds before planting or planting holes or plant feet in planting can be also treated with the pesticidal composition of the present invention. Further, a sheet formulation of the pesticidal composition of the present invention may be applied by winding around plants, disposing in the vicinity of plants, laying on the soil surface at the plant feet, or the like.

When the pesticidal composition of the present invention is used for control of epidemic, the application amount is usually 0.001 to 10 mg/m$^3$ of the compound of the present invention as the active ingredient for application to space, and 0.001 to 100 mg/m$^2$ of the active ingredient for application to a plane. The pesticidal composition in the form of an emulsifiable concentrate, a wettable powder or a flowable formulation is usually applied after dilution with water so as to contain usually 0.001 to 10,000 ppm of the active ingredient. The pesticidal composition in the form of an oil solution, an aerosol formulation, a smoking pesticide or a poison bait is usually applied as it is.

When the pesticidal composition of the present invention is used for controlling external parasites of livestock such as a cow, a horse, a pig, a sheep, a goat or a chicken, or small animals such as a dog, a cat, a rat or a mouse, it can be applied to said animals by a known method in the veterinary filed. Specifically, when systemic control is intended, the pesticidal composition of the present invention is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil solution or an aqueous liquid, washing an animal with the pesticidal composition in the form of a shampoo formulation, and attachment of a collar or a ear tag made of the pesticidal composition in the form of a resin formulation to an animal. When administered to an animal, the amount of the compound of the present invention is usually in the range of 0.1 to 1,000 mg per 1 kg body weight of the animal.

The pesticidal composition of the present invention may be used in admixture or combination with other insecticides, nematocides, acaricides, fungicides, herbicides, plant growth regulators, synergists, fertilizers, soil conditioners, animal feed, and the like.

Examples of an active ingredient of such insecticide include (1) Organic Phosphorus Compounds:

acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) Carbamate Compounds:

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) Synthetic Pyrethroid Compounds:

acrinathrin, allethrin, beta-cyfluthrin, bifenthrin, cyclopro-thrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethy 3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6- tetrafluoro-4-(methoxymethyl)benzyl 2,2,3,3-tetramethylcyclopropanecarboxylate, and the like;

(4) Nereistoxin Compounds:
cartap, bensultap, thiocyclam, monosultap, bisultap, and the like;

(5) Neonicotinoid Compounds:
imidacloprid, nitenpyram, acetamiprid, thiamethoxam, thiacloprid, dinotefuran, clothianidin, and the like;

(6) Benzoylurea Compounds:
chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole Compounds:
acetoprole, ethiprole, fipronil, vaniliprole, pyriprole, pyrafluprole, and the like;

(8) Bt Toxin Insecticides:
live spores derived from *Bacillus thuringiesis* and crystal toxins produced therefrom as well as a mixture thereof;

(9) Hydrazine Compounds:
chromafenozide, halofenozide, methoxyfenozide, tebufenozide, and the like;

(10) Organic Chlorine Compounds:
aldrin, dieldrin, dienochlor, endosulfan, methoxychlor, and the like;

(11) Natural Insecticides:
machine oil, nicotine sulfate, and the like; (12) Other Insecticides:
avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, a compound represented by the following formula (A):

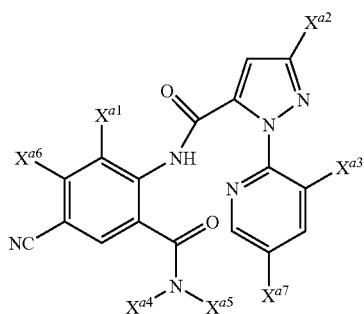

(A)

wherein $X^{a1}$ represents a methyl group, a chlorine atom, a bromine atom or a fluorine atom, $X^{a2}$ represents a fluorine atom, a chlorine atom, a bromine atom, a C1-C4 haloalkyl grop or a C1-C4 haloalkoxy group, $X^{a3}$ represents a fluorine atom, a chlorine atom or a bromine atom, $X^{a4}$ represents an optionally substituted C1-C4 alkyl group, an optionally substituted C3-C4 alkenyl group, an optionally substituted C3-C4 alkynyl group, an optionally substituted C3-C5 cycloalkylalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom;

a compound represented by the following formula (B):

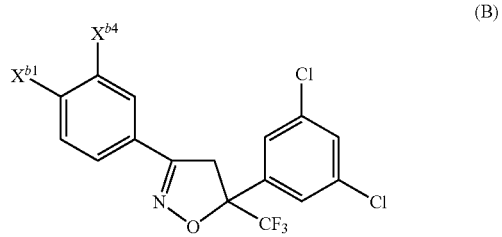

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group, or an optionally substituted 1,2,4-triazol-1-yl group, $X^{b2}$ represents an optionally substituted C1-C4 haloalkyl group, such as a 2,2,2-trifluoroethyl group, or an optionally substituted C3-C6 cycloalkyl group, such as a cyclopropyl group, $X^{b3}$ represents an optionally substituted C1-C4 alkyl group, such as a methyl group, and $X^{b4}$ represents a hydrogen atom, a chlorine atom, a cyano group or a methyl group;

a compound represented by the following formula (C):

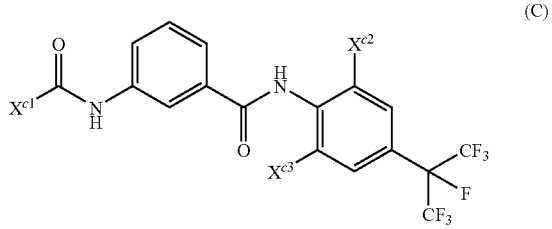

(C)

wherein $X^{c1}$ represents an optionally substituted C1-C4 alkyl group such as a 3,3,3-trifluoropropyl group, an optionally substituted C1-C4 alkoxy group such as a 2,2,2-trichloroethoxy group, an optionally substituted phenyl group such as a 4-cyanophenyl group, or an optionally substituted pyridyl group such as a 2-chloro-3-pyridyl group, $X^{c2}$ represents a methyl group or a trifluoromethylthio group, and $X^{c3}$ represents a methyl group or a halogen atom; and the like.

Examples of an active ingredient of the acaricide include acequinocyl, amitraz, benzoximate, bifenazate, bromopropylate, chinomethionate, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, cyenopyrafen, and the like.

Examples of the nematicide include DCIP, fosthiazate, levamisol hydrochloride, methylisothiocyanate, morantel tartarate, imicyafos, and the like.

Examples of an active ingredient of such fungicide include strobilurin compounds such as azoxystrobin; organophosphate compounds such as tolclofos-methyl; azole compounds such as triflumizole, pefurazoate or difenoconazole; fthalide, flutolanil, validamycin, probenazole, diclomezine, pencycuron, dazomet, kasugamycin, IBP, pyroquilon, oxolinic acid, tricyclazole, ferimzone, mepronil, EDDP, isoprothiolane, carpropamid, diclocymet, furametpyr, fludioxonil, procymidone and diethofencarb.

EXAMPLES

Hereinafter, the present invention is described in more detail by referrence to Production Examples, Formulation Examples and Test Examples which the present invention is not limited to.

First, Production Examples of the compound of the present invention are shown.

Production Example 1

To a solution of 0.5 g of methyl 2-fluoro-2-(3,4,5-trifluorophenyl)-2-(3,3,3-trifluoropropylsulfonyl)acetate in 20 ml of methanol was added 0.6 ml of a 7M solution of ammonia in methanol at room temperature, and the mixture was stirred at the same temperature for 14 hours. The reaction mixture was concentrated under reduced pressure. The residue was subjected to column chromatography to obtain 0.35 g of 2-fluoro-2-(3,3,3-trifluoropropylsulfonyl)-2-(3,4,5-trifluorophenyl)acetamide (hereinafter, referred to as the present compound (1)).

Present compound (1):

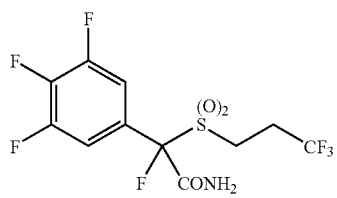

(1)

$^1$H-NMR (CDCl$_3$, TMS): δ (ppm) 7.56-7.65 (2H, m), 6.57 (1H, bs), 5.91 (1H, bs), 3.56-3.73 (2H, m), 3.23-3.48 (2H, m).

Production Example 2

To a solution of 1.0 g of methyl 2-(3,4,5-trifluorophenyl)-2-(3,3,3-trifluoropropylsulfonyl)propanoate in 2.0 ml of methanol was added 8.0 ml of a 7M solution of ammonia in methanol at room temperature, and the mixture was stirred at the same temperature for 48 hours. The reaction mixture was concentrated under reduced pressure. The residue was subjected to column chromatography to obtain 0.20 g of 2-(3,4,5-trifluorophenyl)-2-(3,3,3-trifluoropropylsulfonyl)propaneamide (hereinafter, referred to as the present compound (2)).

Present compound (2):

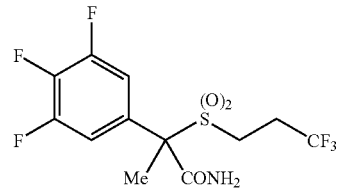

(2)

$^1$H-NMR (CDCl$_3$, TMS): δ (ppm) 7.36 (2H, dd), 6.41 (1H, bs), 6.15 (1H, bs), 3.26-3.58 (2H, m), 2.50-2.74 (2H, m) 2.08 (3H, s).

Production Example 3

To a solution of 0.8 g of methyl 2-(4-chloro-3-fluorophenyl)-2-fluoro-2-(3,3,3-trifluoropropylsulfonyl)acetate in 20 ml of methanol was added 1.5 ml of a 7M solution of ammonia in methanol at room temperature, and the mixture was stirred at the same temperature for 16 hours. The reaction mixture was concentrated under reduced pressure. The residue was subjected to column chromatography to obtain 0.60 g of 2-(4-chloro-3-fluorophenyl)-2-fluoro-2-(3,3,3-trifluoropropylsulfonyl)acetamide (hereinafter, referred to as the present compound (3)).

Present compound (3):

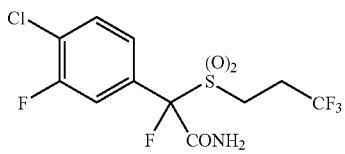

(3)

$^1$H-NMR (CDCl$_3$, TMS): δ (ppm) 7.74 (1H, dd), 7.64 (1H, dd), 7.55 (1H, dd), 6.60 (1H, bs), 6.02 (1H, bs) e, 3.21-3.46 (2H, m), 2.49-2.69 (2H, m)

Production Example 4

To a solution of 0.6 g of methyl 2-(4-chlorophenyl)-2-fluoro-2-(3,3,3-trifluoropropylsulfonyl)acetate in 30 ml of methanol was added 0.7 ml of a 7M solution of ammonia in methanol at room temperature, and the mixture was stirred at the same temperature for 10 hours. The reaction mixture was concentrated under reduced pressure. The residue was subjected to column chromatography to obtain 0.40 g of 2-(4-chlorophenyl)-2-fluoro-2-(3,3,3-trifluoropropylsulfonyl)acetamide (hereinafter, referred to as the present compound (4)).

Present compound (4):

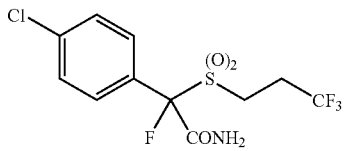

(4)

$^1$H-NMR (CDCl$_3$, TMS): δ (ppm) 7.86 (2H, d), 7.49 (2H, d), 6.57 (1H, bs), 5.92 (1H, bs), 3.20-3.45 (2H, m), 2.43-2.68 (2H, m).

Production Example 5

To a solution of 0.4 g of methyl 2-fluoro-2-(4-trifluoromethylphenyl)-2-(3,3,3-trifluoropropylsulfonyl)acetate in 30 ml of methanol was added 0.4 mL of a 7M solution of ammonia in methanol at room temperature, and the mixture was stirred at the same temperature for 4 days. The reaction mixture was concentrated under reduced pressure. The residue was subjected to column chromatography to obtain 0.25 g of 2-fluoro-2-(3,3,3-trifluoropropylsulfonyl)-2-(4-trifluoromethylphenyl)acetamide (hereinafter, referred to as the present compound (5)).

Present compound (5):

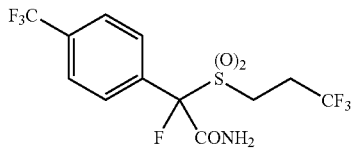

(5)

$^1$H-NMR (CDCl$_3$, TMS): δ (ppm) 8.06 (2H, d), 7.78 (2H, d) 6.58 (1H, bs), 5.92 (1H, bs), 3.22-3.48 (2H, m), 2.52-2.68 (2H, m).

Production Example 6

To a solution of 1.69 g of 2-(4-chlorophenyl)-2-(3,3,3-trifluoropropylsulfanyl)acetic acid and 0.81 g of thionyl chloride in 15 mL of toluene was added one drop of N,N-dimethylformamide at room temperature, and the mixture was stirred at 80° C. for an hour. The reaction mixture was concentrated. The residue was dissolved in 10 ml of tetrahydrofuran, and thereto 4.0 ml of a 28% aqueous ammonia solution was added at room temperature. The mixture was stirred at the same temperature for 0.5 hour, followed by extraction with ethyl acetate. The organic layer was dried over anhydrous sodium sulfate and concentrated under reduced pressure. The residue was subjected to silica gel column chromatography to obtain 1.52 g of 2-(4-chlorophenyl)-2-(3,3,3-trifluoropropylsulfanyl)acetamide (hereinafter, referred to as the present compound (6)).

Present compound (6):

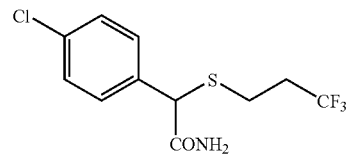

(6)

$^1$H-NMR (CDCl$_3$, TMS): δ (ppm) 7.36-7.34 (4H, m), 6.30 (1H, bs), 5.89 (1H, bs), 4.54 (1H, s), 2.81-2.69 (2H, m), 2.46-2.31 (2H, m).

Production Example 7

To a solution of 0.40 g of 2-(4-chlorophenyl)-2-(3,3,3-trifluoropropylsulfanyl)acetamide in 10 ml of chloroform was added 0.76 g of meta-chloroperbenzoic acid (67%) at room temperature. The mixture was stirred at room temperature for 3 hours and then refluxed for 10 hours. The reaction mixture was washed subsequently with an aqueous sodium sulfite solution and an aqueous saturated sodium hydrogen carbonate solution, dried over anhydrous sodium sulfate and then concentrated under reduced pressure. The residue was subjected to silica gel column chromatography to obtain 0.30 g of 2-(4-chlorophenyl)-2-(3,3,3-trifluoropropylsulfonyl)acetamide (hereinafter, referred to as the present compound (7)).

Present compound (7):

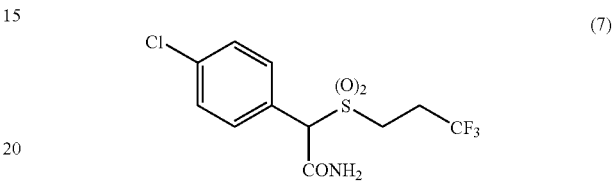

(7)

$^1$H-NMR (DMSO-D$_6$, TMS): δ (ppm) 7.76 (1H, bs), 7.64-7.61 (2H, m), 7.56-7.53 (2H, m), 5.42 (1H, s), 3.57-3.54 (1H, m), 3.33-3.29 (1H, m), 2.81-2.56 (2H, m).

Production Example 8

To a solution of 0.33 g of methyl 2-chloro-3-(4-trifluoromethylphenyl)-2-(3,3,3-trifluoropropylsulfonyl)propanoate in 3.0 ml of methanol was added 1.0 ml of a 7M solution of ammonia in methanol at room temperature, and the mixture was stirred at the same temperature for 28 hours. The reaction mixture was concentrated under reduced pressure. The residue was subjected to column chromatography to obtain 0.20 g of 2-chloro-3-(4-trifluoromethylphenyl)-2-(3,3,3-trifluoropropylsulfonyl)propaneamide (hereinafter, referred to as the present compound (8)).

Present compound (8):

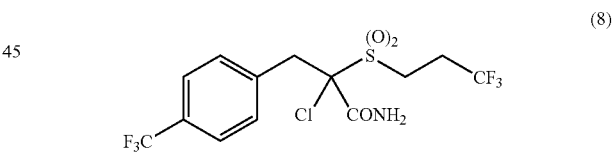

(8)

$^1$H-NMR (CDCl$_3$, TMS): δ (ppm) 7.61 (2H, d), 7.44 (2H, d), 6.67 (1H, bs), 5.77 (1H, bs), 4.13 (1H, d), 3.93-3.85 (1H, m), 3.56-3.48 (1H, m), 3.41 (1H, d), 2.83-2.76 (2H, m).

Production Example 9

To a solution of 0.23 g of 2-chloro-3-(3-trifluoromethylphenyl)-2-(3,3,3-trifluoropropylsulfonyl)propanoate in 3.0 ml of methanol was added 0.8 ml of a 7M solution of ammonia in methanol at room temperature, and the mixture was stirred at the same temperature for 2 hours. The reaction mixture was concentrated under reduced pressure. The residue was subjected to column chromatography to obtain 0.13 g of 2-chloro-3-(3-trifluoromethylphenyl)-2-(3,3,3-trifluoropropylsulfonyl)propaneamide (hereinafter, referred to as the present compound (9)).

Present compound (9):

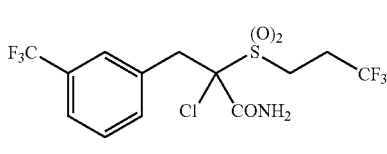

$^1$H-NMR (CDCl$_3$, TMS): δ (ppm) 7.61-7.59 (2H, m), 7.52-7.45 (2H, m), 6.67 (1H, bs), 5.89 (1H, bs), 4.13 (1H, d), 3.91-3.87 (1H, m), 3.56-3.48 (1H, m), 3.41 (1H, d), 2.81-2.77 (2H, m).

Production Example 10

To a solution of 0.61 g of methyl 2-chloro-3-(2-trifluoromethylphenyl)-2-(3,3,3-trifluoropropylsulfonyl)propanoate in 3.0 ml of methanol was added 5.2 ml of a 7M solution of ammonia in methanol at room temperature, and the mixture was stirred at the same temperature for 2 hours. The reaction mixture was concentrated under reduced pressure. The residue was subjected to column chromatography to obtain 0.20 g of 2-chloro-3-(2-trifluoromethylphenyl)-2-(3,3,3-trifluoropropylsulfonyl)propaneamide (hereinafter, referred to as the present compound (10)).

Present compound (10):

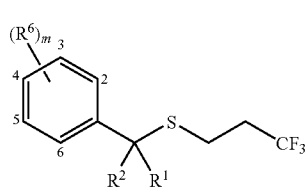

$^1$H-NMR (CDCl$_3$, TMS): δ (ppm) 7.72 (1H, d), 7.52-7.50 (1H, m), 7.45-7.43 (2H, m), 6.95 (1H, bs), 6.41 (1H, bs), 4.28 (1H, d), 3.87-3.80 (2H,m), 3.58-3.50 (1H, m), 2.82-2.76 (2H, m).

Then, specific examples of the compound of the present invention are shown.

A compound represented by the formula (I-1):

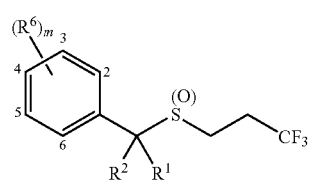

wherein R$^2$, R$^1$ and (R$^6$)$_m$ are any one of combinations shown below.

A compound represented by the formula (I-2):

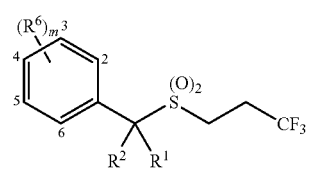

wherein R$^2$, R$^1$ and (R$^6$)$_m$ are any one of combinations shown below.

A compound represented by the formula (I-3):

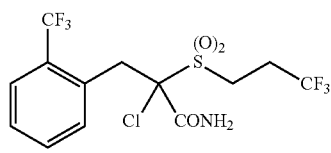

wherein R$^2$, R$^1$ and (R$^6$)$_m$ are any one of combinations shown below.

A compound represented by the formula (I-4):

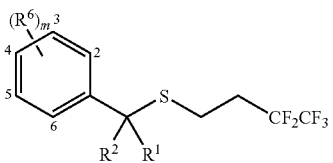

wherein R$^2$, R$^1$ and (R$^6$)$_m$ are any one of combinations shown below.

A compound represented by the formula (I-5):

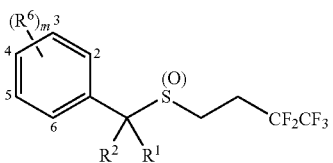

wherein R$^2$, R$^1$ and (R$^6$)$_m$ are any one of combinations shown below.

A compound represented by the formula (I-6):

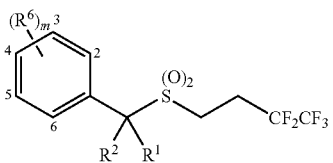

wherein R$^2$, R$^1$ and (R$^6$)$_m$ are any one of combinations shown below.

A compound represented by the formula (I-7):

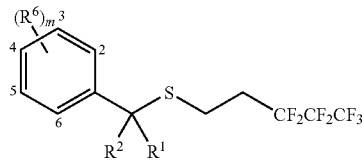
(I-7)

wherein $R^2$, $R^1$ and $(R^6)_m$ are any one of combinations shown below.

A compound represented by the formula (I-8):

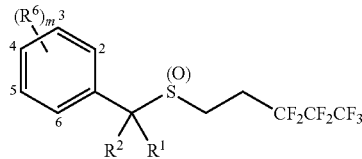
(I-8)

wherein $R^2$, $R^1$ and $(R^6)_m$ are any one of combinations shown below.

A compound represented by the formula (I-9):

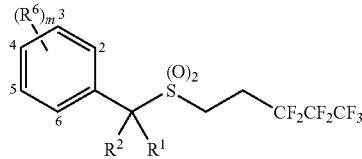
(I-9)

wherein $R^2$, $R^1$ and $(R^6)_m$ are any one of combinations shown below.

A compound represented by the formula (I-10):

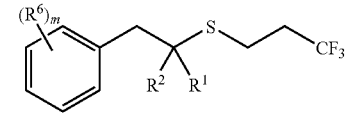
(I-10)

wherein $R^2$, $R^1$ and $(R^6)_m$ are any one of combinations shown below.

A compound represented by the formula (I-11):

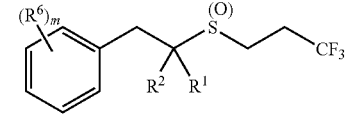
(I-11)

wherein $R^2$, $R^1$ and $(R^6)_m$ are any one of combinations shown below.

A compound represented by the formula (I-12):

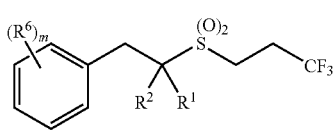
(I-12)

wherein $R^2$, $R^1$ and $(R^6)_m$ are any one of combinations shown below.

A compound represented by the formula (I-13):

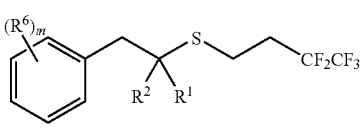
(I-13)

wherein $R^2$, $R^1$ and $(R^6)_m$ are any one of combinations shown below.

A compound represented by the formula (I-14):

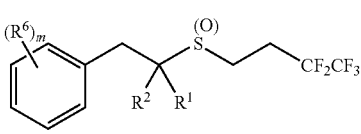
(I-14)

wherein $R^2$, $R^1$ and $(R^6)_m$ are any one of combinations shown below.

A compound represented by the formula (I-15):

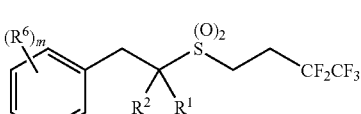
(I-15)

wherein $R^2$, $R^1$ and $(R^6)_m$ are any one of combinations shown below.

A compound represented by the formula (I-16):

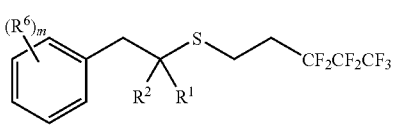
(I-16)

wherein $R^2$, $R^1$ and $(R^6)_m$ are any one of combinations shown below.

A compound represented by the formula (I-17):

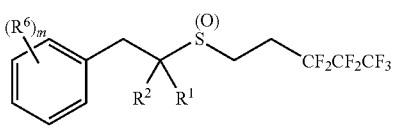
(I-17)

wherein $R^2$, $R^1$ and $(R^6)_m$ are any one of combinations shown below.

A compound represented by the formula (I-18):

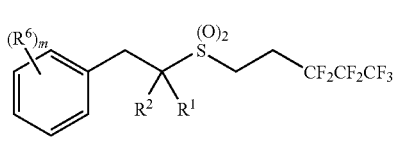
(I-18)

wherein $R^2$, $R^1$ and $(R^6)_m$ are any one of combinations shown below.

A compound represented by the formula (I-19):

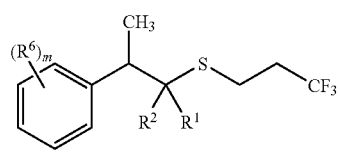
(I-19)

wherein $R^2$, $R^1$ and $(R^6)_m$ are any one of combinations shown below.

A compound represented by the formula (I-20):

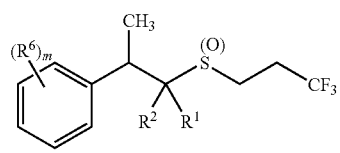
(I-20)

wherein $R^2$, $R^1$ and $(R^6)_m$ are any one of combinations shown below.

A compound represented by the formula (I-21):

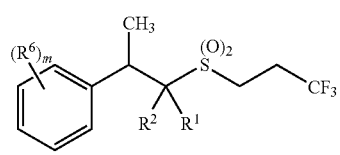
(I-21)

wherein $R^2$, $R^1$ and $(R^6)_m$ are any one of combinations shown below.

A compound represented by the formula (I-22):

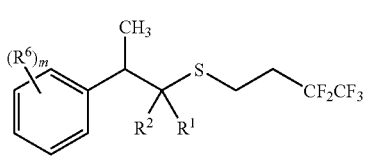
(I-22)

wherein $R^2$, $R^1$ and $(R^6)_m$ are any one of combinations shown below.

A compound represented by the formula (I-23):

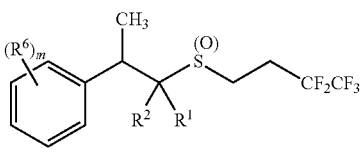
(I-23)

wherein $R^2$, $R^1$ and $(R^6)_m$ are any one of combinations shown below.

A compound represented by the formula (I-24):

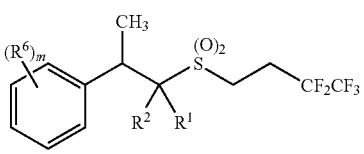
(I-24)

wherein $R^2$ $R^1$ and $(R)_m$ are any one of combinations shown below.

A compound represented by the formula (I-25):

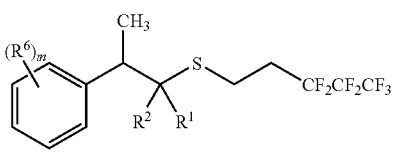
(I-25)

wherein $R^2$, $R^1$ and $(R^6)_m$ are any one of combinations shown below.

A compound represented by the formula (I-26):

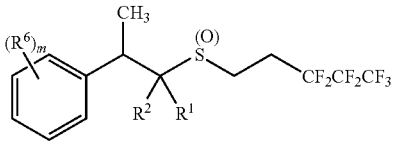
(I-26)

wherein $R^2$, $R^1$ and $(R^6)_m$ are any one of combinations shown below.

A compound represented by the formula (I-27):

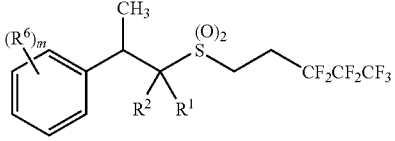
(I-27)

wherein $R^2$, $R^1$ and $(R^6)_m$ are any one of combinations shown below.

A compound represented by the formula (I-28):

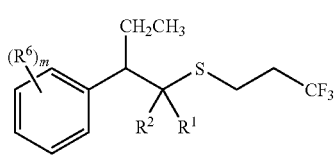
(I-28)

wherein $R^2$, $R^1$ and $(R^6)_m$ are any one of combinations shown below.

A compound represented by the formula (I-29):

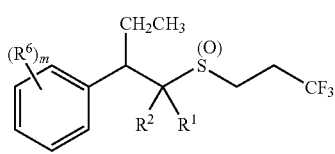
(I-29)

wherein $R^2$, $R^1$ and $(R^6)_m$ are any one of combinations shown below.

Aa compound represented by the formula (I-30):

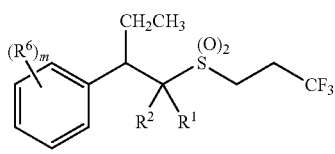
(I-30)

wherein $R^2$, $R^1$ and $(R^6)_m$ are any one of combinations shown below.

A compound represented by the formula (I-31):

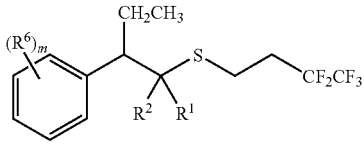
(I-31)

wherein $R^2$, $R^1$ and $(R^6)_m$ are any one of combinations shown below.

A compound represented by the formula (I-32):

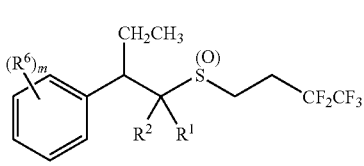
(I-32)

wherein $R^2$, $R^1$ and $(R^6)_m$ are any one of combinations shown below.

A compound represented by the formula (I-33):

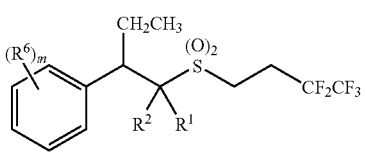
(I-33)

wherein $R^2$, $R^1$ and $(R^6)_m$ are any one of combinations shown below.

A compound represented by the formula (I-34):

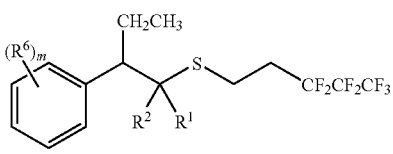
(I-34)

wherein $R^2$, $R^1$ and $(R^6)_m$ are any one of combinations shown below.

A compound represented by the formula (I-35):

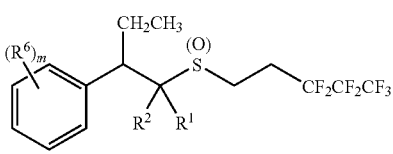
(I-35)

wherein $R^2$, $R^1$ and $(R^6)_m$ are any one of combinations shown below.

A compound represented by the formula (I-36):

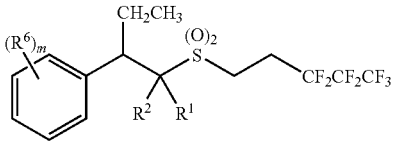
(I-36)

wherein $R^2$, $R^1$ and $(R^6)_m$ are any one of combinations shown below.

A compound represented by the formula (I-37):

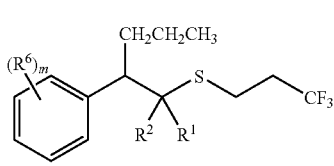
(I-37)

wherein $R^2$, $R^1$ and $(R^6)_m$ are any one of combinations shown below.

A compound represented by the formula (I-38):

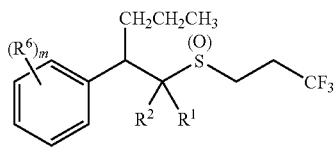

(I-38)

wherein $R^2$, $R^1$ and $(R^6)_m$ are any one of combinations shown below.

A compound represented by the formula (I-39):

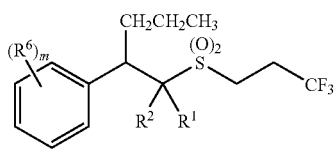

(I-39)

wherein $R^2$, $R^1$ and $(R^6)_m$ are any one of combinations shown below.

A compound represented by the formula (I-40):

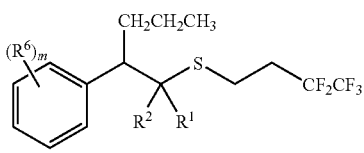

(I-40)

wherein $R^2$, $R^1$ and $(R^6)_m$ are any one of combinations shown below.

A compound represented by the formula (I-41):

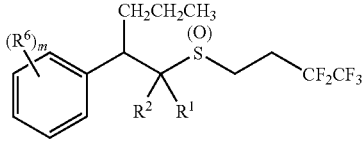

(I-41)

wherein $R^2$, $R^1$ and $(R^6)_m$ are any one of combinations shown below.

A compound represented by the formula (I-42):

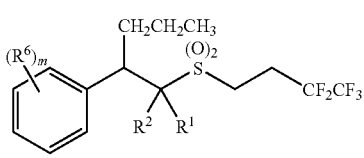

(I-42)

wherein $R^2$, $R^1$ and $(R^6)_m$ are any one of combinations shown below.

A compound represented by the formula (I-43):

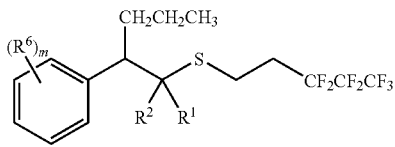

(I-43)

wherein $R^2$, $R^1$ and $(R^6)_m$ are any one of combinations shown below.

A compound represented by the formula (I-44):

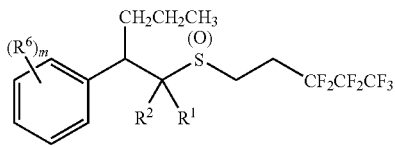

(I-44)

wherein $R^2$, $R^1$ and $(R^6)_m$ are any one of combinations shown below.

A compound represented by the formula (I-45):

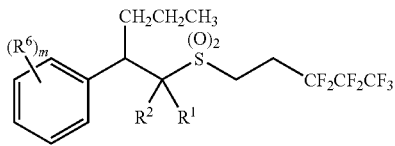

(I-45)

wherein $R^2$, $R^1$ and $(R^6)_m$ are any one of combinations shown below.

A compound represented by the formula (I-46):

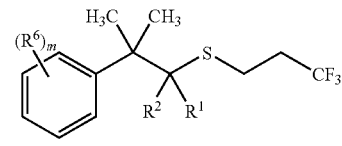

(I-46)

wherein $R^2$, $R^1$ and $(R^6)_m$ are any one of combinations shown below.

A compound represented by the formula (I-47):

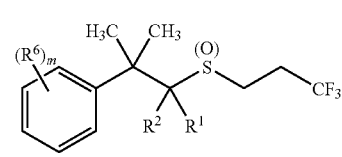

(I-47)

wherein $R^2$, $R^1$ and $(R^6)_m$ are any one of combinations shown below.

A compound represented by the formula (I-48):

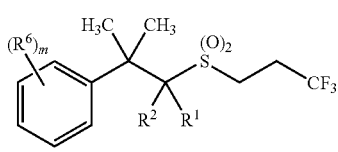

(I-48)

wherein $R^2$, $R^1$ and $(R^6)_m$ are any one of combinations shown below.

A compound represented by the formula (I-49):

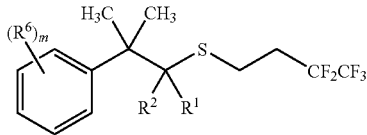

(I-49)

wherein $R^2$, $R^1$ and $(R^6)_m$ are any one of combinations shown below.

A compound represented by the formula (I-50):

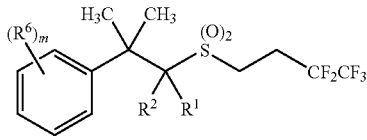

(I-50)

wherein $R^2$, $R^1$ and $(R^6)_m$ are any one of combinations shown below.

A compound represented by the formula (I-51):

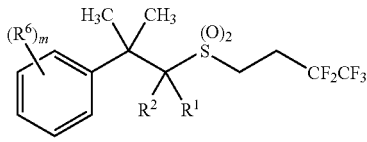

(I-51)

wherein $R^2$, $R^1$ and $(R^6)_m$ are any one of combinations shown below.

A compound represented by the formula (I-52):

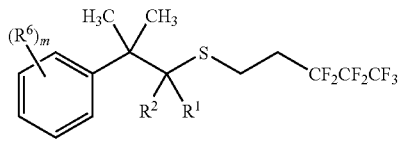

(I-52)

wherein $R^2$, $R^1$ and $(R^6)_m$ are any one of combinations shown below.

A compound represented by the formula (I-53):

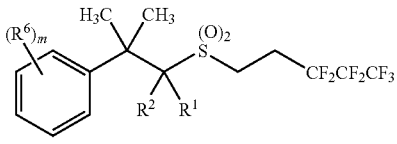

(I-53)

wherein $R^2$, $R^1$ and $(R^6)_m$ are any one of combinations shown below.

A compound represented by the formula (I-54):

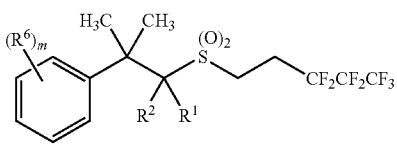

(I-54)

wherein $R^2$, $R^1$ and $(R^6)_m$ are any one of combinations shown below.

Combinations of $R^2$, $R^1$ and $(R^6)_m$ for the compounds represented by the above formulas (I-1)-(I-54) are as follows.
[Combination number: $R^2$; $R^1$; $(R^6)_m$]=[1: H; CONH$_2$; 4-Cl], [2: H; CONH$_2$; 3-Cl], [3: H; CONH$_2$; 4-F], [4: H; CONH$_2$; 4-Br], [5: H; CONH$_2$; 4-I], [6: H; CONH$_2$; 4-CN], [7: H; CONH$_2$; 4-NO$_2$], [8: H; CONH$_2$; 4-CF$_3$], [9: H; CONH$_2$; 3-CF$_3$], [10: H; CONH$_2$; 4-CF$_2$CF$_3$], [11: H; CONH$_2$; 4-C≡CH], [12: H; CONH$_2$; 4-OCF$_3$], [13: H; CONH$_2$; 4-SCF$_3$], [14: H; CONH$_2$; 4-SCH$_3$], [15: H; CONH$_2$; 4-SOCH$_3$], [16: H; CONH$_2$; 4-SO$_2$CH$_3$], [17: H; CONH$_2$; 4-Cl-3-F], [18: H; CONH$_2$; 4-Br-3-F], [19: H; CONH$_2$; 3,4-(Cl)$_2$], [20: H; CONH$_2$; 4-Cl-3-CF$_3$], [21: H; CONH$_2$; 4-F-3-Cl], [22: H; CONH$_2$; 3,4,5-(F)$_3$], [23: H; CONH$_2$; 4-Cl-3,5-(F)$_2$], [24: H; CONHCH$_3$; 4-Cl], [25: H; CONHCH$_3$; 3-Cl], [26: H; CONHCH$_3$; 4-F], [27: H; CONHCH$_3$; 4-Br], [28: H; CONHCH$_3$; 4-I], [29: H; CONHCH$_3$; 4-CN], [30: H; CONHCH$_3$; 4-NO$_2$], [31: H; CONHCH$_3$; 4-CF$_3$], [32: H; CONHCH$_3$; 3-CF$_3$], [33: H; CONHCH$_3$; 4-CF$_2$CF$_3$], [34: H; CONHCH$_3$; 4-C≡CH], [35: H; CONHCH$_3$; 4-OCF$_3$], [36: H; CONHCH$_3$; 4-SCF$_3$], [37: H; CONHCH$_3$; 4-SCH$_3$], [38: H; CONHCH$_3$; 4-SOCH$_3$], [39: H; CONHCH$_3$; 4-SO$_2$CH$_3$], [40: H; CONHCH$_3$; 4-Cl-3-F], [41: H; CONHCH$_3$; 4-Br-3-F], [42: H; CONHCH$_3$; 3,4-(Cl)$_2$], [43: H; CONHCH$_3$; 4-Cl-3-CF$_3$], [44: H; CONHCH$_3$; 4-F-3-Cl], [45: H; CONHCH$_3$; 3,4,5-(F)$_3$], [46: H; CONHCH$_3$; 4-Cl-3,5-(F)$_2$], [47: H; CONHCH$_2$CH$_3$; 4-Cl], [48: H; CONHCH$_2$CH$_3$; 3-Cl], [49: H; CONHCH$_2$CH$_3$; 4-F], [50: H; CONHCH$_2$CH$_3$; 4-Br], [51: H; CONHCH$_2$CH$_3$; 4-I], [52: H; CONHCH$_2$CH$_3$; 4-ON], [53: H; CONHCH$_2$CH$_3$; 4-NO$_2$], [54: H; CONHCH$_2$CH$_3$; 4-CF$_3$], [55: H; CONHCH$_2$CH$_3$; 3-CF$_3$], [56: H; CONHCH$_2$CH$_3$; 4-CF$_2$CF$_3$], [57: H; CONHCH$_2$CH$_3$; 4-C≡CH], [58: H; CONHCH$_2$CH$_3$; 4-00F$_3$], [59: H; CONHCH$_2$CH$_3$; 4-SCF$_3$], [60: H; CONHCH$_2$CH$_3$; 4-SCH$_3$], [61: H; CONHCH$_2$CH$_3$; 4-SOCH$_3$], [62: H; CONHCH$_2$CH$_3$: 4-SO$_2$CH$_3$][63: H; CONHCH$_2$CH$_3$; 4-Cl-3-F], [64: H; CONHCH$_2$CH$_3$; 4-Br-3-F], [65: H; CONHCH$_2$CH$_3$; 3,4-(Cl)$_2$], [66: H; CONHCH$_2$CH$_3$; 4-Cl-3-CF$_3$], [67: H; CONHCH9CH$_3$; 4-F-3-Cl], [68: H; CONHCH$_2$CH$_3$; 3,4,5-(F)$_3$], [69: H; CONHCH$_2$CH$_3$; 4-Cl-3,5-(F)$_2$], [70: H; CON(CH$_3$)$_2$; 4-Cl], [71: H; CON(CH$_3$)$_2$; 3-Cl], [72: H;

CON(CH₃)₂; 4-F], [73: H; CON(CH₃)₂; 4-Br], [74: H; CON(CH₃)₂; 4-I], [75: H; CON(CH₃)₂; 4-CN], [76: H; CON(CH₃)₂; 4-NO₂], [77: H; CON(CH₃)₂; 4-CF₃], [78: H; CON(CH₃)₂; 3-CF₃], [79: H; CON(CH₃)₂; 4-CF₂CF₃], [80: H; CON(CH₃)₂; 4-C≡CH], [81: H; CON(CH₃)₂; 4-OCF₃], [82: H; CON(CH₃)₂; 4-SCF₃], [83: H; CON(CH₃)₂; 4-SCH₃], [84: H; CON(CH₃)₂; 4-SOCH₃], [85: H; CON(CH₃)₂; 4-SO₂CH₃], [86: H; CON(CH₃)₂; 4-Cl-3-F], [87: H; CON(CH₃)₂; 4-Br-3-F], [88: H; CON(CH₃)₂; 3,4-(Cl)₂], [89: H; CON(CH₃)₂; 4-Cl-3-CF₃], [90: H; CON(CH₃)₂; 4-F-3-Cl], [91: H; CON(CH₃)₂; 3,4,5-(F)₃], [92: H; CON(CH₃)₂; 4-Cl-3,5-(F)₂], [93: H; CON(CH₂CH₃)₂; 4-Cl], [94: H; CON(CH₂CH₃)₂; 3-Cl], [95: H; CON(CH₂CH₃)₂; 4-F], [96: H; CON(CH₂CH₃)₂; 4-Br], [97: H; CON(CH₂CH₃)₂; 4-I], [98: H; CON(CH₂CH₃)₂; 4-CN], [99: H; CON(CH₂CH₃)₂; 4-NO₂], [100: H; CON(CH₂CH₃)₂; 4-CF₃], [101: H; CON(CH₂CH₃)₂; 3-CF₃], [102: H; CON(CH₂CH₃)₂; 4-CF₂CF₃], [103: H; CON(CH₂CH₃)₂; 4-C≡CH], [104: H; CON(CH₂CH₃)₂; 4-OCF₃], [105: H; CON(CH₂CH₃)₂; 4-SCF₃], [106: H; CON(CH₂CH₃)₂; 4-SCH₃], [107: H; CON(CH₂CH₃)₂; 4-SOCH₃], [108: H; CON(CH₂CH₃)₂; 4-SO₂CH₃], [109: H; CON(CH₂CH₃)₂; 4-Cl-3-F], [110: H; CON(CH₂CH₃)₂; 4-Br-3-F], [111: H; CON(CH₂CH₃)₂; 3,4-(Cl)₂], [112: H; CON(CH₂CH₃)₂; 4-Cl-3-CF₃], [113: H; CON(CH₂CH₃)₂; 4-F-3-Cl], [114: H; CON(CH₂CH₃)₂; 3,4,5-(F)₃], [115: H; CON(CH₂CH₃)₂; 4-Cl-3,5-(F)₂], [116: H; CSNH₂; 4-Cl], [117: H; CSNH₂; 3-Cl], [118: H; CSNH₂; 4-F], [119: H; CSNH₂; 4-Br], [120: H; CSNH₂; 4-I], [121: H; CSNH₂; 4-CN], [122: H; CSNH₂; 4-NO₂], [123: H; CSNH₂; 4-CF₃], [124: H; CSNH₂; 3-CF₃], [125: H; CSNH₂; 4-CF₂CF₃], [126: H; CSNH₂; 4-C≡CH], [127: H; CSNH₂; 4-OCF₃], [128: H; CSNH₂; 4-SCF₃], [129: H; CSNH₂; 4-SCH₃], [130: H; CSNH₂; 4-SOCH₃], [131: H; CSNH₂; 4-SO₂CH₃], [132: H; CSNH₂; 4-Cl-3-F], [133: H; CSNH₂; 4-Br-3-F], [134: H; CSNH₂; 3,4-(Cl)₂], [135: H; CSNH₂; 4-Cl-3-CF₃], [136: H; CSNH₂; 4-F-3-Cl], [137: H; CSNH₂; 3,4,5-(F)₃], [138: H; CSNH₂; 4-Cl-3,5-(F)₂], [139: H; CSNHCH₃; 4-Cl], [140: H; CSNHCH₃; 3-Cl], [141: H; CSNHCH₃; 4-F], [142: H; CSNHCH₃; 4-Br], [143: H; CSNHCH₃; 4-I], [144: H; CSNHCH₃; 4-CN], [145: H; CSNHCH₃; 4-NO₂], [146: H; CSNHCH₃; 4-CF₃], [147: H; CSNHCH₃; 3-CF₃], [148: H; CSNHCH₃; 4-CF₂CF₃], [149: H; CSNHCH₃; 4-C≡CH], [150: H; CSNHCH₃; 4-OCF₃], [151: H; CSNHCH₃; 4-SCF₃], [152: H; CSNHCH₃; 4-SCH₃], [153: H; CSNHCH₃; 4-SOCH₃], [154: H; CSNHCH₃; 4-SO₂CH₃], [155: H; CSNHCH₃; 4-Cl-3-F], [156: H; CSNHCH₃; 4-Br-3-F], [157: H; CSNHCH₃; 3,4-(Cl)₂], [158: H; CSNHCH₃; 4-Cl-3-CF₃], [159: H; CSNHCH₃; 4-F-3-Cl], [160: H; CSNHCH₃; 3,4,5-(F)₃], [161: H; CSNHCH₃; (F)₂], [162: H; CSNHCH₂CH₃; 4-Cl], [163: H; CSNHCH₂CH₃; 3-Cl], [164: H; CSNHCH₂CH₃; 4-F], [165: H; CSNHCH₂CH₃; 4-Br], [166: H; CSNHCH₂CH₃; 4-I], [167: H; CSNHCH₂CH₃; 4-CN], [168: H; CSNHCH₂CH₃; 4-NO₂], [169: H; CSNHCH₂CH₃; 4-CF₃], [170: H; CSNHCH₂CH₃; 3-CF₃], [171: H; CSNHCH₂CH₃; 4-CF₂CF₃], [172: H; CSNHCH₂CH₃; 4-C≡CH], [173: H; CSNHCH₂CH₃; 4-OCF₃], [174: H; CSNHCH₂CH₃; 4-SCF₃], [175: H; CSNHCH₂CH₃; 4-SCH₃], [176: H; CSNHCH₂CH₃; 4-SOCH₃], [177: H; CSNHCH₂CH₃; 4-SO₂CH₃], [178: H; CSNHCH₂CH₃; 4-Br-3-F], [179: H; CSNHCH₂CH₃; 4-Br-3-F], [180: H; CSNHCH₂CH₃; 3,4-(Cl)₂], [181: H; CSNHCH₂CH₃; 4-Cl-3-CF₃], [182: H; CSNHCH₂CH₃; 4-F3-Cl], [183: H; CSNHCH₂CH₃; 3,4,5-(F)₃], [184: H; CSNHCH₂CH₃; 4-Cl-3,5-(F)₂], [185: H; CSN(CH₃)₂; 4-Cl], [186: H; CSN(CH₃)₂; 3-Cl], [187: H; CSN(CH₃)₂; 4-F], [188: H; CSN(CH₃)₂; 4-Br], [189: H; CSN(CH₃)₂; 4-I], [190: H; CSN(CH₃)₂; 4-CN], [191: H; CSN(CH₃)₂; 4-NO₂], [192: H; CSN(CH₃)₂; 4-CF₃], [193: H; CSN(CH₃)₂; 3-CF₃], [194: H; CSN(CH₃)₂; 4-CF₂CF₃], [195: H; CSN(CH₃)₂; 4-C≡CH], [196: H; CSN(CH₃)₂; 4-OCF₃], [197: H; CSN(CH₃)₂; 4-SOF₃], [198: H; CSN(CH₃)₂; 4-SCH₃], [199: H; CSN(CH₃)₂; 4-SOCH₃], [200: H; CSN(CH₃)₂; 4-SO₂CH₃], [201: H; CSN(CH₃)₂; 4-Cl-3-F], [202: H; CSN(CH₃)₂; 4-Br-3-F], [203: H; CSN(CH₃)₂; 3,4-(Cl)₂], [204: H; CSN(CH₃)₂; 4-Cl-3-CF₃], [205: H; CSN(CH₃)₂; 4-F-3-Cl], [206: H; CSN(CH₃)₂; 3,4,5-(F)₃], [207: H; CSN(CH₃)₂; 4-Cl-3,5-(F)₂], [208: H; CSN(CH₂CH₃)₂; 4-Cl]; [209: H; CSN(CH₂CH₃)₂; 3-Cl], [210: H; CSN(CH₂CH₃)₂; 4-F], [211: H; CSN(CH₂CH₃)₂; 4-Br], [212: H; CSN(CH₂CH₃)₂; 4-I], [213: H; CSN(CH₂CH₃)₂; 4-CN], [214: H; CSN(CH₂CH₃)₂; 4-NO₂], [215: H; CSN(CH₂CH₃)₂; 4-CF₃], [216: H; CSN(CH₂CH₃)₂; 3-CF₃], [217: H; CSN(CH₂CH₃)₂; 4-CF₂CF₃], [218: H; CSN(CH₂CH₃)₂; 4-C≡CH], [219: H; CSN(CH₂CH₃)₂; 4-OCF₃], [220: H; CSN(CH₂CH₃)₂; 4-SCF₃], [221: H; CSN(CH₂CH₃)₂; 4-SCH₃], [222: H; CSN(CH₂CH₃)₂; 4-SOCH₃], [223: H; CSN(CH₂CH₃)₂; 4-SO₂CH₃], [224: H; CSN(CH₂CH₃)₂4-Cl-3-F], [225: H; CSN(CH₂CH₃)₂; 4-Br-3-F], [226: H; CSN(CH₂CH₃)₂; 3,4-(Cl)₂-], [227: H; CSN(CH₂CH₃)₂; 4-Cl-3-CF₃], [228: H; CSN(CH₂CH₃)₂; 4-F-3-Cl], [229: H; CSN(CH₂CH₃)₂; 3,4,5-(F)₃], [230: H; CSN(CH₂CH₃)₂; 4-Cl-3,5-(F)₂], [231: F; CONH₂; 4-Cl], [232: F; CONH₂; 3-Cl], [233: F; CONH₂; 4-F], [234: F; CONH₂; 4-Br], [235: F; CONH₂; 4-I], [236: F; CONH₂; 4-CN], [237: F; CONH₂; 4-NO₂], [238: F; CONH₂; 4-CF₃], [239: F; CONH₂; 3-CF₃], [240: F; CONH₂; 4-CF₂CF₃], [241: F; CONH₂; 4-C≡CH], [242: F; CONH₂; 4-OCF₃], [243: F; CONH₂; 4-SCF₃], [244: F; CONH₂; 4-SCH₃], [245: F; CONH₂; 4-SOCH₃], [246: F; CONH₂; 4-SO₂CH₃], [247: F; CONH₂; 4-Cl-3-F], [248: F; CONH₂; 4-Br-3-F], [249: F; CONH₂; 3,4-(Cl)₂], [250: F; CONH₂; 4-Cl-3-CF₃], [251: F; CONH₂; 4-F-3-Cl], [252: F; CONH₂; 3,4,5-(F)₃], [253: F; CONH₂; 4-Cl-3,5-(F)₂], [254: F; CONHCH₃; 4-Cl], [255: F; CONHCH₃; 3-Cl], [256: F; CONHCH₃; 4-F], [257: F; CONHCH₃; 4-Br], [258: F; CONHCH₃; 4-I], [259: F; CONHCH₃; 4-CN], [260: F; CONHCH₃; 4-NO₂], [261: F; CONHCH₃; 4-CF₃], [262: F; CONHCH₃; 3-CF₃], [263: F; CONHCH₃; 4-CF₂CF₃], [264: F; CONHCH₃; 4-C≡CH], [265: F; CONHCH₃; 4-OCF₃], [266: F; CONHCH₃; 4-SCF₃], [267: F; CONHCH₃; 4-SCH₃], [268: F; CONHCH₃; 4-SOCH₃], [269: F; CONHCH₃; 4-SO₂CH₃], [270: F; CONHCH₃; 4-Cl-3-F], [271: F; CONHCH₃; 4-Br-3-F], [272: F; CONHCH₃; 3,4-(Cl)₂], [273: F; CONHCH₃; 4-Cl-3-CF₃], [274: F; CONHCH₃; 4-F-3-Cl], [275: F; CONHCH₃; 3,4,5-(F)₃], [276: F; CONHCH₃; 4-Cl-3,5-(F)₂], [277: F; CONHCH₂CH₃; 4-Cl], [278: F; CONHCH₂CH₃; 3-Cl], [279: F; CONHCH₂CH₃; 4-F], [280: F; CONHCH₂CH₃; 4-Br], [281: F; CONHCH₂CH₃; 4-I], [282: F; CONHCH₂CH₃; 4-CN], [283: F; CONHCH₂CH₃; 4-NO₂], [284: F; CONHCH₂CH₃; 4-CF₃], [285: F; CONHCH₂CH₃; 3-CF₃], [286: F; CONHCH₂CH₃; 4-CF₂CF₃], [287: F; CONHCH₂CH₃; 4-C≡CH], [288: F; CONHCH₂CH₃; 4-OCF₃], [289: F; CONHCH₂CH₃; 4-SCF₃], [290: F; CONHCH₂CH₃; 4-SCH₃], [291: F; CONHCH₂CH₃; 4-SOCH₃], [292: F; CONHCH₂CH₃; 4-SO₂CH₃], [293: F; CONHCH₂CH₃; 4-Cl-3-F], [294: F; CONHCH₂CH₃; 4-Br-3-F], [295: F; CONHCH₂CH₃; 3,4-(Cl)₂], [296: F; CONHCH₂CH₃; 4-Cl-3-CF₃], [297: F; CONHCH₂CH₃; 4-F-3-Cl], [298: F; CONHCH₂CH₃; 3,4,5-(F)₃], [299: F; CONHCH₂CH₃; 4-Cl-3,5-(F)₂], [300: F; CON(CH₃)₂; 4-Cl], [301: F; CON(CH₃)₂: 3-Cl], [302: F;

CON(CH$_3$)$_2$: 4-F], [303: F; CON(CH$_3$)$_2$: 4-Br], [304: F; CON(CH$_3$)$_2$; 4-I], [305: F; CON(CH$_3$)$_2$; 4-CN], [306: F; CON(CH$_3$)$_2$; 4-NO$_2$], [307: F; CON(CH$_3$)$_2$; 4-CF$_3$], [308: F; CON(CH$_3$)$_2$; 3-CF$_3$], [309: F; CON(CH$_3$)$_2$; 4-CF$_2$CF$_3$], [310: F; CON(CH$_3$)$_2$; 4-C≡CH], [311: F; CON(CH$_3$)$_2$; 4-OCF$_3$], [312: F; CON(CH$_3$)$_2$; 4-SCF$_3$], [313: F; CON(CH$_3$)$_2$; 4-SCH$_3$], [314: F; CON(CH$_3$)$_2$; 4-SOCH$_3$], [315: F; CON(CH$_3$)$_2$; 4-SO$_2$CH$_3$], [316: F; CON(CH$_3$)$_2$; 4-Cl-3-F], [317: F; CON(CH$_3$)$_2$; 4-Br-3-F], [318: F; CON(CH$_3$)$_2$; 3,4-(Cl)$_2$], [319: F; CON(CH$_3$)$_2$; 4-Cl-3-CF$_3$], [320: F; CON(CH$_3$)$_2$; 4-F-3-Cl], [321: F; CON(CH$_3$)$_2$; 3,4,5-(F)$_3$], [322: F; CON(CH$_3$)$_2$; 4-Cl-3,5-(F)$_2$], [323: F; CON(CH$_2$CH$_3$)$_2$; 4-Cl], [324: F; CON(CH$_2$CH$_3$)$_2$; 3-Cl], [325: F; CON(CH$_2$CH$_3$)$_2$; 4-F], [326: F; CON(CH$_2$CH$_3$)$_2$; 4-Br], [327: F; CON(CH$_2$CH$_3$)$_2$; 4-I], [328: F; CON(CH$_2$CH$_3$)$_2$; 4-CN], [329: F; CON(CH$_2$CH$_3$)$_2$; 4-NO$_2$], [330: F; CON(CH$_2$CH$_3$)$_2$; 4-CF$_3$], [331: F; CON(CH$_2$CH$_3$)$_2$; 3-CF$_3$], [332: F; CON(CH$_2$CH$_3$)$_2$; 4-CF$_2$CF$_3$], [333: F; CON(CH$_2$CH$_3$)$_2$; 4-C≡CH], [334: F; CON(CH$_2$CH$_3$)$_2$; 4-OCF$_3$], [335: F; CON(CH$_2$CH$_3$)$_2$; 4-SCF$_3$], [336: F; CON(CH$_2$CH$_3$)$_2$; 4-SCH$_3$], [337: F; CON(CH$_2$CH$_3$)$_2$; 4-SOCH$_3$], [338: F; CON(CH$_2$CH$_3$)$_2$4-SO$_2$CH$_3$], [339: F; CON(CH$_2$CH$_3$)$_2$; 4-Cl-3-F], [340: F; CON(CH$_2$CH$_3$)$_2$; 4-Br-3-F], [341: F; CON(CH$_2$CH$_3$)$_2$; 3,4-(Cl)$_2$], [342: F; CON(CH$_2$CH$_3$)$_2$; 4-Cl-3-CF$_3$], [343: F; CON(CH$_2$CH$_3$)$_2$; 4-F-3-Cl], [344: F; CON(CH$_2$CH$_3$)$_2$; 3,4,5-(F)$_3$], [345: F; CON(CH$_2$CH$_3$)$_2$; 4-Cl-3,5-(F)$_2$], [346: F; CSNH$_2$; 4-Cl], [347: F; CSNH$_2$; 3-Cl], [348: F; CSNH$_2$; 4-F], [349: F; CSNH$_2$; 4-Br], [350: F; CSNH$_2$; 4-I], [351: F; CSNH$_2$; 4-CN], [352: F; CSNH$_2$; 4-NO$_2$], [353: F; CSNE$_2$; 4-CF$_3$], [354: F; CSNH$_2$; 3-CF$_3$], [355: F; CSNH$_2$; 4-CF$_2$CF$_3$], [356: F; CSNH$_2$; 4-C≡CH], [357: F; CSNH$_2$; 4-OCF$_3$], [358: F; CSNH$_2$; 4-SCF$_3$], [359: F; CSNH$_2$; 4-SCH$_3$], [360: F; CSNH$_2$; 4-SOCH$_3$], [361: F; CSNH$_2$; 4-SO$_2$CH$_3$], [362: F; CSNH$_2$; 4-Cl-3-F], [363: F; CSNH$_2$; 4-Br-3-F], [364: F; CSNH$_2$; 3,4-(Cl)$_2$], [365: F; CSNH$_2$; 4-Cl-3-CF$_3$], [366: F; CSNH$_2$; 4-F-3-Cl], [367: F; CSNH$_2$; 3,4,5-(F)$_3$], [368: F; CSNH$_2$; 4-Cl-3,5-(F)$_2$], [369: F; CSNHCH$_3$; 4-Cl], [370: F; CSNHCH$_3$; 3-Cl], [371: F; CSNHCH$_3$; 4-F], [372: F; CSNHCH$_3$; 4-Br], [373: F; CSNHCH$_3$; 4-I], [374: F; CSNHCH$_3$; 4-CN], [375: F; CSNHCH$_3$; 4-NO$_2$],[376: F; CSNHCH$_3$; 4-CF$_3$], [377: F; CSNHCH$_3$; 3-CF$_3$], [378: F; CSNHCH$_3$; 4-CF$_2$CF$_3$], [379: F; CSNHCH$_3$; 4-C≡CH], [380: F; CSNHCH$_3$; 4-OCF$_3$], [381: F; CSNHCH$_3$; 4-SCF$_3$], [382: F; CSNHCH$_3$; 4-SCH$_3$], [383: F; CSNHCH$_3$; 4-SOCH$_3$], [384: F; CSNHCH$_3$; 4-SO$_2$CH$_3$], [385: F; CSNHCH$_3$; 4-Cl-3-F], [386: F; CSNHCH$_3$; 4-Br-3-F], [387: F; CSNHCH$_3$; 3,4-(Cl)$_2$], [388: F; CSNHCH$_3$; 4-Cl-3-CF$_3$], [389: F; CSNHCH$_3$; 4-F-3-Cl], [390: F; CSNHCH$_3$; 3,4,5-(F)$_3$], [391: F; CSNHCH$_3$; 4-Cl-3,5-(F)$_2$], [392: F; CSNHCH$_2$CH$_3$; 4-Cl], [393: F; CSNHCH$_2$CH$_3$; 3-Cl], [394: F; CSNHCH$_2$CH$_3$; 4-F], [395: F; CSNHCH$_2$CH$_3$; 4-Br], [396: F; CSNHCH$_2$CH$_3$: 4-I], [397: F; CSNHCH$_2$CH$_3$; 4-CN], [398: F; CSNHCH$_2$CH$_3$; 4-NO$_2$], [399: F; CSNHCH$_2$CH$_3$; 4-CF$_3$], [400: F; CSNHCH$_2$CH$_3$; 3-CF$_3$], [401: F; CSNHCH$_2$CH$_3$; 4-CF$_2$CF$_3$], [402: F; CSNHCH$_2$CH$_3$; 4-C≡CH], [403: F; CSNHCH$_2$CH$_3$; 4-OCF$_3$], [404: F; CSNHCH$_2$CH$_3$; 4-SCF$_3$], [405: F; CSNHCH$_2$CH$_3$; 4-SCH$_3$], [406: F; CSNHCH$_2$CH$_3$; 4-SOCH$_3$], [407: F; CSNHCH$_2$CH$_3$; 4-SO$_2$CH$_3$], [408: F; CSNHCH$_2$CH$_3$; 4-Cl-3-F], [409: F; CSNHCH$_2$CH$_3$; 4-Br-3-F], [412: F; CSNHCH$_2$CH$_3$; 4-F-3-Cl], [411: F; CSNHCH$_2$CH$_3$; 4-Cl-3-CF$_3$], [412: F; CSNHCH$_2$CH$_3$; 3,4,5-(F)$_3$], [413: F; CSNHCH$_2$CH$_3$; 4-Cl-3,5-(F)$_2$], [414: F; CSN(CH$_3$)$_2$; 4-Cl], [415: F; CSN(CH$_3$)$_2$; 3-Cl], [416: F; CSN(CH$_3$)$_2$; 4-F], [418: F; CSN(CH$_3$)$_2$; 4-Br], [419: F; CSN(CH$_3$)$_2$: 4-I], [420: F; CSN(CH$_3$)$_2$; 4-CN], [421: F; CSN(CH$_3$)$_2$; 4-NO$_2$], [422: F; CSN(CH$_3$)$_2$; 4-CF$_3$], [423: F; CSN(CH$_3$)$_2$; 3-CF$_3$], [424: F; CSN(CH$_3$)$_2$; 4-CF$_2$CF$_3$], [425: F; CSN(CH$_3$)$_2$; 4-C≡CH], [426: F; CSN(CH$_3$)$_2$; 4-OCF$_3$], [427: F; CSN(CH$_3$)$_2$; 4-SCF$_3$], [428: F; CSN(CH$_3$)$_2$; 4-SCH$_3$], [429: F; CSN(CH$_3$)$_2$; 4-SOCH$_3$], [430: F; CSN(CH$_3$)$_2$; 4-SO$_2$CH$_3$], [431: F; CSN(CH$_3$)$_2$; 4-Cl-3-F], [432: F; CSN(CH$_3$)$_2$; 4-Br-3-F], [433: F; CSN(CH$_3$)$_2$; 3,4-(Cl)$_2$], [434: F; CSN(CH$_3$)$_2$; 4-Cl-3-CF$_3$], [435: F; CSN(CH$_3$)$_2$; 4-F-3-Cl], [436: F; CSN(CH$_3$)$_2$; 3,4,5-(F)$_3$], [437: F; CSN(CH$_3$)$_2$; 4-Cl-3,5-(F)$_2$], [438: F; CSN(CH$_2$CH$_3$)$_2$; 4-Cl], [439: F; CSN(CH$_2$CH$_3$)$_2$; 3-Cl], [440: F; CSN(CH$_2$CH$_3$)$_2$; 4-F], [441: F; CSN(CH$_2$CH$_3$)$_2$; 4-Br], [442: F; CSN(CH$_2$CH$_3$)$_2$; 4-I], [443: F; CSN(CH$_2$CH$_3$)$_2$; 4-CN], [444: F; CSN(CH$_2$CH$_3$)$_2$; 4-NO$_2$], [445: F; CSN(CH$_2$CH$_3$)$_2$; 4-CF$_3$], [446: F; CSN(CH$_2$CH$_3$)$_2$; 3-CF$_3$], [447: F; CSN(CH$_2$CH$_3$)$_2$; 4CF$_2$CF$_3$], [448: F; CSN(CH$_2$CH$_3$)$_2$; 4-C≡CH], [449: F; CSN(CH$_2$CH$_3$)$_2$; 4-OCF$_3$], [450: F; CSN(CH$_2$CH$_3$)$_2$; 4-SCF$_3$], [451: F; CSN(CH$_2$CH$_3$)$_2$; 4-SCH$_3$], [452: F; CSN(CH$_2$CH$_3$)$_2$; 4-SOCH$_3$], [453: F; CSN(CH$_2$CH$_3$)$_2$; 4-SO$_2$OH$_3$], [454: F; CSN(CH$_2$CH$_3$)$_2$; 4-Cl-3-F], [455: F; CSN(CH$_2$CH$_3$)$_2$; 4-Br-3-F], [456: F; CSN(CH$_2$CH$_3$)$_2$; 3,4-(Cl)$_2$], [457: F; CSN(CH$_2$CH$_3$)$_2$; 4-Cl-3-CF$_3$], [458: F; CSN(CH$_2$CH$_3$)$_2$; 4-F-3-Cl], [459: F; CSN(CH$_2$CH$_3$)$_2$; 3,4,5-(F)$_3$], [460: F; CSN(CH$_2$CH$_3$)$_2$; 4-Cl-3,5-(F)$_2$], [461: Cl; CONH$_2$; 4-Cl], [462: Cl; CONH$_2$; 3-Cl], [463: Cl; CONH$_2$; 4-F], [464: Cl; CONH$_2$; 4-Br], [465: Cl; CONH$_2$; 4-I], [466: Cl; CONH$_2$; 4-CN], [467: Cl; CONH$_2$; 4-NO$_2$], [468: Cl; CONH$_2$; 4-CF$_3$], [469: Cl; CONH$_2$; 3-CF$_3$], [470: Cl; CONH$_2$; 4-CF$_2$CF$_3$], [471: Cl; CONH$_2$; 4-C≡CH], [472: Cl; CONH$_2$; 4-OCF$_3$], [473: Cl; CONH$_2$; 4-SCF$_3$], [474: Cl; CONH$_2$; 4-SCH$_3$], [475: Cl; CONH$_2$; 4-SOCH$_3$], [476: Cl; CONH$_2$; 4-SO$_2$CH$_3$], [477: Cl; CONH$_2$; 4-Cl-3-F], [478: Cl; CONH$_2$; 4-Br-3-F], [479: Cl; CONH$_2$; 3,4-(Cl)$_2$], [480: Cl; CONH$_2$; 4-Cl-3-CF$_3$], [481: Cl; CONH$_2$; 4-F-3-Cl], [482: Cl; CONH$_2$; 3,4,5-(F)$_3$], [483: Cl; CONH$_2$; 4-Cl-3,5-(F)$_2$], [484: Cl; CONHCH$_3$; 4-Cl], [485: Cl; CONHCH$_3$; 3-Cl], [486: Cl; CONHCH$_3$; 4-F], [487: Cl; CONHCH$_3$; 4-Br], [488: Cl; CONHCH$_3$; 4-I], [489: Cl; CONHCH$_3$; 4-CN], [490: Cl; CONHCH$_3$; 4-NO$_2$], [491: Cl; CONHCH$_3$; 4-CF$_3$], [492: Cl; CONHCH$_3$; 3-CF$_3$], [493: Cl; CONHCH$_3$; 4-CF$_2$CF$_3$], [494: Cl; CONHCH$_3$; 4-C≡CH], [495: Cl; CONHCH$_3$; 4-OCF$_3$], [496: Cl; CONHCH$_3$; 4-SCF$_3$], [497: Cl; CONHCH$_3$; 4-SCH$_3$], [498: Cl; CONHCH$_3$; 4-SOCH$_3$], [499: Cl; CONHCH$_3$; 4-SO$_2$CH$_3$], [500: Cl; CONHCH$_3$; 4-Cl-3-F], [501: Cl; CONHCH$_3$; 4-Br-3-F], [502: Cl; CONHCH$_3$; 3,4-(Cl)$_2$], [503: Cl; CONHCH$_3$; 4-Cl-3-CF$_3$], [504: Cl; CONHCH$_3$; 4-F-3-Cl], [505: Cl; CONHCH$_3$; 3,4,5-(F)$_3$], [506: Cl; CONHCH$_3$; 4-Cl-3,5-(F)$_2$], [507: Cl; CONHCH$_2$CH$_3$; 4-Cl], [508: Cl; CONHCH$_2$CH$_3$; 3-Cl], [509: Cl; CONHCH$_2$CH$_3$; 4-F], [510: Cl; CONHCH$_2$CH$_3$; 4-Br], [511: Cl; CONHCH$_2$CH$_3$; 4-I], [512: Cl; CONHCH$_2$CH$_3$; 4-CN], [513: Cl; CONHCH$_2$CH$_3$; 4-NO$_2$], [514: Cl; CONHCH$_2$CH$_3$; 4-CF$_3$], [515: Cl; CONHCH$_2$CH$_3$; 3-CF$_3$], [516: Cl; CONHCH$_2$CH$_3$; 4-CF$_2$CF$_3$], [517: Cl; CONHCH$_2$CH$_3$; 4-C≡CH], [518: Cl; CONHCH$_2$CH$_3$; 4-OCF$_3$], [519: Cl; CONHCH$_2$CH$_3$; 4-SCF$_3$], [520: Cl; CONHCH$_2$CH$_3$; 4-SCH$_3$], [521: Cl; CONHCH$_2$CH$_3$; 4-SOCH$_3$], [522: Cl; CONHCH$_2$CH$_3$; 4-SO$_2$CH$_3$], [523: Cl; CONHCH$_2$CH$_3$; 4-Cl-3-F], [524: Cl; CONHCH$_2$CH$_3$; 4-Br-3-F], [525: Cl; CONHCH$_2$CH$_3$; 3,4-(Cl)$_2$], [526: Cl; CONHCH$_2$CH$_3$; 4-Cl-3-CF$_3$], [527: Cl; CONHCH$_2$CH$_3$; 4-F-3-Cl], [528: Cl; CONHCH$_2$CH$_3$; 3,4,5-(F)$_3$], [529: Cl; CONHCH$_2$CH$_3$; 4-Cl-3,5-(F)$_2$], [530: Cl; CON(CH$_3$)$_2$;

4-Cl], [531: Cl; CON(CH$_3$)$_2$; 3-Cl], [532: Cl; CON(CH$_3$)$_2$; 4-F], [533: Cl; CON(CH$_3$)$_2$; 4-Br], [534: Cl; CON(CH$_3$)$_2$; 4-I], [535: Cl; CON(CH$_3$)$_2$; 4-CN], [536: Cl; CON(CH$_3$)$_2$; 4-NO$_2$], [537: Cl; CON(CH$_3$)$_2$; 4-CF$_3$], [538: Cl; CON(CH$_3$)$_2$; 3-CF$_3$], [539: Cl; CON(CH$_3$)$_2$; 4-CF$_2$CF$_3$], [540: Cl; CON(CH$_3$)$_2$; 4-C≡CH], [541: Cl; CON(CH$_3$)$_2$; 4-OCF$_3$], [542: Cl; CON(CH$_3$)$_2$; 4-SCF$_3$], [543: Cl; CON(CH$_3$)$_2$; 4-SCH$_3$], [544: Cl; CON(CH$_3$)$_2$; 4-SOCH$_3$], [545: Cl; CON(CH$_3$)$_2$; 4-SO$_2$CH$_3$], [546: Cl; CON(CH$_3$)$_2$; 4-Cl-3-F], [547: Cl; CON(CH$_3$)$_2$; 4-Br-3-F], [548: Cl; CON(CH$_3$)$_2$; 3,4-(Cl)$_2$], [549: Cl; CON(CH$_3$)$_2$; 4-Cl-3-CF$_3$], [550: Cl; CON(CH$_3$)$_2$; 4-F-3-Cl], [551: Cl; CON(CH$_3$)$_2$; 3,4,5-(F)$_3$], [552: Cl; CON(CH$_3$)$_2$; 4-Cl-3,5-(F)$_2$], [553: Cl; CON(CH$_2$CH$_3$)$_2$; 4-Cl], [554: Cl; CON(CH$_2$CH$_3$)$_2$; 3-Cl], [555: Cl; CON(CH$_2$CH$_3$)$_2$; 4-F], [556: Cl; CON(CH$_2$CH$_3$)$_2$; 4-Br], [557: Cl; CON(CH$_2$CH$_3$)$_2$; 4-I], [558: Cl; CON(CH$_2$CH$_3$)$_2$; 4-CN], [559: Cl; CON(CH$_2$CH$_3$)$_2$; 4-NO$_2$], [560: Cl; CON(CH$_2$CH$_3$)$_2$; 4-CF$_3$], [561: Cl; CON(CH$_2$CH$_3$)$_2$; 3-CF$_3$], [562: Cl; CON(CH$_2$CH$_3$)$_2$; 4-CF$_2$CF$_3$], [563: Cl; CON(CH$_2$CH$_3$)$_2$; 4-C≡CH], [564: Cl; CON(CH$_2$CH$_3$)$_2$; 4-OCF$_3$], [565: Cl; CON(CH$_2$CH$_3$)$_2$; 4-SCF$_3$], [566: Cl; CON(CH$_2$CH$_3$)$_2$; 4-SCH$_3$], [567: Cl; CON(CH$_2$CH$_3$)$_2$; 4-SOCH$_3$], [568: Cl; CON(CH$_2$CH$_3$)$_2$; 4-SO$_2$CH$_3$], [569: Cl; CON(CH$_2$CH$_3$)$_2$; 4-Cl-3-F], [570: Cl; CON(CH$_2$CH$_3$)$_2$; 4-Br-3-F], [571: Cl; CON(CH$_2$CH$_3$)$_2$; 3,4-(Cl)$_2$], [572: Cl; CON(CH$_2$CH$_3$)$_2$; 4Cl-3-CF$_3$], [573: Cl; CON(CH$_2$CH$_3$)$_2$; 4-F-3-Cl], [574: Cl; CON(CH$_2$CH$_3$)$_2$; 3,4,5-(F)$_3$], [575: Cl; CON(CH$_2$CH$_3$)$_2$; 4-Cl-3,5-(F)$_2$], [576: Cl; CSNH$_2$; 4-Cl], [577: Cl; CSNH$_2$; 3-Cl], [578: Cl; CSNH$_2$; 4-F], [579: Cl; CSNH$_2$; 4-Br], [580: Cl; CSNH$_2$; 4-I], [581: Cl; CSNH$_2$; 4-CN], [582: Cl; CSNH$_2$; 4-NO$_2$], [583: Cl; CSNH$_2$; 4-CF$_3$], [584: Cl; CSNH$_2$; 3-CF$_3$], [585: Cl; CSNH$_2$; 4-CF$_2$CF$_3$], [586: Cl; CSNH$_2$; 4-C≡CH], [587: Cl; CSNH$_2$; 4-OCF$_3$], [588: Cl; CSNH$_2$; 4-SCF$_3$], [589: Cl; CSNH$_2$; 4-SCH$_3$], [590: Cl; CSNH$_2$; 4-SOCH$_3$], [591: Cl; CSNH$_2$; 4-SO$_2$CH$_3$], [592: Cl; CSNH$_2$; 4-Cl-3-F], [593: Cl; CSNH$_2$; 4-Br-3-F], [594: Cl; CSNH$_2$; 3,4-(Cl)$_2$], [595: Cl; CSNH$_2$; 4-Cl-3-CF$_3$], [596: Cl; CSNH$_2$; 4-F-3-Cl], [597: Cl; CSNH$_2$; 3,4,5-(F)$_3$], [598: Cl; CSNH$_2$; 4-Cl-3,5-(F)$_2$], [599: Cl; CSNHCH$_3$; 4-Cl], [600: Cl; CSNHCH$_3$; 3-Cl], [601: Cl; CSNHCH$_3$; 4-F], [602: Cl; CSNHCH$_3$; 4-Br], [603: Cl; CSNHCH$_3$; 4-I], [604: Cl; CSNHCH$_3$; 4-CN], [605: Cl; CSNHCH$_3$; 4-NO$_2$], [606: Cl; CSNHCH$_3$; 4-CF$_3$], [607: Cl; CSNHCH$_3$; 3-CF$_3$], [608: Cl; CSNHCH$_3$; 4-CF$_2$CF$_3$], [609: Cl; CSNHCH$_3$; 4-C≡CH], [610: Cl; CSNHCH$_3$; 4-OCF$_3$], [611: Cl; CSNHCH$_3$; 4-SCF$_3$], [612: Cl; CSNHCH$_3$; 4-SCH$_3$], [613: Cl; CSNHCH$_3$; 4-SOCH$_3$], [614: Cl; CSNHCH$_3$; 4-SO$_2$CH$_3$], [615: Cl; CSNHCH$_3$; 4-Cl-3-F], [616: Cl; CSNHCH$_3$; 4-Br-3-F], [617: Cl; CSNHCH$_3$; 3,4-(Cl)$_2$], [618: Cl; CSNHCH$_3$; 4-Cl-3-CF$_3$], [619: Cl; CSNHCH$_3$; 4-F-3-Cl], [620: Cl; CSNHCH$_3$; 3,4,5-(F)$_3$], [621: Cl; CSNHCH$_3$; 4-Cl-3,5-(F)$_2$], [622: Cl; CSNHCH$_2$CH$_3$; 4-Cl], [623: Cl; CSNHCH$_2$CH$_3$; 3-Cl], [624: Cl; CSNHCH$_2$CH$_3$; 4-F], [625: Cl; CSNHCH$_2$CH$_3$; 4-Br], [626: Cl; CSNHCH$_2$CH$_3$; 4-I], [627: Cl; CSNHCH$_2$CH$_3$; 4-CN], [628: Cl; CSNHCH$_2$CH$_3$; 4-NO$_2$], [629: Cl; CSNHCH$_2$CH$_3$; 4-CF$_3$], [630: Cl; CSNHCH$_2$CH$_3$; 3-CF$_3$], [631: Cl; CSNHCH$_2$CH$_3$; 4-CF$_2$CF$_3$], [632: Cl; CSNHCH$_2$CH$_3$; 4-C≡CH], [633: Cl; CSNHCH$_2$CH$_3$; 4-OCF$_3$], [634: Cl; CSNHCH$_2$CH$_3$; 4-SCF$_3$], [635: Cl; CSNHCH$_2$CH$_3$; 4-SCH$_3$], [636: Cl; CSNHCH$_2$CH$_3$; 4-SOCH$_3$], [637: Cl; CSNHCH$_2$CH$_3$; 4-SO$_2$CH$_3$], [638: Cl; CSNHCH$_2$CH$_3$; 4-Cl-3-F], [639: Cl; CSNHCH$_2$CH$_3$; 4-Br-3-F], [640: Cl; CSNHCH$_2$CH$_3$; 3,4-(Cl)$_2$], [641: Cl; CSNHCH$_2$CH$_3$; 4-Cl-3-CF$_3$], [642: Cl; CSNHCH$_2$CH$_3$; 4-F-3-Cl], [643: Cl; CSNHCH$_2$CH$_3$; 3,4,5-(F)$_3$], [644: Cl; CSNHCH$_2$CH$_3$; 4-Cl-3,5-(F)$_2$], [645: Cl; CSN(CH$_3$)$_2$; 4-Cl], [646: Cl; CSN(CH$_3$)$_2$; 3-Cl], [647: Cl; CSN(CH$_3$)$_2$; 4-F], [648: Cl; CSN(CH$_3$)$_2$; 4-Br], [649: Cl; CSN(CH$_3$)$_2$; 4-I], [650: Cl; CSN(CH$_3$)$_2$; 4-CN], [651: Cl; CSN(CH$_3$)$_2$; 4-NO$_2$], [652: Cl; CSN(CH$_3$)$_2$; 4-CF$_3$], [653: Cl; CSN(CH$_3$)$_2$; 3-CF$_3$], [654: Cl; CSN(CH$_3$)$_2$; 4-CF$_2$CF$_3$], [655: Cl; CSN(CH$_3$)$_2$; 4-C≡CH], [656: Cl; CSN(CH$_3$)$_2$; 4-OCF$_3$], [657: Cl; CSN(CH$_3$)$_2$; 4-SCF$_3$], [658: Cl; CSN(CH$_3$)$_2$; 4-SCH$_3$], [659: Cl; CSN(CH$_3$)$_2$; 4-SOCH$_3$], [660: Cl; CSN(CH$_3$)$_2$; 4-SO$_2$CH$_3$], [661: Cl; CSN(CH$_3$)$_2$; 4-Cl-3-F], [662: Cl; CSN(CH$_3$)$_2$; 4-Br-3-F], [663: Cl; CSN(CH$_3$)$_2$; 3,4-(Cl)$_2$], [664: Cl; CSN(CH$_3$)$_2$; 4-Cl-3-CF$_3$], [665: Cl; CSN(CH$_3$)$_2$; 4-F-3-Cl], [666: Cl; CSN(CH$_3$)$_2$; 3,4,5-(F)$_3$], [667: Cl; CSN(CH$_3$)$_2$; 4-Cl-3,5-(F)$_2$], [668: Cl; CSN(CH$_2$CH$_3$)$_2$; 4Cl], [669: Cl; CSN(CH$_2$CH$_3$)$_2$; 3-Cl], [670: Cl; CSN(CH$_2$CH$_3$)$_2$; 4-F], [671: Cl; CSN(CH$_2$CH$_3$)$_2$; 4-Br], [672: Cl; CSN(CH$_2$CH$_3$)$_2$; 4-I], [673: Cl; CSN(CH$_2$CH$_3$)$_2$; 4-CN], [674: Cl; CSN(CH$_2$CH$_3$)$_2$; 4-NO$_2$], [675: Cl; CSN(CH$_2$CH$_3$)$_2$; 4-CF$_3$], [676: Cl; CSN(CH$_2$CH$_3$)$_2$; 3CF$_3$], [677: Cl; CSN(CH$_2$CH$_3$)$_2$; 4-CF$_2$CF$_3$], [678: Cl; CSN(CH$_2$CH$_3$)$_2$; 4-C≡CH], [679: Cl; CSN(CH$_2$CH$_3$)$_2$; 4-OCF$_3$], [680: Cl; CSN(CH$_2$CH$_3$)$_2$; 4-SCF$_3$], [681: Cl; CSN(CH$_2$CH$_3$)$_2$; 4-SCH$_3$], [682: Cl; CSN(CH$_2$CH$_3$)$_2$; 4-SOCH$_3$], [683: Cl; CSN(CH$_2$CH$_3$)$_2$; 4-SO$_2$CH$_3$], [684: Cl; CSN(CH$_2$CH$_3$)$_2$; 4-Cl-3-F], [685: Cl; CSN(CH$_2$CH$_3$)$_2$; 4-Br-3-F], [686: Cl; CSN(CH$_2$CH$_3$)$_2$; 3,4-(Cl)$_2$], [687: Cl; CSN(CH$_2$CH$_3$)$_2$; 4-Cl-3-CF$_3$], [688: Cl; CSN(CH$_2$CH$_3$)$_2$; 4-F-3-Cl], [689: Cl; CSN(CH$_2$CH$_3$)$_2$; 3,4,5-(F)$_3$], [690: Cl; CSN(CH$_2$CH$_3$)$_2$; 4-Cl-3,5-(F)$_2$], [691: Br; CONH$_2$; 4-Cl], [692: Br; CONH$_2$; 3-Cl], [693: Br; CONH$_2$; 4-F], [694: Br; CONH$_2$; 4-Br], [695: Br; CONH$_2$; 4-I], [696: Br; CONH$_2$; 4-CN], [697: Br; CONH$_2$; 4-NO$_2$], [698: Br; CONH$_2$; 4-CF$_3$], [699: Br; CONH$_2$; 3-CF$_3$], [700: Br; CONH$_2$; 4-CF$_2$CF$_3$], [701: Br; CONH$_2$; 4-C≡CH], [702: Br; CONH$_2$; 4-OCF$_3$], [703: Br; CONH$_2$; 4-SCF$_3$], [704: Br; CONH$_2$; 4-SCH$_3$], [705: Br; CONH$_2$; 4-SOCH$_3$], [706: Br; CONH$_2$; 4-SO$_2$CH$_3$], [707: Br; CONH$_2$; 4-Cl-3-F], [708: Br; CONH$_2$; 4-Br-3-F], [709: Br; CONH$_2$; 3,4-(Cl)$_2$], [710: Br; CONH$_2$; 4-Cl-3-CF$_3$], [711: Br; CONH$_2$; 4-F-3-Cl], [712: Br; CONH$_2$; 3,4,5-(F)$_3$], [713: Br; CONH$_2$; 4-Cl-3,5-(F)$_2$], [714: Br; CONHCH$_3$; 4-Cl], [715: Br; CONHCH$_3$; 3-Cl], [716: Br; CONHCH$_3$; 4-F], [717: Br; CONHCH$_3$; 4-Br], [718: Br; CONHCH$_3$; 4-I], [719: Br; CONHCH$_3$; 4-CN], [720: Br; CONHCH$_3$; 4-NO$_2$], [721: Br; CONHCH$_3$; 4-CF$_3$], [722: Br; CONHCH$_3$; 3-CF$_3$], [723: Br; CONHCH$_3$; 4-CF$_2$CF$_3$], [724: Br; CONHCH$_3$; 4-C≡CH], [725: Br; CONHCH$_3$; 4-OCF$_3$], [726: Br; CONHCH$_3$; 4-SCF$_3$], [727: Br; CONHCH$_3$; 4-SCH$_3$], [728: Br; CONHCH$_3$; 4-SOCH$_3$], [729: Br; CONHCH$_3$; 4-SO$_2$CH$_3$], [730: Br; CONHCH$_3$; 4-Cl-3-F], [731: Br; CONHCH$_3$; 4-Br-3-F], [732: Br; CONHCH$_3$; 3,4-(Cl)$_2$], [733: Br; CONHCH$_3$; 4-Cl-3-CF$_3$], [734: Br; CONHCH$_3$; 4-F-3-Cl], [735: Br; CONHCH$_3$; 3,4,5-(F)$_3$], [736: Br; CONHCH$_3$; 4-Cl-3,5-(F)$_2$], [737: Br; CONHCH$_2$CH$_3$; 4-Cl], [738: Br; CONHCH$_2$CH$_3$; 3-Cl], [739: Br; CONHCH$_2$CH$_3$; 4-F], [740: Br; CONHCH$_2$CH$_3$; 4-Br], [741: Br; CONHCH$_2$CH$_3$; 4-I], [742: Br; CONHCH$_2$CH$_3$; 4-CN], [743: Br; CONHCH$_2$CH$_3$; 4-NO$_2$], [744: Br; CONHCH$_2$CH$_3$; 4-CF$_3$], [745: Br; CONHCH$_2$CH$_3$; 3-CF$_3$], [746: Br; CONHCH$_2$CH$_3$; 4-CF$_2$CF$_3$], [747: Br; CONHCH$_2$CH$_3$; 4-C≡CH], [748: Br; CONHCH$_2$CH$_3$; 4-OCF$_3$], [749: Br; CONHCH$_2$CH$_3$; 4-SCF$_3$], [750: Br; CONHCH$_2$CH$_3$; 4-SCH$_3$], [751: Br; CONHCH$_2$CH$_3$; 4-SOCH$_3$], [752: Br; CONHCH$_2$CH$_3$; 4-SO$_2$CH$_3$], [753: Br; CONHCH$_2$CH$_3$; 4-Cl-3-F], [754: Br; CONHCH$_2$CH$_3$; 4-Br-3-F], [755: Br; CONHCH$_2$CH$_3$; 3,4-(Cl)$_2$], [756: Br;

CONHCH₂CH₃; 4-Cl-3-CF₃], [757: Br; CONHCH₂CH₃; 4-F-3-Cl], [758: Br; CONHCH₂CH₃; 3,4,5-(F)₃], [759: Br; CONHCH₂CH₃; 4-Cl-3,5-(F)₂], [760: Br; CON(CH₃)₂; 4-Cl], [761: Br; CON(CH₃)₂; 3-Cl], [762: Br; CON(CH₃)₂; 4-F], [763: Br; CON(CH₃)₂; 4-Br], [764: Br; CON(CH₃)₂; 4-I], [765: Br; CON(CH₃)₂; 4-CN], [766: Br; CON(CH₃)₂; 4-NO₂], [767: Br; CON(CH₃)₂; 4-CF₃], [768: Br; CON(CH₃)₂; 3-CF₃], [769: Br; CON(CH₃)₂; 4-CF₂CF₃], [770: Br; CON(CH₃)₂; 4-C≡CH], [771: Br; CON(CH₃)₂; 4-OCF₃], [772: Br; CON(CH₃)₂; 4-SCF₃], [773: Br; CON(CH₃)₂; 4-SCH₃], [774: Br; CON(CH₃)₂; 4-SOCH₃], [775: Br; CON(CH₃)₂; 4-SO₂CH₃], [776: Br; CON(CH₃)₂; 4-Cl-3-F], [777: Br; CON(CH₃)₂; 4-Br-3-F], [778: Br; CON(CH₃)₂; 3,4-(Cl)₂], [779: Br; CON(CH₃)₂; 4-Cl-3-CF₃], [780: Br; CON(CH₃)₂; 4-F-3-Cl], [781: Br; CON(CH₃)₂; 3,4,5-(F)₃], [782: Br; CON(CH₃)₂; 4Cl-3,5-(F)₂], [783: Br; CON(CH₂CH₃)₂; 4-Cl], [784: Br; CON(CH₂CH₃)₂; 3-Cl], [785: Br; CON(CH₂CH₃)₂; 4-F], [786: Br; CON(CH₂CH₃)₂; 4-Br], [787: Br; CON(CH₂CH₃)₂; 4-I], [788: Br; CON(CH₂CH₃)₂; 4-CN], [789: Br; CON(CH₂CH₃)₂; 4-NO₂], [790: Br; CON(CH₂CH₃)₂; 4-CF₃], [791: Br; CON(CH₂CH₃)₂; 3-CF₃], [792: Br; CON(CH₂CH₃)₂; 4-CF₂CF₃], [793: Br; CON(CH₂CH₃)₂; 4-C≡CH], [794: Br; CON(CH₂CH₃)₂; 4-OCF₃], [795: Br; CON(CH₂CH₃)₂; 4-SCF₃], [796: Br; CON(CH₂CH₃)₂; 4-SCH₃], [797: Br; CON(CH₂CH₃)₂; 4-SOCH₃], [798: Br; CON(CH₂CH₃)₂; 4-SO₂CH₃], [799: Br; CON(CH₂CH₃)₂; 4-Cl-3-F], [800: Br; CON(CH₂CH₃)4-Br-3-F], [801: Br;CON(CH₂CH₃)₂; 3,4-(Cl)₂], [802: Br; CON(CH₂CH₃)₂; 4-Cl-3-CF₃], [803: Br; CON(CH₂CH₃)₂; 4-F-3-Cl], [804: Br; CON(CH₂CH₃)₂; 3,4,5-(F)₃], [805: Br; CON(CH₂CH₃)₂; 4-Cl-3,5-(F)₂], [806: Br; CSNH₂; 4-Cl], [807: Br; CSNH₂; 3-Cl], [808: Br; CSNH₂; 4-F], [809: Br; CSNH₂; 4-Br], [810: Br; CSNH₂; 4-I], [811: Br; CSNH₂; 4-CN], [812: Br; CSNH₂; 4-NO₂], [813: Br; CSNH₂; 4-CF₃], [814: Br; CSNH₂; 3-CF₃], [815: Br;CSNH₂; 4-CF₂CF₃], [816: Br; CSNH₂; 4-C≡CH], [817: Br; CSNH₂; 4-OCF₃], [818: Br; CSNH₂; 4-SCF₃], [819: Br; CSNH₂; 4-SCH₃], [820: Br; CSNH₂; 4-SOCH₃], [821: Br; CSNH₂; 4-SO₂CH₃], [822: Br; CSNH₂; 4-Cl-3-F], [823: Br; CSNH₂; 4-Br-3-F], [824: Br; CSNH₂; 3,4-(Cl)₂], [825: Br; CSNH₂; 4-Cl-3-CF₃], [826: Br; CSNH₂; 4-F-3-Cl], [827: Br; CSNH₂; 3,4,5-(F)₃], [828: Br; CSNH₂; 4-Cl-3,5-(F)₂], [829: Br; CSNHCH₃; 4-Cl], [830: Br; CSNHCH₃; 3-Cl], [831: Br; CSNHCH₃; 4-F], [832: Br; CSNHCH₃; 4-Br], [833: Br; CSNHCH₃; 4-I], [834: Br; CSNHCH₃; 4-CN], [835: Br; CSNHCH₃; 4-NO₂], [836: Br; CSNHCH₃; 4-CF₃], [837: Br; CSNHCH₃; 3-CF₃], [838: Br; CSNHCH₃; 4-CF₂CF₃], [839: Br; CSNHCH₃; 4-C≡CH], [840: Br; CSNHCH₃; 4-OCF₃], [841: Br; CSNHCH₃; 4-SCF₃], [842: Br; CSNHCH₃; 4-SCH₃], [843: Br; CSNHCH₃; 4-SOCH₃], [844: Br; CSNHCH₃; 4-SO₂CH₃], [845: Br; CSNHCH₃; 4-Cl-3-F], [846: Br; CSNHCH₃; 4-Br-3-F], [847: Br; CSNHCH₃; 3,4-(Cl)₂], [848: Br; CSNHCH₃; 4-Cl-3-CF₃], [849: Br; CSNHCH₃; 4-F-3-Cl], [850: Br; CSNHCH₃; 3,4,5-(F)₃], [851: Br; CSNHCH₃; 4-Cl-3,5-(F)₂], [852: Br; CSNHCH₂CH₃; 4-Cl], [853: Br; CSNHCH₂CH₃; 3-Cl], [854: Br; CSNHCH₂CH₃; 4-F], [855: Br; CSNHCH₂CH₃; 4-Br], [856: Br; CSNHCH₂CH₃; 4-I], [857: Br; CSNHCH₂CH₃; 4-CN], [858: Br; CSNHCH₂CH₃; 4-NO₂], [859: Br; CSNHCH₂CH₃; 4-CF₃], [860: Br; CSNHCH₂CH₃; 3-CF₃], [861: Br; CSNHCH₂CH₃; 4-CF₂CF₃], [862: Br; CSNHCH₂CH₃; 4-C≡CH], [863: Br; CSNHCH₂CH₃; 4-OCF₃], [864: Br; CSNHCH₂CH₃; 4-SCF₃], [865: Br; CSNHCH₂CH₃; 4-SCH₃], [866: Br; CSNHCH₂CH₃; 4-SOCH₃], [867: Br; CSNHCH₂CH₃; 4-SO₂CH₃], [868: Br; CSNHCH₂CH₃; 4-Cl-3-F], [869: Br; CSNHCH₂CH₃; 4-Br-3-F], [870: Br; CSNHCH₂CH₃; 3,4-(Cl)₂], [871: Br; CSNHCH₂CH₃; 4-Cl-3-CF₃], [872: Br; CSNHCH₂CH₃; 4-F-3-Cl], [873: Br; CSNHCH₂CH₃; 3,4,5-(F)₃], [874: Br; CSNHCH₂CH₃; 4-Cl-3,5-(F)₂], [875: Br; CSN(CH₃)₂; 4-Cl], [876: Br; CSN(CH₃)₂; 3-Cl], [877: Br; CSN(CH₃)₂; 4-F], [878: Br; CSN(CH₃)₂; 4-Br], [879: Br; CSN(CH₃)₂; 4-I], [880: Br; CSN(CH₃)₂; 4-CN], [881: Br; CSN(CH₃)₂; 4-NO₂], [882: Br; CSN(CH₃)₂; 4-CF₃], [883: Br; CSN(CH₃)₂; 3-CF₃], [884: Br; CSN(CH₃)₂; 4-CF₂CF₃], [885: Br; CSN(CH₃)₂; 4-C≡CH], [886: Br; CSN(CH₃)₂; 4-OCF₃], [887: Br; CSN(CH₃)₂; 4-SCF₃], [888: Br; CSN(CH₃)₂; 4-SCH₃], [889: Br; CSN(CH₃)₂; 4-SOCH₃], [890: Br; CSN(CH₃)₂; 4-SO₂CH₃], [891: Br; CSN(CH₃)₂; 4-Cl-3-F], [892: Br; CSN(CH₃)₂; 4-Br-3-F], [893: Br; CSN(CH₃)₂; 3,4-(Cl)₂], [894: Br; CSN(CH₃)₂; 4-Cl-3-CF₃], [895: Br:CSN(CH₃)₂: 4-F-3-Cl], [896: Br; CSN(CH₃)₂; 3,4,5-(F)₃], [897: Br; CSN(CH₃)₂; 4-Cl-3,5-(F)₂], [898: Br; CSN(CH₂CH₃)₂; 4Cl], [899: Br; CSN(CH₂CH₃)₂; 3-Cl], [900: Br; CSN(CH₂CH₃)₂; 4-F], [901: Br; CSN(CH₂CH₃)₂; 4-Br], [902: Br; CSN(CH₂CH₃)₂; 4-I], [903: Br; CSN(CH₂CH₃)₂; 4-CN], [904: Br; CSN(CH₂CH₃)₂; 4-NO₂], [905: Br; CSN(CH₂CH₃)₂; 4-CF₃], [906: Br; CSN(CH₂CH₃)₂; 3-CF₃], [907: Br; CSN(CH₂CH₃)₂; 4-CF₂CF₃], [908: Br; CSN(CH₂CH₃)₂; 4-C≡CH], [909: Br; CSN(CH₂CH₃)₂; 4-OCF₃], [910: Br; CSN(CH₂CH₃)₂; 4-SCF₃], [911: Br; CSN(CH₂CH₃)₂; 4-SCH₃], [912: Br; CSN(CH₂CH₃)₂; 4-SOCH₃], [913: Br; CSN(CH₂CH₃)₂; 4-SO₂CH₃], [914: Br; CSN(CH₂CH₃)₂; 4-Cl-3-F], [915: Br; CSN(CH₂CH₃)₂; 4-Br-3-F], [916: Br; CSN(CH₂CH₃)₂; 3,4-(Cl)₂], [917: Br; CSN(CH₂CH₃)₂; 4-Cl-3-CF₃], [918: Br; CSN(CH₂CH₃)₂; 4-F-3-Cl], [919: Br; CSN(CH₂CH₃)₂; 3,4,5-(F)₃], [920: Br; CSN(CH₂CH₃)₂; 4-Cl-3,5-(F)₂], [921: CH₃; CONH₂; 4-Cl], [922: CH₃; CONH₂; 3-Cl], [923: CH₃; CONH₂; 4-F], [924: CH₃; CONH₂; 4-Br], [925: CH₃; CONH₂; 4-I], [926: CH₃; CONH₂; 4-CN], [927: CH₃; CONH₂; 4-NO₂], [928: CH₃; CONH₂; 4-CF₃], [929: CH₃; CONH₂; 3-CF₃], [930: CH₃; CONH₂; 4-CF₂CF₃], [931: CH₃; CONH₂; 4-C≡CH], [932: CH₃; CONH₂; 4-OCF₃], [933: CH₃; CONH₂; 4-SCF₃], [934: CH₃; CONH₂; 4-SCH₃], [935: CH₃; CONH₂; 4-SOCH₃], [936: CH₃; CONH₂; 4-SO₂CH₃], [937: CH₃; CONH₂; 4-Cl-3-F], [938: CH₃; CONH₂; 4-Br-3-F], [939: CH₃; CONH₂; 3,4-(Cl)₂], [940: CH₃; CONH₂; 4-Cl-3-CF₃], [941: CH₃; CONH₂; 4-F-3-Cl], [942: CH₃; CONH₂; 3,4,5-(F)₃], [943: CH₃; CONH₂; 4-Cl-3,5-(F)₂], [944: CH₃; CONHCH₃; 4-Cl], [945: CH₃; CONHCH₃; 3-Cl], [946: CH₃; CONHCH₃; 4-F], [947: CH₃; CONHCH₃; 4-Br], [948: CH₃; CONHCH₃; 4-I], [949: CH₃; CONHCH₃; 4-CN], [950: CH₃; CONHCH₃; 4-NO₂], [951: CH₃; CONHCH₃; 4-CF₃], [952: CH₃; CONHCH₃; 3-CF₃], [953: CH₃; CONHCH₃; 4-CF₂CF₃], [954: CH₃; CONHCH₃; 4-C≡CH], [955: CH₃; CONHCH₃; 4-OCF₃], [956: CH₃; CONHCH₃; 4-SCF₃], [957: CH₃; CONHCH₃; 4-SCH₃], [958: CH₃; CONHCH₃; 4-SOCH₃], [959: CH₃; CONHCH₃; 4-SO₂CH₃], [960: CH₃; CONHCH₃; 4-Cl-3-F], [961: CH₃; CONHCH₃; 4-Br-3-F], [962: CH₃; CONHCH₃; 3,4-(Cl)₂], [963: CH₃; CONHCH₃; 4-Cl-3-CF₃], [964: CH₃; CONHCH₃; 4-F-3-Cl], [965: CH₃; CONHCH₃; 3,4,5-(F)₃], [966: CH₃; CONHCH₃; 4-Cl-3,5-(F)₂], [967: CH₃; CONHCH₂CH₃; 4-Cl], [968: CH₃; CONHCH₂CH₃; 3-Cl], [969: CH₃; CONHCH₂CH₃; 4-F], [970: CH₃; CONHCH₂CH₃; 4-Br], [971: CH₃; CONHCH₂CH₃; 4-I], [972: CH₃; CONHCH9CH₃; 4-CN], [973: CH₃; CONHCH₂CH₃; 4-NO₂], [974: CH₃; CONHCH₂CH₃; 4-CF₃], [975: CH₃; CONHCH₂CH₃; 3-CF₃], [976: CH₃; CONHCH9CH₃; 4-CF₂CF₃], [977: CH₃; CONHCH₂CH₃;

4-C≡CH], [978: CH₃; CONHCH₂CH₃; 4-OCF₃], [979: CH₃; CONHCH₂CH₃; 4-SCF₃], [980: CH₃; CONHCH₂CH₃; 4-SCH₃], [981: CH₃; CONHCH₂CH₃; 4-SOCH₃], [982: CH₃; CONHCH₂CH₃; 4-SO₂CH₃], [983: CH₃; CONHCH₂CH₃; 4-Cl-3-F], [984: CH₃; CONHCH₂CH₃; 4-BR-3-F], [985: CH₃; CONHCH₂CH₃; 3,4-(Cl)₂], [986: CH₃; CONHCH₂CH₃; 4-Cl-3-CF₃], [987: CH₃; CONHCH₂CH₃; 4-F-3-Cl], [988: CH₃; CONHCH₂CH₃; 3,4,5-(F)₃], [989: CH₃; CONHCH₂CH₃; 4-Cl-3,5-(F)₂], [990: CH₃; CON(CH₃)₂; 4-Cl], [991: CH₃; CON(CH₃)₂; 3-Cl], [992: CH₃; CON(CH₃)₂; 4-F], [993: CH₃; CON(CH₃)₂; 4-Br], [994: CH₃; CON(CH₃)₂; 4-I], [995: CH₃; CON(CH₃)₂; 4-CN], [996: CH₃; CON(CH₃)₂; 4-NO₂], [997: CH₃; CON(CH₃)₂; 4-CF₃], [998: CH₃; CON(CH₃)₂; 3CF₃], [999: CH₃; CON(CH₃)₂; 4-CF₂CF₃], [1000: CH₃; CON(CH₃)₂; 4-C≡CH], [1001: CH₃; CON(CH₃)₂; 4-OCF₃], [1002: CH₃; CON(CH₃)₂; 4-SCF₃], [1003: CH₃; CON(CH₃)₂; 4-SCH₃], [1004: CH₃; CON(CH₃)₂; 4-SOCH₃], [1005: CH₃; CON(CH₃)₂; 4-SO₂CH₃], [1006: CH₃; CON(CH₃)₂; 4-Cl-3-F], [1007: CH₃; CON(CH₃)₂; 4-Br-3-F], [1008: CH₃; CON(CH₃)₂; 3,4-(Cl)₂], [1009: CH₃; CON(CH₃)₂; 4-Cl-3-CF₃], [1010: CH₃; CON(CH₃)₂; 4-F-3-Cl], [1011: CH₃; CON(CH₃)₂; 3,4,5-(F)₃], [1012: CH₃; CON(CH₃)₂; 4-Cl-3,5-(F)₂], [1013: CH₃; CON(CH₂CH₃)₂; 4-Cl], [1014: CH₃; CON(CH₂CH₃)₂; 3-Cl], [1015: CH₃; CON(CH₂CH₃)₂; 4-F], [1016: CH₃; CON(CH₂CH₃)₂; 4-Br], [1017: CH₃; CON(CH₂CH₃)₂; 4-I], [1018: CH₃; CON(CH₂CH₃)₂; 4-CN], [1019: CH₃; CON(CH₂CH₃)₂; 4-NO₂], [1020: CH₃; CON(CH₂CH₃)₂; 4-CF₃], [1021: CH₃; CON(CH₂CH₃)₂; 3-CF₃], [1022: CH₃; CON(CH₂CH₃)₂; 4-CF₂CF₃], [1023: CH₃; CON(CH₂CH₃)₂; 4-C≡CH], [1024: CH₃; CON(CH₂CH₃)₂; 4-OCF₃], [1025: CH₃; CON(CH₂CH₃)₂; 4-SCF₃], [1026: CH₃; CON(CH₂CH₃)₂; 4-SCH₃], [1027: CH₃; CON(CH₂CH₃)₂; 4-SOCH₃], [1028: CH₃; CON(CH₂CH₃)₂; 4-SO₂CH₃], [1029: CH₃; CON(CH₂CH₃)₂; 4-Cl-3-F], [1030: CH₃; CON(CH₂CH₃)₂; 4-Br-3-F], [1031: CH₃; CON(CH₂CH₃)₂; 3,4-(Cl)₂], [1032: CH₃; CON(CH₂CH₃)₂; 4-Cl-3-CF₃], [1033: CH₃; CON(CH₂CH₃)₂; 4-F-3-Cl], [1034: CH₃; CON(CH₂CH₃)₂; 3,4,5-(F)₃], [1035: CH₃; CON(CH₂CH₃)₂; 4-Cl-3,5-(F)₂], [1036: CH₃; CSNH₂; 4-Cl], [1037: CH₃; CSNH₂; 3-Cl], [1038: CH₃; CSNH₂; 4-F], [1039: CH₃; CSNH₂; 4-Br], [1040: CH₃; CSNH₂; 4-I], [1041: CH₃; CSNH₂; 4-CN], [1042: CH₃; CSNH₂; 4-NO₂], [1043: CH₃; CSNH₂; 4-CF₃], [1044: CH₃; CSNH₂; 3-CF₃], [1045: CH₃; CSNH₂; 4-CF₂CF₃], [1046: CH₃; CSNH₂; 4-C≡CH], [1047: CH₃; CSNH₂; 4-OCF₃], [1048: CH₃; CSNH₂; 4-SCF₃], [1049: CH₃; CSNH₂; 4-SCH₃], [1050: CH₃; CSNH₂; 4-SOCH₃], [1051: CH₃; CSNH₂; 4-SO₂CH₃], [1052: CH₃; CSNH₂; 4-Cl-3-F], [1053: CH₃; CSNH₂; 4-Br-3-F], [1054: CH₃; CSNH₂; 3,4-(Cl)₂], [1055: CH₃; CSNH₂; 4-Cl-3-CF₃], [1056: CH₃; CSNH₂; 4-F-3-Cl], [1057: CH₃; CSNH; 3,4,5-(F)₃], [1058: CH₃; CSNH₂; 4-Cl-3,5-(F)₂], [1059: CH₃; CSNHCH₃; 4-Cl], [1060: CH₃; CSNHCH₃; 3-Cl], [1061: CH₃; CSNHCH₃; 4-F], [1062: CH₃; CSNHCH₃; 4-Br], [1063: CH₃; CSNHCH₃; 4-I], [1064: CH₃; CSNHCH₃; 4-CN], [1065: CH₃; CSNHCH₃; 4-NO₂], [1066: CH₃; CSNHCH₃; 4-CF₃], [1067: CH₃; CSNHCH₃; 3-CF₃], [1068: CH₃; CSNHCH₃; 4-CF₂CF₃], [1069: CH₃; CSNHCH₃; 4-C≡CH], [1070: CH₃; CSNHCH₃; 4-OCF₃], [1071: CH₃; CSNHCH₃; 4-SCF₃], [1072: CH₃; CSNHCH₃; 4-SCH₃], [1073: CH₃; CSNHCH₃; 4-SOCH₃], [1074: CH₃; CSNHCH₃; 4-SO₂CH₃], [1075: CH₃; CSNHCH₃; 4-Cl-3-F], [1076: CH₃; CSNHCH₃; 4-Br-3-F], [1077: CH₃; CSNHCH₃; 3,4-(Cl)₂], [1078: CH₃; CSNHCH₃; 4-Cl-3-CF₃], [1079: CH₃; CSNHCH₃; 4-F-3-Cl], [1080: CH₃; CSNHCH₃; 3,4,5-(F)₃], [1081: CH₃; CSNHCH₃; 4-Cl-3,5-(F)₂], [1082: CH₃; CSNHCH₂CH₃; 4-Cl], [1083: CH₃; CSNHCH₂CH₃; 3-Cl], [1084: CH₃; CSNHCH₂CH₃; 4-F], [1085: CH₃; CSNHCH₂CH₃; 4-Br], [1086: CH₃; CSNHCH₂CH₃; 4-I], [1087: CH₃; CSNHCH₂CH₃; 4-CN], [1088: CH₃; CSNHCH₂CH₃; 4-NO₂], [1089: CH₃; CSNHCH₂CH₃; 4-CF₃], [1090: CH₃; CSNHCH₂CH₃; 3-CF₃], [1091: CH₃; CSNHCH₂CH₃; 4-CF₂CF₃], [1092: CH₃; CSNHCH₂CH₃; 4-C≡CH], [1093: CH₃; CSNHCH₂CH₃; 4-OCF₃], [1094: CH₃; CSNHCH₂CH₃; 4-SCF₃], [1095: CH₃; CSNHCH₂CH₃; 4-SCH₃], [1096: CH₃; CSNHCH₂CH₃; 4-SOCH₃], [1097: CH₃; CSNHCH₂CH₃; 4-SO₂CH₃], [1098: CH₃; CSNHCH₂CH₃; 4-Cl-3-F], [1099: CH₃; CSNHCH₂CH₃; 4-Br-3-F], [1100: CH₃; CSNHCH₂CH₃; 3,4-(Cl)₂], [1101: CH₃; CSNHCH₂CH₃; 4-Cl-3-CF₃], [1102: CH₃; CSNHCH₂CH₃; 4-F-3-Cl], [1103: CH₃; CSNHCH₂CH₃; 3,4,5-(F)₃], [1104: CH₃; CSNHCH₂CH₃; 4-Cl-3,5-(F)₂], [1105: CH₃; CSN(CH₃)₂; 4-Cl], [1106: CH₃; CSN(CH₃)₂; 3-Cl], [1107: CH₃; CSN(CH₃)₂; 4-F], [1108: CH₃; CSN(CH₃)₂; 4-Br], [1109: CH₃; CSN(CH₃)₂; 4-I], [1110: CH₃; CSN(CH₃)₂; 4-CN], [1111: CH₃; CSN(CH₃)₂; 4-NO₂], [1112: CH₃; CSN(CH₃)₂; 4-CF₃], [1113: CH₃; CSN(CH₃)₂; 3-CF₃], [1114: CH₃; CSN(CH₃)₂; 4-CF₂CF₃], [1115: CH₃; CSN(CH₃)₂; 4-C≡CH], [1116: CH₃; CSN(CH₃)₂; 4-OCF₃], [1117: CH₃; CSN(CH₃)₂; 4-SCF₃], [1118: CH₃; CSN(CH₃)₂; 4-SCH₃], [1119: CH₃; CSN(CH₃)₂; 4-SOCH₃], [1120: CH₃; CSN(CH₃)₂; 4SO₂CH₃], [1121: CH₃; CSN(CH₃)₂; 4-Cl-3-F], [1122: CH₃; CSN(CH₃)₂; 4-Br-3-F], [1123: CH₃; CSN(CH₃)₂; 3,4-(Cl)₂], [1124: CH₃; CSN(CH₃)₂; 4-Cl-3-CF₃], [1125: CH₃; CSN(CH₃)₂; 4-F-3-Cl], [1126: CH₃; CSN(CH₃)₂; 3,4,5-(F)₃], [1127: CH₃; CSN(CH₃)₂; 4-Cl-3,5-(F)₂], [1128: CH₃; CSN(CH₂CH₃)₂; 4-Cl], [1129: CH₃; CSN(CH₂CH₃)₂; 3-Cl], [1130: CH₃; CSN(CH₂CH₃)₂; 4-F], [1131: CH₃; CSN(CH₂CH₃)₂; 4-Br], [1132: CH₃; CSN(CH₂CH₃)₂; 4-I], [1133: CH₃; CSN(CH₂CH₃)₂; 4-CN], [1134: CH₃; CSN(CH₂CH₃)₂; 4-NO₂], [1135: CH₃; CSN(CH₂CH₃)₂; 4-CF₃], [1136: CH₃; CSN(CH₂CH₃)₂; 3-CF₃], [1137: CH₃; CSN(CH₂CH₃)₂; 4-CF₂CF₃], [1138: CH₃; CSN(CH₂CH₃)₂; 4-C≡CH], [1139: CH₃; CSN(CH₂CH₃)₂; 4-OCF₃], [1140: CH₃; CSN(CH₂CH₃)₂; 4-SCF₃], [1141: CH₃; CSN(CH₂CH₃)₂; 4-SCH₃], [1142: CH₃; CSN(CH₂CH₃)₂; 4-SOCH₃], [1143: CH₃; CSN(CH₂CH₃)₂; 4-SO₂CH₃], [1144: CH₃; CSN(CH₂CH₃)₂; 4-Cl-3-F], [1145: CH₃; CSN(CH₂CH₃)₂; 4-Br-3-F], [1146: CH₃; CSN(CH₂CH₃)₂; 3,4-(Cl)₂], [1147: CH₃; CSN(CH₂CH₃)₂; 4-Cl-3-CF₃], [1148: CH₃; CSN(CH₂CH₃)₂; 4-F-3-Cl], [1149: CH₃; CSN(CH₂CH₃)₂; 3,4,5-(F)₃], [1150: CH₃; CSN(CH₂CH₃)₂; 4-Cl-3,5-(F)₂], [1151: CH₂CH₃; CONH₂; 4-Cl], [1152: CH₂CH₃; CONH₂; 3-Cl], [1153: CH₂CH₃; CONH₂; 4-F], [1154: CH₂CH₃; CONH₂; 4-Br], [1155: CH₂CH₃; CONH₂; 4-I], [1156: CH₂CH₃; CONH₂; 4-CN], [1157: CH₂CH₃; CONH₂; 4-NO₂], [1158: CH₂CH₃; CONH₂; 4-CF₃], [1159: CH₂CH₃; CONH₂; 3-CF₃], [1160: CH₂CH₃; CONH₂; 4-CF₂CF₃], [1161: CH₂CH₃; CONH₂; 4-C≡CH], [1162: CH₂CH₃; CONH₂; 4-OCF₃], [1163: CH₂CH₃; CONH₂; 4-SCF₃], [1164: CH₂CH₃; CONH₂; 4-SCH₃], [1165: CH₂CH₃; CONH₂; 4-SOCH₃], [1166: CH₂CH₃; CONH₂; 4-SO₂CH₃], [1167: CH₂CH₃; CONH₂; 4-Cl-3-F], [1168: CH₂CH₃; CONH₂; 4-Br-3-F], [1169: CH₂CH₃; CONH₂; 3,4-(Cl)₂], [1170: CH₂CH₃; CONH₂; 4-Cl-3-CF₃], [1171: CH₂CH₃; CONH₂; 4-F-3-Cl], [1172: CH₂CH₃; CONH₂; 3,4,5-(F)₃], [1173: CH₂CH₃; CONH₂; 4-Cl-3,5-(F)₂], [1174: CH₂CH₃; CONHCH₃; 4-Cl], [1175: CH₂CH₃; CONHCH₃; 3-Cl], [1176: CH₂CH₃; CON-

[1177: CH₂CH₃; CONHCH₃; 4-F], [1177: CH₂CH₃; CONHCH₃; 4-Br], [1178: CH₂CH₃; CONHCH₃; 4-I], [1179: CH₂CH₃; CONHCH₃; 4-CN], [1180: CH₂CH₃; CONHCH₃; 4-NO₂], [1181: CH₂CH₃; CONHCH₃; 4-CF₃], [1182: CH₂CH₃; CONHCH₃; 3-CF₃], [1183: CH₂CH₃; CONHCH₃; 4-CF₂CF₃], [1184: CH₂CH₃; CONHCH₃; 4-C≡CH], [1185: CH₂CH₃; CONHCH₃; 4-OCF₃], [1186: CH₂CH₃; CONHCH₃; 4-SCF₃], [1187: CH₂CH₃; CONHCH₃; 4-SCH₃], [1188: CH₂CH₃; CONHCH₃; 4-SOCH₃], [1189: CH₂CH₃; CONHCH₃; 4-SO₂CH₃], [1190: CH₂CH₃; CONHCH₃; 4-Cl-3-F], [1191: CH₂CH₃; CONHCH₃; 4-Br-3-F], [1192: CH₂CH₃; CONHCH₃; 3,4-(Cl)₂], [1193: CH₂CH₃; CONHCH₃; 4-Cl-3-CF₃], [1194: CH₂CH₃; CONHCH₃; 4-F-3-Cl], [1195: CH₂CH₃; CONHCH₃; 3,4,5-(F)₃], [1196: CH₂CH₃; CONHCH₃; 4-Cl-3,5-(F)₂], [1197: CH₂CH₃; CONHCH₂CH₃; 4-Cl], [1198: CH₂CH₃; CONHCH₂CH₃; 3-Cl], [1199: CH₂CH₃; CONHCH₂CH₃; 4-F], [1200: CH₂CH₃; CONHCH₂CH₃; 4-Br], [1201: CH₂CH₃; CONHCH₂CH₃; 4-I], [1202: CH₂CH₃; CONHCH₂CH₃; 4-CN], [1203: CH₂CH₃; CONHCH₂CH₃; 4-NO₂], [1204: CH₂CH₃; CONHCH₂CH₃; 4-CF₃], [1205: CH₂CH₃; CONHCH₂CH₃; 3-CF₃], [1206: CH₂CH₃; CONHCH₂CH₃; 4-CF₂CF₃], [1207: CH₂CH₃; CONHCH₂CH₃; 4-C≡CH], [1208: CH₂CH₃; CONHCH₂CH₃; 4-OCF₃], [1209: CH₂CH₃; CONHCH₂CH₃; 4-SCF₃], [1210: CH₂CH₃; CONHCH₂CH₃; 4-SCH₃], [1211: CH₂CH₃; CONHCH₂CH₃; 4-SOCH₃], [1212: CH₂CH₃; CONHCH₂CH₃; 4-SO₂CH₃], [1213: CH₂CH₃; CONHCH₂CH₃; 4-Cl-3-F], [1214: CH₂CH₃; CONHCH₂CH₃; 4-Br-3-F], [1215: CH₂CH₃; CONHCH₂CH₃; 3,4-(Cl)₂], [1216: CH₂CH₃; CONHCH₂CH₃; 4-Cl-3-CF₃], [1217: CH₂CH₃; CONHCH₂CH₃; 4-F-3-Cl], [1218: CH₂CH₃; CONHCH₂CH₃; 3,4,5-(F)₃], [1219: CH₂CH₃; CONHCH₂CH₃; 4-Cl-3,5-(F)₂], [1220: CH₂CH₃; CON(CH₃)₂; 4-Cl], [1221: CH₂CH₃; CON(CH₃)₂; 3-Cl], [1222: CH₂CH₃; CON(CH₃)₂; 4-F], [1223: CH₂CH₃; CON(CH₃)₂; 4-Br], [1224: CH₂CH₃; CON(CH₃)₂; 4-I], [1225: CH₂CH₃; CON(CH₃)₂; 4-CN], [1226: CH₂CH₃; CON(CH₃)₂; 4-NO₂], [1227: CH₂CH₃; CON(CH₃)₂; 4-CF₃], [1228: CH₂CH₃; CON(CH₃)₂; 3-CF₃], [1229: CH₂CH₃; CON(CH₃)₂; 4-CF₂CF₃], [1230: CH₂CH₃; CON(CH₃)₂; 4-C≡CH], [1231: CH₂CH₃; CON(CH₃)₂; 4-OCF₃], [1232: CH₂CH₃; CON(CH₃)₂; 4-SCF₃], [1233: CH₂CH₃; CON(CH₃)₂; 4-SCH₃], [1234: CH₂CH₃; CON(CH₃)₂; 4-SOCH₃], [1235: CH₂CH₃; CON(CH₃)₂; 4-SO₂CH₃], [1236: CH₂CH₃; CON(CH₃)₂; 4-Cl-3-F], [1237: CH₂CH₃; CON(CH₃)₂; 4-Br-3-F], [1238: CH₂CH₃; CON(CH₃)₂; 3,4-(Cl)₂], [1239: CH₂CH₃; CON(CH₃)₂; 4-Cl-3-CF₃], [1240: CH₂CH₃; CON(CH₃)₂; 4-F-3-Cl], [1241: CH₂CH₃; CON(CH₃)₂; 3,4,5-(F)₃], [1242: CH₂CH₃; CON(CH₃)₂; 4-Cl-3,5-(F)₂], [1243: CH₂CH₃; CON(CH₂CH₃)₂; 4-Cl], [1244: CH₂CH₃; CON(CH₂CH₃)₂; 3-Cl], [1245: CH₂CH₃; CON(CH₂CH₃)₂; 4-F], [1246: CH₂CH₃; CON(CH₂CH₃)₂; 4-Br], [1247: CH₂CH₃; CON(CH₂CH₃)₂; 4-I], [1248: CH₂CH₃; CON(CH₂CH₃)₂; 4-CN], [1249: CH₂CH₃; CON(CH₂CH₃)₂; 4-NO₂], [1250: CH₂CH₃; CON(CH₂CH₃)₂; 4-CF₃], [1251: CH₂CH₃; CON(CH₂CH₃)₂; 3-CF₃], [1252: CH₂CH₃; CON(CH₂CH₃)₂; 4-CF₂CF₃], [1253: CH₂CH₃; CON(CH₂CH₃)₂; 4-C≡CH], [1254: CH₂CH₃; CON(CH₂CH₃)₂; 4-OCF₃], [1255: CH₂CH₃; CON(CH₂CH₃)₂; 4-SCF₃], [1256: CH₂CH₃; CON(CH₂CH₃)₂; 4-SCH₃], [1257: CH₂CH₃; CON(CH₂CH₃)₂; 4-SOCH₃], [1258: CH₂CH₃; CON(CH₂CH₃)₂; 4-SO₂CH₃], [1259: CH₂CH₃; CON(CH₂CH₃)₂; 4-Cl-3-F], [1260: CH₂CH₃; CON(CH₂CH₃)₂; 4-Br-3-F], [1261: CH₂CH₃; CON(CH₂CH₃)₂; 3,4-(Cl)₂], [1262: CH₂CH₃; CON(CH₂CH₃)₂; 4-Cl-3-CF₃], [1263: CH₂CH₃; CON(CH₂CH₃)₂; 4-F-3-Cl], [1264: CH₂CH₃; CON(CH₂CH₃)₂; 3,4,5-(F)₃], [1265: CH₂CH₃; CON(CH₂CH₃)₂; 4-Cl-3,5-(F)₂], [1266: CH₂CH₃; CSNH₂; 4-Cl], [1267: CH₂CH₃; CSNH₂; 3-Cl], [1268: CH₂CH₃; CSNH₂; 4-F], [1269: CH₂CH₃; CSNH₂; 4-Br], [1270: CH₂CH₃; CSNH₂; 4-I], [1271: CH₂CH₃; CSNH₂; 4-CN], [1272: CH₂CH₃; CSNH₂; 4-NO₂], [1273: CH₂CH₃; CSNH₂; 4-CF₃], [1274: CH₂CH₃; CSNH₂; 3-CF₃], [1275: CH₂CH₃; CSNH₂; 4-CF₂CF₃], [1276: CH₂CH₃; CSNH₂; 4-C≡CH], [1277: CH₂CH₃; CSNH₂; 4-OCF₃], [1278: CH₂CH₃; CSNH₂; 4-SCF₃], [1279: CH₂CH₃; CSNH₂; 4-SCH₃], [1280: CH₂CH₃; CSNH₂; 4-SOCH₃], [1281: CH₂CH₃; CSNH₂; 4-SO₂CH₃], [1282: CH₂CH₃; CSNH₂; 4Cl-3-F], [1283: CH₂CH₃; CSNH₂; 4-Br-3-F], [1284: CH₂CH₃; CSNH₂; 3,4-(Cl)₂], [1285: CH₂CH₃; CSNH₂; 4-Cl-3-CF₃], [1286: CH₂CH₃; CSNH₂; 4-F-3-Cl], [1287: CH₂CH₃; CSNH₂; 3,4,5-(F)₃], [1288: CH₂CH₃; CSNH₂; 4-Cl-3,5-(F)₂], [1289: CH₂CH₃; CSNHCH₃; 4-Cl], [1290: CH₂CH₃; CSNHCH₃; 3-Cl], [1291: CH₂CH₃; CSNHCH₃; 4-F], [1292: CH₂CH₃; CSNHCH₃; 4-Br], [1293: CH₂CH₃; CSNHCH₃; 4-I], [1294: CH₂CH₃; CSNHCH₃; 4-CN], [1295: CH₂CH₃; CSNHCH₃; 4-NO₂], [1296: CH₂CH₃; CSNHCH₃; 4-CF₃], [1297: CH₂CH₃; CSNHCH₃; 3-CF₃], [1298: CH₂CH₃; CSNHCH₃; 4-CF₂CF₃], [1299: CH₂CH₃; CSNHCH₃; 4-C≡CH], [1300: CH₂CH₃; CSNHCH₃; 4-OCF₃], [1301: CH₂CH₃; CSNHCH₃; 4-SCF₃], [1302: CH₂CH₃; CSNHCH₃; 4-SCH₃], [1303: CH₂CH₃; CSNHCH₃; 4-SOCH₃], [1304: CH₂CH₃; CSNHCH₃; 4-SO₂CH₃], [1305: CH₂CH₃; CSNHCH₃; 4-Cl-3-F], [1306: CH₂CH₃; CSNHCH₃; 4-Br-3-F], [1307: CH₂CH₃; CSNHCH₃; 3,4-(Cl)₂], [1308: CH₂CH₃; CSNHCH₃; 4-Cl-3-CF₃], [1309: CH₂CH₃; CSNHCH₃; 4-F-3-Cl], [1310: CH₂CH₃; CSNHCH₃; 3,4,5-(F)₃], [1311: CH₂CH₃; CSNHCH₃; 4-Cl-3,5-(F)₂], [1312: CH₂CH₃; CSNHCH₂CH₃; 4-Cl], [1313: CH₂CH₃; CSNHCH₂CH₃; 3-Cl], [1314: CH₂CH₃; CSNHCH₂CH₃; 4-F], [1315: CH₂CH₃; CSNHCH₂CH₃; 4-Br], [1316: CH₂CH₃; CSNHCH₂CH₃; 4-I], [1317: CH₂CH₃; CSNHCH₂CH₃; 4-CN], [1318: CH₂CH₃; CSNHCH₂CH₃; 4-NO₂], [1319: CH₂CH₃; CSNHCH₂CH₃; 4-CF₃], [1320: CH₂CH₃; CSNHCH₂CH₃; 3-CF₃], [1321: CH₂CH₃; CSNHCH₂CH₃; 4-CF₂CF₃], [1322: CH₂CH₃; CSNHCH₂CH₃; 4-C≡CH], [1323: CH₂CH₃; CSNHCH₂CH₃; 4-OCF₃], [1324: CH₂CH₃; CSNHCH₂CH₃; 4-SCF₃], [1325: CH₂CH₃; CSNHCH₂CH₃; 4-SCH₃], [1326: CH₂CH₃; CSNHCH₂CH₃; 4-SOCH₃], [1327: CH₂CH₃; CSNHCH₂CH₃; 4-SO₂CH₃], [1328: CH₂CH₃; CSNHCH₂CH₃; 4-Cl-3-F], [1329: CH₂CH₃; CSNHCH₂CH₃; 4-Br-3-F], [1330: CH₂CH₃; CSNHCH₂CH₃; 3,4-(Cl)₂], [1331: CH₂CH₃; CSNHCH₂CH₃; 4-Cl-3-CF₃], [1332: CH₂CH₃; CSNHCH₂CH₃; 4-F-3-Cl], [1333: CH₂CH₃; CSNHCH₂CH₃; 3,4,5-(F)₃], [1334: CH₂CH₃; CSNHCH₂CH₃; 4-Cl-3,5-(F)₂], [1335: CH₂CH₃; CSN(CH₃)₂; 4-Cl], [1336: CH₂CH₃; CSN(CH₃)₂; 3-Cl], [1337: CH₂CH₃; CSN(CH₃)₂; 4-F], [1338: CH₂CH₃; CSN(CH₃)₂; 4-Br], [1339: CH₂CH₃; CSN(CH₃)₂; 4-I], [1340: CH₂CH₃; CSN(CH₃)₂; 4-CN], [1341: CH₂CH₃; CSN(CH₃)₂; 4-NO₂], [1342: CH₂CH₃; CSN(CH₃)₂; 4-CF₃], [1343: CH₂CH₃; CSN(CH₃)₂; 3-CF₃], [1344: CH₂CH₃; CSN(CH₃)₂; 4-CF₂CF₃], [1345: CH₂CH₃; CSN(CH₃)₂; 4-C≡CH], [1346: CH₂CH₃; CSN(CH₃)₂; 4-OCF₃], [1347: CH₂CH₃; CSN(CH₃)₂; 4-SCF₃], [1348: CH₂CH₃; CSN(CH₃)₂; 4-SCH₃], [1349: CH₂CH₃; CSN (CH₃)₂; 4-SOCH₃], [1350: CH₂CH₃; CSN(CH₃)₂; 4-SO₂CH₃], [1351: CH₂CH₃; CSN(CH₃)₂; 4-Br-3-F], [1352: CH₂CH₃; CSN(CH₃)₂; 4-Br-3-F], [1353: CH₂CH₃; CSN(CH₃)₂; 3,4-(Cl)₂], [1354: CH₂CH₃; CSN(CH₃)₂; 4-Cl-3-CF₃], [1355: CH₂CH₃; CSN(CH₃)₂; 4-F-3-Cl], [1356: CH₂CH₃; CSN(CH₃)₂; 3,4,5-(F)₃], [1357: CH₂CH₃; CSN(CH₃)₂; 4-Cl-3,5-(F)₂], [1358: CH₂CH₃; CSN(CH₂CH₃)₂; 4-Cl], [1359: CH₂CH₃; CSN(CH₂CH₃)₂; 3-Cl], [1360: CH₂CH₃; CSN(CH₂CH₃)₂; 4-F], [1361: CH₂CH₃; CSN(CH₂CH₃)₂; 4-Br], [1362: CH₂CH₃; CSN(CH₂CH₃)₂; 4-I], [1363: CH₂CH₃; CSN(CH₂CH₃)₂; 4-CN], [1364: CH₂CH₃; CSN(CH₂CH₃)₂; 4-NO₂], [1365: CH₂CH₃; CSN(CH₂CH₃)₂; 4-CF₃], [1366: CH₂CH₃; CSN(CH₂CH₃)₂; 3-CF₃], [1367: CH₂CH₃; CSN(CH₂CH₃)₂; 4-CF₂CF₃], [1368: CH₂CH₃; CSN(CH₂CH₃)₂; 4-C≡CH], [1369: CH₂CH₃; CSN(CH₂CH₃)₂; 4-OCF₃], [1370: CH₂CH₃; CSN(CH₂CH₃)₂; 4-SCF₃], [1371: CH₂CH₃; CSN(CH₂CH₃)₂; 4-SCH₃], [1372: CH₂CH₃; CSN(CH₂CH₃)₂; 4-SOCH₃], [1373: CH₂CH₃; CSN(CH₂CH₃)₂; 4-SO₂CH₃], [1374: CH₂CH₃; CSN(CH₂CH₃)₂; 4-Cl-3-F], [1375: CH₂CH₃; CSN(CH₂CH₃)₂; 4-Br-3-F], [1376: CH₂CH₃; CSN(CH₂CH₃)₂; 3,4-(Cl)₂], [1377: CH₂CH₃; CSN(CH₂CH₃)₂; 4-Cl-3-CF₃], [1378: CH₂CH₃; CSN(CH₂CH₃)₂; 4-F-3-Cl], [1379: CH₂CH₃; CSN(CH₂CH₃)2; 3,4,5-(F)₃], [1380: CH₂CH₃; CSN(CH₂CH₃)₂; 4-Cl-3,5-(F)₂], [1381: CH₂CH₂CH₃; CONH₂; 4-Cl], [1382: CH₂CH₂CH₃; CONH₂; 3-Cl], [1383: CH₂CH₂CH₃; CONH₂; 4-F], [1384: CH₂CH₂CH₃; CONH₂; 4-Br], [1385: CH₂CH₂CH₃; CONH₂; 4-I], [1386: CH₂CH₂CH₃; CONH₂; 4-CH], [1387: CH₂CH₂CH₃; CONH₂; 4-NO₂], [1388: CH₂CH₂CH₃; CONH₂; 4-CF₃], [1389: CH₂CH₂CH₃; CONH₂; 3-CF₃], [1390: CH₂CH₂CH₃; CONH₂; 4-CF₂CF₃], [1391: CH₂CH₂CH₃; CONH₂; 4-C≡CH], [1392: CH₂CH₂CH₃; CONH₂; 4-OCF₃], [1393: CH₂CH₂CH₃; CONH₂; 4-SCF₃], [1394: CH₂CH₂CH₃; CONH₂; 4-SCH₃], [1395: CH₂CH₂CH₃; CONH₂; 4-SOCH₃], [1396: CH₂CH₂CH₃; CONH₂; 4-SO₂CH₃], [1397: CH₂CH₂CH₃; CONH₂; 4-Cl-3-F], [1398: CH₂CH₂CH₃; CONH₂; 4-Br-3-F], [1399: CH₂CH₂CH₃; CONH₂; 3,4-(Cl)₂], [1400: CH₂CH₂CH₃; CONH₂; 4-Cl-3-CF₃], [1401: CH₂CH₂CH₃; CONH₂; 4-F-3-Cl], [1402: CH₂CH₂CH₃; CONH₂; 3,4,5-(F)₃], [1403: CH₂CH₂CH₃; CONH₂; 4-Cl-3,5-(F)₂], [1404: CH₂CH₂CH₃; CONHCH₃; 4-Cl], [1405: CH₂CH₂CH₃; CONHCH₃; 3-Cl], [1406: CH₂CH₂CH₃; CONHCH₃; 4F], [1407: CH₂CH₂CH₃; CONHCH₃; 4-Br], [1408: CH₂CH₂CH₃; CONHCH₃; 4-I], [1409: CH₂CH₂CH₃; CONHCH₃; 4-CN], [1410: CH₂CH₂CH₃; CONHCH₃; 4-NO₂], [1411: CH₂CH₂CH₃; CONHCH₃; 4-CF₃], [1412: CH₂CH₂CH₃; CONHCH₃; 3-CF₃], [1413: CH₂CH₂CH₃; CONHCH₃; 4-CF₂CF₃], [1414: CH₂CH₂CH₃; CONHCH₃; 4-C≡CH], [1415: CH₂CH₂CH₃; CONHCH₃; 4-OCF₃], [1416: CH₂CH₂CH₃; CONHCH₃; 4-SCF₃], [1417: CH₂CH₂CH₃; CONHCH₃; 4-SCH₃], [1418: CH₂CH₂CH₃; CONHCH₃; 4-SOCH₃], [1419: CH₂CH₂CH₃; CONHCH₃; 4-SO₂CH₃], [1420: CH₂CH₂CH₃; CONHCH₃; 4-Cl-3-F], [1421: CH₂CH₂CH₃; CONHCH₃; 4-Br-3-F], [1422: CH₂CH₂CH₃; CONHCH₃; 3,4-(Cl)₂], [1423: CH₂CH₂CH₃; CONHCH₃; 4-Cl-3-CF₃], [1424: CH₂CH₂CH₃; CONHCH₃; 4-F-3-Cl], [1425: CH₂CH₂CH₃; CONHCH₃; 3,4,5-(F)₃], [1426: CH₂CH₂CH₃; CONHCH₃; 4-Cl-3,5-(F)₂], [1427: CH₂CH₂CH₃; CONHCH₂CH₃; 4-Cl], [1428: CH₂CH₂CH₃; CONHCH₂CH₃; 3-Cl], [1429: CH₂CH₂CH₃; CONHCH₂CH₃; 4-F], [1430: CH₂CH₂CH₃; CONHCH₂CH₃; 4-Br], [1431: CH₂CH₂CH₃; CONHCH₂CH₃; 4-I], [1432: CH₂CH₂CH₃; CONHCH₂CH₃; 4-CN], [1433: CH₂CH₂CH₃; CONHCH₂CH₃; 4-NO₂], [1434: CH₂CH₂CH₃; CONHCH₂CH₃; 4-CF₃], [1435: CH₂CH₂CH₃; CONHCH₂CH₃; 3-CF₃], [1436: CH₂CH₂CH₃; CONHCH₂CH₃; 4-CF₂CF₃], [1437: CH₂CH₂CH₃; CONHCH₂CH₃; 4-C≡CH], [1438: CH₂CH₂CH₃; CONHCH₂CH₃; 4-OCF₃], [1439: CH₂CH₂CH₃; CONHCH₂CH₃; 4-SCF₃], [1440: CH₂CH₂CH₃; CONHCH₂CH₃; 4-SCH₃], [1441: CH₂CH₂CH₃; CONHCH₂CH₃; 4-SOCH₃], [1442: CH₂CH₂CH₃; CONHCH₂CH₃; 4-SO₂CH₃], [1443: CH₂CH₂CH₃; CONHCH₂CH₃; 4-Cl-3-F], [1444: CH₂CH₂CH₃; CONHCH₂CH₃; 4-Br-3-F], [1445: CH₂CH₂CH₃; CONHCH₂CH₃; 3,4-(Cl)₂], [1446: CH₂CH₂CH₃; CONHCH₂CH₃; 4-Cl-3-CF₃], [1447: CH₂CH₂CH₃; CONHCH₂CH₃; 4-F-3-Cl], [1448: CH₂CH₂CH₃; CONHCH₂CH₃; 3,4,5-(F)₃], [1449: CH₂CH₂CH₃; CONHCH₂CH₃; 4-Cl-3,5-(F)₂], [1450: CH₂CH₂CH₃; CON(CH₃)₂; 4-Cl], [1451: CH₂CH₂CH₃; CON(CH₃)₂; 3-Cl], [1452: CH₂CH₂CH₃; CON(CH₃)₂; 4-F], [1453: CH₂CH₂CH₃; CON(CH₃)₂; 4-Br], [1454: CH₂CH₂CH₃; CON(CH₃)₂; 4-I], [1455: CH₂CH₂CH₃; CON(CH₃)₂; 4-CN], [1456: CH₂CH₂CH₃; CON(CH₃)₂; 4-NO₂], [1457: CH₂CH₂CH₃; CON(CH₃)₂; 4-CF₃], [1458: CH₂CH₂CH₃; CON(CH₃)₂; 3-CF₃], [1459: CH₂CH₂CH₃; CON(CH₃)₂; 4-CF₂CF₃], [1460: CH₂CH₂CH₃; CON(CH₃)₂; 4-C≡CH], [1461: CH₂CH₂CH₃; CON(CH₃)₂; 4-OCF₃], [1462: CH₂CH₂CH₃; CON(CH₃)₂; 4-SCF₃], [1463: CH₂CH₂CH₃; CON(CH₃)₂; 4-SCH₃], [1464: CH₂CH₂CH₃; CON(CH₃)₂; 4-SOCH₃], [1465: CH₂CH₂CH₃; CON(CH₃)₂; 4-SO₂CH₃], [1466: CH₂CH₂CH₃; CON(CH₃)₂; 4-Cl-3-F], [1467: CH₂CH₂CH₃; CON(CH₃)₂; 4-Br-3-F], [1468: CH₂CH₂CH₃; CON(CH₃)₂; 3,4-(Cl)₂], [1469: CH₂CH₂CH₃; CON(CH₃)₂; 4-Cl-3-CF₃], [1470: CH₂CH₂CH₃; CON(CH₃)₂; 4-F-3-Cl], [1471: CF-1₂01-1₂CH₃; CON(CH₃)₂; 3,4,5-(F)₃], [1472: CH₂CH₂CH₃; CON(CH₃)₂; 4-Cl-3,5-(F)₂], [1473: CH₂CH₂CH₃; CON(CH₂CH₃)₂; 4-Cl], [1474: CH₂CH₂CH₃; CON(CH₂CH₃)₂; 3-Cl], [1475: CH₂CH₂CH₃; CON(CH₂CH₃)₂; 4-F], [1476: CH₂CH₂CH₃; CON(CH₂CH₃)₂; 4-Br], [1477: CH₂CH₂CH₃; CON(CH₂CH₃)₂; 4-I], [1478: CH₂CH₂CH₃; CON(CH₂CH₃)₂; 4-CN], [1479: CH₂CH₂CH₃; CON(CH₂CH₃)₂; 4-NO₂], [1480: CH₂CH₂CH₃; CON(CH₂CH₃)₂; 4-CF₃], [1481: CH₂CH₂CH₃; CON(CH₂CH₃)₂; 3-CF₃], [1482: CH₂CH₂CH₃; CON(CH₂CH₃)₂; 4-CF₂CF₃], [1483: CH₂CH₂CH₃; CON(CH₂CH₃)₂; 4-C≡CH], [1484: CH₂CH₂CH₃; CON(CH₂CH₃)₂; 4-OCF₃], [1485: CH₂CH₂CH₃; CON(CH₂CH₃)₂; 4-SCF₃], [1486: CH₂CH₂CH₃; CON(CH₂CH₃)₂; 4-SCH₃], [1487: CH₂CH₂CH₃; CON(CH₂CH₃)₂; 4-SOCH₃], [1488: CH₂CH₂CH₃; CON(CH₂CH₃)₂; 4-SO₂CH₃], [1489: CH₂CH₂CH₃; CON(CH₂CH₃)₂; 4-Cl-3-F], [1490: CH₂CH₂CH₃; CON(CH₂CH₃)₂; 4-Br-3-F], [1491: CH₂CH₂CH₃; CON(CH₂CH₃)₂; 3,4-(Cl)₂], [1492: CH₂CH₂CH₃; CON(CH₂CH₃)₂; 4-Cl-3-CF₃], [1493: CH₂CH₂CH₃; CON(CH₂CH₃)₂; 4-F-3-Cl], [1494: CH₂CH₂CH₃; CON(CH₂CH₃)₂; 3,4,5-(F)₃], [1495: CH₂CH₂CH₃; CON(CH₂CH₃)₂; 4-Cl-3,5-(F)₂], [1496: CH₂CH₂CH₃; CSNH₂; 4-Cl], [1497: CH₂CH₂CH₃; CSNH₂; 3-Cl], [1498: CH₂CH₂CH₃; CSNH₂; 4-F], [1499: CH₂CH₂CH₃; CSNH₂; 4-Br], [1500: CH₂CH₂CH₃; CSNH₂; 4I], [1501: CH₂CH₂CH₃; CSNH₂; 4-CN], [1502: CH₂CH₂CH₃; CSNH₂; 4-NO₂], [1503: CH₂CH₂CH₃; CSNH₂; 4-CF₃], [1504: CH₂CH₂CH₃; CSNH₂; 3-CF₃],

[1505: CH₂CH₂CH₃; CSNH₂; 4-CF₂CF₃], [1506: CH₂CH₂CH₃; CSNH₂; 4-C≡CH], [1507: CH₂CH₂CH₃; CSNH₂; 4-OCF₃], [1508: CH₂CH₂CH₃; CSNH₂; 4-SCF₃], [1509: CH₂CH₂CH₃; CSNH₂; 4-SCH₃], [1510: CH₂CH₂CH₃; CSNH₂; 4-SOCH₃], [1511: CH₂CH₂CH₃; CSNH₂; 4-SO₂CH₃], [1512: CH₂CH₂CH₃; CSNH₂; 4-Cl-3-F], [1513: CH₂CH₂CH₃; CSNH₂; 4-Br-3-F], [1514: CH₂CH₂CH₃; CSNH₂; 3,4-(Cl)₂], [1515: CH₂CH₂CH₃; CSNH₂; 4-Cl-3-CF₃], [1516: CH₂CH₂CH₃; CSNH₂; 4-F-3-Cl], [1517: CH₂CH₂CH₃; CSNH₂; 3,4,5-(F)₃], [1518: CH₂CH₂CH₃; CSNH₂; 4-Cl-3,5-(F)₂], [1519: CH₂CH₂CH₃; CSNHCH₃; 4-Cl], [1520: CH₂CH₂CH₃; CSNHCH₃; 3-Cl], [1521: CH₂CH₂CH₃; CSNHCH₃; 4-F], [1522: CH₂CH₂CH₃; CSNHCH₃; 4-Br], [1523: CH₂CH₂CH₃; CSNHCH₃; 4-I], [1524: CH₂CH₂CH₃; CSNHCH₃; 4-CN], [1525: CH₂CH₂CH₃; CSNHCH₃; 4-NO₂], [1526: CH₂CH₂CH₃; CSNHCH₃; 4-CF₃], [1527: CH₂CH₂CH₃; CSNHCH₃; 3-CF₃], [1528: CH₂CH₂CH₃; CSNHCH₃; 4-CF₂CF₃], [1529: CH₂CH₂CH₃; CSNHCH₃; 4-C≡CH], [1530: CH₂CH₂CH₃; CSNHCH₃; 4-OCF₃], [1531: CH₂CH₂CH₃; CSNHCH₃; 4-SCF₃], [1532: CH₂CH₂CH₃; CSNHCH₃; 4-SCH₃], [1533: CH₂CH₂CH₃; CSNHCH₃; 4-SOCH₃], [1534: CH₂CH₂CH₃; CSNHCH₃; 4-SO₂CH₃], [1535: CH₂CH₂CH₃; CSNHCH₃; 4-Cl-3-F], [1536: CH₂CH₂CH₃; CSNHCH₃; 4-Br-3-F], [1537: CH₂CH₂CH₃; CSNHCH₃; 3,4-(Cl)₂], [1538: CH₂CH₂CH₃; CSNHCH₃; 4-Cl-3-CF₃], [1539: CH₂CH₂CH₃; CSNHCH₃; 4-F-3-Cl], [1540: CH₂CH₂CH₃; CSNHCH₃; 3,4,5-(F)₃], [1541: CH₂CH₂CH₃; CSNHCH₃; 4-Cl-3,5-(F)₂], [1542: CH₂CH₂CH₃; CSNHCH₂CH₃; 4-Cl], [1543: CH₂CH₂CH₃; CSNHCH₂CH₃; 3-Cl], [1544: CH₂CH₂CH₃; CSNHCH₂CH₃; 4-F], [1545: CH₂CH₂CH₃; CSNHCH₂CH₃; 4-Br], [1546: CH₂CH₂CH₃; CSNHCH₂CH₃; 4-I], [1547: CH₂CH₂CH₃; CSNHCH₂CH₃; 4-CN], [1548: CH₂CH₂CH₃; CSNHCH₂CH₃; 4-NO₂], [1549: CH₂CH₂CH₃; CSNHCH₂CH₃; 4-CF₃], [1550: CH₂CH₂CH₃; CSNHCH₂CH₃; 3-CF₃], [1551: CH₂CH₂CH₃; CSNHCH₂CH₃; 4-CF₂CF₃], [1552: CH₂CH₂CH₃; CSNHCH₂CH₃; 4-C≡CH], [1553: CH₂CH₂CH₃; CSNHCH₂CH₃; 4-OCF₃], [1554: CH₂CH₂CH₃; CSNHCH₂CH₃; 4-SCF₃], [1555: CH₂CH₂CH₃; CSNHCH₂CH₃; 4-SCH₃], [1556: CH₂CH₂CH₃; CSNHCH₂CH₃; 4-SOCH₃], [1557: CH₂CH₂CH₃; CSNHCH₂CH₃; 4-SO₂CH₃], [1558: CH₂CH₂CH₃; CSNHCH₂CH₃; 4-Cl-3-F], [1559: CH₂CH₂CH₃; CSNHCH₂CH₃; 4-Br-3-F], [1560: CH₂CH₂CH₃; CSNHCH₂CH₃; 3,4-(Cl)₂], [1561: CH₂CH₂CH₃; CSNHCH₂CH₃; 4-Cl-3-CF₃], [1562: CH₂CH₂CH₃; CSNHCH₂CH₃; 4-F-3-Cl], [1563: CH₂CH₂CH₃; CSNHCH₂CH₃; 3,4,5-(F)₃], [1564: CH₂CH₂CH₃; CSNHCH₂CH₃; 4-Cl-3,5-(F)₂], [1565: CH₂CH₂CH₃; CSN(CH₃)₂; 4-Cl], [1566: CH₂CH₂CH₃; CSN(CH₃)₂; 3-Cl], [1567: CH2CH₂CH₃; CSN(CH₃)₂; 4-F], [1568: CH₂CH₂CH₃; CSN(CH₃)₂; 4-Br], [1569: CH₂CH₂CH₃; CSN(CH₃)₂; 4-I], [1570: CH₂CH₂CH₃; CSN(CH₃)₂; 4-CN], [1571: CH₂CH₂CH₃; CSN(CH₃)₂; 4-NO₂], [1572: CH₂CH₂CH₃; CSN(CH₃)₂; 4-CF₃], [1573: CH₂CH₂CH₃; CSN(CH₃)₂; 3-CF₃], [1574: CH₂CH₂CH₃; CSN(CH₃)₂; 4-CF₂CF₃], [1575: CH₂CH₂CH₃; CSN(CH₃)₂; 4-C≡CH], [1576: CH₂CH₂CH₃; CSN(CH₃)₂; 4-OCF₃], [1577: CH₂CH₂CH₃; CSN(CH₃)₂; 4-SCF₃], [1578: CH₂CH₂CH₃; CSN(CH₃)₂; 4-SCH₃], [1579: CH₂CH₂CH₃; CSN(CH₃)₂; 4-SOCH₃], [1580: CH₂CH₂CH₃; CSN(CH₃)₂; 4-SO₂CH₃], [1581: CH₂CH₂CH₃; CSN(CH₃)₂; 4-Cl-3-F], [1582: CH₂CH₂CH₃; CSN(CH₃)₂; 4-Br-3-F], [1583: CH₂CH₂CH₃; CSN(CH₃)₂; 3,4-(Cl)₂], [1584: CH₂CH₂CH₃; CSN(CH₃)₂; 4-Cl-3-CF₃], [1585: CH₂CH₂CH₃; CSN(CH₃)₂; 4-F-3-Cl], [1586: CH₂CH₂CH₃; CSN(CH₃)₂; 3,4,5-(F)₃], [1587: CH₂CH₂CH₃; CSN(CH₃)₂; 4-Cl-3,5-(F)₂], [1588: CH₂CH₂CH₃; CSN(CH₂CH₃)₂; 4-Cl], [1589: CH₂CH₂CH₃; CSN(CH₂CH₃)₂; 3-Cl], [1590: CH₂CH₂CH₃; CSN(CH₂CH₃)₂; 4-F], [1591: CH₂CH₂CH₃; CSN(CH₂CH₃)₂; 4-Br], [1592: CH₂CH₂CH₃; CSN(CH₂CH₃)₂; 4-I], [1593: CH₂CH₂CH₃; CSN(CH₂CH₃)₂; 4-CN], [1594: CH₂CH₂CH₃; CSN(CH₂CH₃)₂; 4-NO₂], [1595: CH₂CH₂CH₃; CSN(CH₂CH₃)₂; 4-CF₃], [1596: CH₂CH₂CH₃; CSN(CH₂CH₃)₂; 3-CF₃], [1597: CH₂CH₂CH₃; CSN(CH₂CH₃)₂; 4-CF₂CF₃], [1598: CH₂CH₂CH₃; CSN(CH₂CH₃)₂; 4-C≡CH], [1599: CH₂CH₂CH₃; CSN(CH₂CH₃)₂; 4-OCF₃], [1600: CH₂CH₂CH₃; CSN(CH₂CH₃)₂; 4-SCF₃], [1601: CH₂CH₂CH₃; CSN(CH₂CH₃)₂; 4-SCH₃], [1602: CH₂CH₂CH₃; CSN(CH₂CH₃)₂; 4-SOCH₃], [1603: CH₂CH₂CH₃; CSN(CH₂CH₃)₂; 4-SO₂CH₃], [1604: CH₂CH₂CH₃; CSN(CH₂CH₃)₂; 4-Cl-3-F], [1605: CH₂CH₂CH₃; CSN(CH₂CH₃)₂; 4-Br-3-F], [1606: CH₂CH₂CH₃; CSN(CH₂CH₃)₂; 3,4-(Cl)₂], [1607: CH₂CH₂CH₃; CSN(CH₂CH₃)₂; 4-Cl-3-CF₃], [1608: CH₂CH₂CH₃; CSN(CH₂CH₃)₂; 4-F-3-Cl], [1609: CH₂CH₂CH₃; CSN(CH₂CH₃)₂; 3,4,5-(F)₃], [1610: CH₂CH₂CH₃; CSN(CH₂CH₃)₂; 4-Cl-3,5-(F)₂], [1611: CH(CH₃)₂; CONH₂; 4-Cl], [1612: CH(CH₃)₂; CONH₂; 3-Cl], [1613: CH(CH₃)₂; CONH₂; 4-F], [1614: CH(CH₃)₂; CONH₂; 4-Br], [1615: CH(CH₃)₂; CONH₂; 4-I], [1616: CH(CH₃)₂; CONH₂; 4-CN], [1617: CH(CH₃)₂; CONH₂; 4-NO₂], [1618: CH(CH₃)₂; CONH₂; 4-CF₃], [1619: CH(CH₃)₂; CONH₂; 3-CF₃], [1620: CH(CH₃)₂; CONH₂; 4-CF₂CF₃], [1621: CH(CH₃)₂; CONH₂; 4-C≡CH], [1622: CH(CH₃)₂; CONH₂; 4-OCF₃], [1623: CH(CH₃)₂; CONH₂; 4-SCF₃], [1624: CH(CH₃)₂; CONH₂; 4-SCH₃], [1625: CH(CH₃)₂; CONH₂; 4-SOCH₃], [1626: CH(CH₃)₂; CONH₂; 4-SO₂CH₃], [1627: CH(CH₃)₂; CONH₂; 4-Cl-3-F], [1628: CH(CH₃)₂; CONH₂; 4-Br-3-F], [1629: CH(CH₃)₂; CONH₂; 3,4-(Cl)₂], [1630: CH(CH₃)₂; CONH₂; 4-Cl-3-CF₃], [1631: CH(CH₃)₂; CONH₂; 4-F-3-Cl], [1632: CH(CH₃)₂; CONH₂; 3,4,5-(F)₃], [1633: CH(CH₃)₂; CONH₂; 4-Cl-3,5-(F)₂], [1634: CH(CH₃)₂; CONHCH₃; 4-Cl], [1635: CH(CH₃)₂; CONHCH₃; 3-Cl], [1636: CH(CH₃)₂; CONHCH₃; 4-F], [1637: CH(CH₃)₂; CONHCH₃; 4-Br], [1638: CH(CH₃)₂; CONHCH₃; 4-I], [1639: CH(CH₃)₂; CONHCH₃; 4-CN], [1640: CH(CH₃)₂; CONHCH₃; 4-NO₂], [1641: CH(CH₃)₂; CONHCH₃; 4-CF₃], [1642: CH(CH₃)₂; CONHCH₃; 3-CF₃], [1643: CH(CH₃)₂; CONHCH₃; 4-CF₂CF₃], [1644: CH(CH₃)₂; CONHCH₃; 4-C≡CH], [1645: CH(CH₃)₂; CONHCH₃; 4-OCF₃], [1646: CH(CH₃)₂; CONHCH₃; 4-SCF₃], [1647: CH(CH₃)₂; CONHCH₃; 4-SCH₃], [1648: CH(CH₃)₂; CONHCH₃; 4-SOCH₃], [1649: CH(CH₃)₂; CONHCH₃; 4-SO₂CH₃], [1650: CH(CH₃)₂; CONHCH₃; 4-Cl-3-F], [1651: CH(CH₃)₂; CONHCH₃; 4-Br-3-F], [1652: CH(CH₃)₂; CONHCH₃; 3,4-(Cl)₂], [1653: CH(CH₃)₂; CONHCH₃; 4-Cl-3-CF₃], [1654: CH(CH₃)₂; CONHCH₃; 4-F-3-Cl], [1655: CH(CH₃)₂; CONHCH₃; 3,4,5-(F)₃], [1656: CH(CH₃)₂; CONHCH₃; 4-Cl-3,5-(F)₂], [1657: CH(CH₃)₂; CONHCH₂CH₃; 4-Cl], [1658: CH(CH₃)₂; CONHCH₂CH₃; 3-Cl], [1659: CH(CH₃)₂; CONHCH₂CH₃; 4-F], [1660: CH(CH₃)₂; CONHCH₂CH₃; 4-Br], [1661: CH(CH₃)₂; CONHCH₂CH₃; 4-I], [1662: CH(CH₃)₂; CONHCH₂CH₃;

4-CN], [1663: CH(CH₃)₃; CONHCH₂CH₃; 4-NO₂], [1664: CH(CH₃)₂; CONHCH₂CH₃; 4-CF₃], [1665: CH(CH₃)₂; CONHCH₂CH₃; 3-CF₃], [1666: CH(CH₃)₂; CONHCH₂CH₃; 4-CF₂CF₃], [1667: CH(CH₃)₂; CONHCH₂CH₃; 4-C≡CH], [1668: CH(CH₃)₂; CONHCH₂CH₃; 4-OCF₃], [1669: CH(CH₃)₂; CONHCH₂CH₃; 4-SCF₃], [1670: CH(CH₃)₂; CONHCH₂CH₃; 4-SCH₃], [1671: CH(CH₃)₂; CONHCH₂CH₃; 4-SOCH₃], [1672: CH(CH₃)₂; CONHCH₂CH₃; 4-SO₂CH₃], [1673: CH(CH₃)₂; CONHCH₂CH₃; 4-Cl-3-F], [1674: CH(CH₃)₃; CONHCH₂CH₃; 4-Br-3-F], [1675: CH(CH₃)₂; CONHCH₂CH₃; 3,4-(Cl)₂], [1676: CH(CH₃)₂; CONHCH₂CH₃; 4-Cl-3-CF₃], [1677: CH(CH₃)₂; CONHCH₂CH₃; 4-F-3-Cl], [1678: CH(CH₃)₂; CONHCH₂CH₃; 3,4,5-(F)₃], [1679: CH(CH₃)₂; CONHCH₂CH₃; 4-Cl-3,5-(F)₂], [1680: CH(CH₃)₂; CON(CH₃)₂; 4-Cl], [1681: CH(CH₃)₂; CON(CH₃)₂; 3-Cl], [1682: CH(CH₃)₂; CON(CH₃)₂; 4-F], [1683: CH(CH₃)₂; CON(CH₃)₂; 4-Br], [1684: CH(CH₃)₂; CON(CH₃)₂; 4-I], [1685: CH(CH₃)₂; CON(CH₃)₂; 4-CN], [1686: CH(CH₃)₂; CON(CH₃)₂; 4-NO₂], [1687: CH(CH₃)₂; CON(CH₃)₂; 4-CF₃], [1688: CH(CH₃)₂; CON(CH₃)₂; 3-CF₃], [1689: CH(CH₃)₂; CON(CH₃)₂; 4-CF₂CF₃], [1690: CH(CH₃)₂; CON(CH₃)₂; 4-C≡CH], [1691: CH(CH₃)₂; CON(CH₃)₂; 4-OCF₃], [1692: CH(CH₃)₂; CON(CH₃)₂; 4-SCF₃], [1693: CH(CH₃)₂; CON(CH₃)₂; 4-SCH₃], [1694: CH(CH₃)₂; CON(CH₃)₂; 4-SOCH₃], [1695: CH(CH₃)₂; CON(CH₃)₂; 4-SO₂CH₃], [1696: CH(CH₃)₂; CON(CH₃)₂; 4-Cl-3-F], [1697: CH(CH₃)₂; CON(CH₃)₂; 4-Br-3-F], [1698: CH(CH₃)₂; CON(CH₃)₂; 3,4-(Cl)₂], [1699: CH(CH₃)₂; CON(CH₃)₂; 4-Cl-3-CF₃], [1700: CH(CH₃)₂; CON(CH₃)₂; 4-F-3-Cl], [1701: CH(CH₃)₂; CON(CH₃)₂; 3,4,5-(F)₃], [1702: CH(CH₃)₂; CON(CH₃)₂; 4-Cl-3,5-(F)₂], [1703: CH(CH₃)₂; CON(CH₂CH₃)₂; 4-Cl], [1704: CH(CH₃)₂; CON(CH₂CH₃)₂; 3-Cl], [1705: CH(CH₃)₂; CON(CH₂CH₃)₂; 4-F], [1706: CH(CH₃)₂; CON(CH₂CH₃)₂; 4-Br], [1707: CH(CH₃)₂; CON(CH₂CH₃)₂; 4-I], [1708: CH(CH₃)₂; CON(CH₂CH₃)₂; 4-CN], [1709: CH(CH₃)₂; CON(CH₂CH₃)₂; 4-NO₂], [1710: CH(CH₃)₂; CON(CH₂CH₃)₂; 4-CF₃], [1711: CH(CH₃)₂; CON(CH₂CH₃)₂; 3-CF₃], [1712: CH(CH₃)₂; CON(CH₂CH₃)₂; 4-CF₂CF₃], [1713: CH(CH₃)₂; CON(CH₂CH₃)₂; 4-C≡CH], [1714: CH(CH₃)₂; CON(CH₂CH₃)₂; 4-OCF₃], [1715: CH(CH₃)₂; CON(CH₂CH₃)₂; 4-SCF₃], [1716: CH(CH₃)₂; CON(CH₂CH₃)₂; 4-SCH₃], [1717: CH(CH₃)₂; CON(CH₂CH₃)₂; 4-SOCH₃], [1718: CH(CH₃)₂; CON(CH₂CH₃)₂; 4-SO₂CH₃], [1719: CH(CH₃)₂; CON(CH₂CH₃)₂; 4-Cl-3-F], [1720: CH(CH₃)₂; CON(CH₂CH₃)₂; 4-Br-3-F], [1721: CH(CH₃)₂; CON(CH₂CH₃)₂; 3,4-(Cl)₂], [1722: CH(CH₃)₂; CON(CH₂CH₃)₂; 4-Cl-3-CF₃], [1723: CH(CH₃)₂; CON(CH₂CH₃)₂; 4-F-3-Cl], [1724: CH(CH₃)₂; CON(CH₂CH₃)₂; 3,4,5-(F)₃], [1725: CH(CH₃)₂; CON(CH₂CH₃)₂; 4-Cl-3,5-(F)₂], [1726: CH(CH₃)₂; CSNH₂; 4-Cl], [1727: CH(CH₃)₂; CSNH₂; 3-Cl], [1728: CH(CH₃)₂; CSNH₂; 4-F], [1729: CH(CH₃)₂; CSNH₂; 4-Br], [1730: CH(CH₃)₂; CSNH₂; 4-I], [1731: CH(CH₃)₂; CSNH₂; 4-ON], [1732: CH(CH₃)₂; CSNH₂; 4-NO₂], [1733: CH(CH₃)₂; CSNH₂; 4-CF₃], [1734: CH(CH₃)₂; CSNH₂; 3-CF₃], [1735: CH(CH₃)₂; CSNH₂; 4-CF₂CF₃], [1736: CH(CH₃)₂; CSNH₂; 4-C≡CH], [1737: CH(CH₃)₂; CSNH₂; 4-OCF₃], [1738: CH(CH₃)₂; CSNH₂; 4-SCF₃], [1739: CH(CH₃)₂; CSNH₂; 4-SCH₃], [1740: CH(CH₃)₂; CSNH₂; 4-SOCH₃], [1741: CH(CH₃)₂; CSNH₂; 4-SO₂CH₃], [1742: CH(CH₃)₂; CSNH₂; 4-Cl-3-F], [1743: CH(CH₃)₂; CSNH₂; 4-Br-3-F], [1744: CH(CH₃)₂; CSNH₂; 3,4-(Cl)₂], [1745: CH(CH₃)₂; CSNH₂; 4-Cl-3-CF₃], [1746: CH(CH₃)₂; CSNH₂; 4-F-3-Cl], [1747: CH(CH₃)₂; CSNH₂; 3,4,5-(F)₃], [1748: CH(CH₃)₂; CSNH₂; 4-Cl-3,5-(F)₂], [1749: CH(CH₃)₂; CSNHCH₃; 4-Cl], [1750: CH(CH₃)₂; CSNHCH₃; 3-Cl], [1751: CH(CH₃)₂; CSNHCH₃; 4-F], [1752: CH(CH₃)₂; CSNHCH₃; 4-Br], [1753: CH(CH₃)₂; CSNHCH₃; 4-I], [1754: CH(CH₃)₂; CSNHCH₃; 4-CN], [1755: CH(CH₃)₂; CSNHCH₃; 4-NO₂], [1756: CH(CH₃)₂; CSNHCH₃; 4-CF₃], [1757: CH(CH₃)₂; CSNHCH₃; 3-CF₃], [1758: CH(CH₃)₂; CSNHCH₃; 4-CF₂CF₃], [1759: CH(CH₃)₂; CSNHCH₃; 4-C≡CH], [1760: CH(CH₃)₂; CSNHCH₃; 4-OCF₃], [1761: CH(CH₃)₂; CSNHCH₃; 4-SCF₃], [1762: CH(CH₃)₂; CSNHCH₃; 4-SCH₃], [1763: CH(CH₃)₂; CSNHCH₃; 4-SOCH₃], [1764: CH(CH₃)₂; CSNHCH₃; 4-SO₂CH₃], [1765: CH(CH₃)₂; CSNHCH₃; 4-Cl-3-F], [1766: CH(CH₃)₂; CSNHCH₃; 4-Br-3-F], [1767: CH(CH₃)₂; CSNHCH₃; 3,4-(Cl)₂], [1768: CH(CH₃)₂; CSNHCH₃; 4-Cl-3-CF₃], [1769: CH(CH₃)₂; CSNHCH₃; 4-F-3-Cl], [1770: CH(CH₃)₂;CSNHCH₃; 3,4,5-(F)₃], [1771: CH(CH₃)₂;CSNHCH₃; 4-Cl-3,5-(F)₂], [1772: CH(CH₃)₂; CSNHCH₂CH₃; 4-Cl], [1773: CH(CH₃)₂; CSNHCH₂CH₃; 3-Cl], [1774: CH(CH₃)₂; CSNHCH₂CH₃; 4-F], [1775: CH(CH₃)₂; CSNHCH₂CH₃; 4-Br], [1776: CH(CH₃)₂; CSNHCH₂CH₃; 4-I], [1777: CH(CH₃)₂; CSNHCH₂CH₃; 4-CN], [1778: CH(CH₃)₂; CSNHCH₂CH₃; 4-NO₂], [1779: CH(CH₃)₂; CSNHCH₂CH₃; 4-CF₃], [1780: CH(CH₃)₂; CSNHCH₂CH₃; 3-CF₃], [1781: CH(CH₃)₂; CSNHCH₂CH₃; 4-CF₂CF₃], [1782: CH(CH₃)₂; CSNHCH₂CH₃; 4-C≡CH], [1783: CH(CH₃)₂; CSNHCH₂CH₃; 4-OCF₃], [1784: CH(CH₃)₂; CSNHCH₂CH₃; 4-SCF₃], [1785: CH(CH₃)₂; CSNHCH₂CH₃; 4-SCH₃], [1786: CH(CH₃)₂; CSNHCH₂CH₃; 4-SOCH₃], [1787: CH(CH₃)₂; CSNHCH₂CH₃; 4-SO₂CH₃], [1788: CH(CH₃)₂; CSNHCH₂CH₃; 4-Cl-3-F], [1789: CH(CH₃)₂; CSNHCH₂CH₃; 4-Br-3-F], [1790: CH(CH₃)₂; CSNHCH₂CH₃; 3,4-(Cl)₂], [1791: CH(CH₃)₂; CSNHCH₂CH₃; 4-Cl-3-CF₃], [1792: CH(CH₃)₂; CSNHCH₂CH₃; 4-F-3-Cl], [1793: CH(CH₃)₂; CSNHCH₂CH₃; 3,4,5-(F)₃], [1794: CH(CH₃)₂; CSNHCH₂CH₃; 4-Cl-3,5-(F)₂], [1795: CH(CH₃)₂; CSN(CH₃)₂; 4-Cl], [1796: CH(CH₃)₂; CSN(CH₃)₂; 3-Cl], [1797: CH(CH₃)₂; CSN(CH₃)₂; 4-F], [1798: CH(CH₃)₂; CSN(CH₃)₂; 4-Br], [1799: CH(CH₃)₂; CSN(CH₃)₂; 4-I], [1800: CH(CH₃)₂; CSN(CH₃)₂; 4-CN], [1801: CH(CH₃)₂; CSN(CH₃)₂; 4-NO₂], [1802: CH(CH₃)₂; CSN(CH₃)₂; 4-CF₃], [1803: CH(CH₃)₂; CSN(CH₃)₂; 3-CF₃], [1804: CH(CH₃)₂; CSN(CH₃)₂; 4-CF₂CF₃], [1805: CH(CH₃)₂; CSN(CH₃)₂; 4-C≡CH], [1806: CH(CH₃)₂; CSN(CH₃)₂; 4-OCF₃], [1807: CH(CH₃)₂; CSN(CH₃)₂; 4-SCF₃], [1808: CH(CH₃)₂; CSN(CH₃)₂; 4-SCH₃], [1809: CH(CH₃)₂; CSN(CH₃)₂; 4-SOCH₃], [1810: CH(CH₃)₂; CSN(CH₃)₂; 4-SO₂CH₃], [1811: CH(CH₃)₂; CSN(CH₃)₂; 4-Cl-3-F], [1812: CH(CH₃)₂; CSN(CH₃)₂; 4-Br-3-F], [1813: CH(CH₃)₂; CSN(CH₃)₂; 3,4-(Cl)₂], [1814: CH(CH₃)₂; CSN(CH₃)₂; 4-Cl-3-CF₃], [1815: CH(CH₃)₂; CSN(CH₃)₂; 4-F-3-Cl], [1816: CH(CH₃)₂; CSN(CH₃)₂; 3,4,5-(F)₃], [1817: CH(CH₃)₂; CSN(CH₃)₂; 4-Cl-3,5-(F)₂], [1818: CH(CH₃)₂; CSN(CH₂CH₃)₂; 4-Cl], [1819: CH(CH₃)₂; CSN(CH₂CH₃)₂; 3-Cl], [1820: CH(CH₃)₂; CSN(CH₂CH₃)₂; 4-F], [1821: CH(CH₃)₂; CSN(CH₂CH₃)₂; 4-Br], [1822: CH(CH₃)₂; CSN(CH₂CH₃)₂; 4-I], [1823: CH(CH₃)₂; CSN(CH₂CH₃)₂; 4-CN], [1824: CH(CH₃)₂; CSN(CH₂CH₃)₂; 4-NO₂], [1825: CH(CH₃)₂; CSN(CH₂CH₃)₂; 4-CF₃], [1826: CH(CH₃)₂; CSN(CH₂CH₃)₂;

3-CF₃], [1827: CH(CH₃)₂; CSN(CH₂CH₃)₂; 4-CF₂CF₃], [1828: CH(CH₃)₂; CSN(CH₂CH₃)₂; 4-C≡CH], [1829: CH(CH₃)₂; CSN(CH₂CH₃)₂; 4-OCF₃], [1830: CH(CH₃)₂; CSN(CH₂CH₃)₂; 4-SCF₃], [1831: CH(CH₃)₂; CSN(CH₂CH₃)₂; 4-SCH₃], [1832: CH(CH₃)₂; CSN(CH₂CH₃)₂; 4-SOCH₃], [1833: CH(CH₃)₂; CSN(CH₂CH₃)₂; 4-SO₂CH₃], [1834: CH(CH₃)₂; CSN(CH₂CH₃)₂; 4-Cl-3-F], [1835: CH(CH₃)₂; CSN(CH₂CH₃)₂; 4-Br-3-F], [1836: CH(CH₃)₂; CSN(CH₂CH₃)₂; 3,4-(Cl)₂], [1837: CH(CH₃)₂; CSN(CH₂CH₃)₂; 4-Cl-3-CF₃], [1838: CH(CH₃)₂; CSN(CH₂CH₃)₂; 4-F-3-Cl], [1839: CH(CH₃)₂;CSN(CH₂CH₃)₂; 3,4,5-(F)₃], [1840: CH(CH₃)₂;CSN(CH₂CH₃)₂; 4-Cl-3,5-(F)₂],

Among compounds defined by the above formulas (I-1) to (I-54) and the above combinations of R¹, R² and (R⁶)ₘ, for example, a compound defined by the formula (I-1) and the combination No. 855 (referred to as the compound (I-1-855)) and a compound defined by the formula (I-12) and the combination No. 723 (referred to as the compound (I-12-723)) are the following compounds.

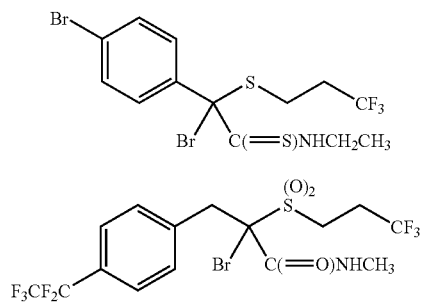

Then, Reference Production Examples for production of the intermediate compounds of the present invention are shown.

Reference Production Example 1

To a solution of 0.5 g of 5-bromo-1,2,3-trifluorobenzene and 0.72 g of methyl(3,3,3-trifluoropropylsulfonyl)acetate in 20 ml of 1,4-dioxane were added 0.28 g of sodium hydride (60% dispersion in paraffin liquid), 49 mg of tris(dibenzylideneacetone)(chloroform)dipalladium(0) and 75 mg of triphenylphosphine at room temperature, and the mixture was stirred at 80° C. for 48 hours. To the reaction mixture was added 10% hydrochloric acid, followed by extraction with ethyl acetate. The organic layer was dried over anhydrous sodium sulfate and concentrated under reduced pressure. The residue was subjected to silica gel column chromatography to obtain 0.54 g of methyl(3,4,5-trifluorophenyl)-(3,3,3-trifluoropropylsulfonyl)acetate represented by the following formula:

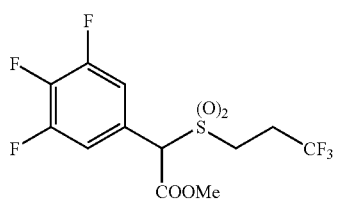

¹H-NMR (CDCl₃, TMS): δ (ppm) 7.29 (2H, dd), 4.95 (1H, s), 3.91 (3H, s) 3.18-3.56 (2H, m), 2.48-2.76 (2H, m).

Reference Production Example 2

To a suspension of 0.11 g of sodium hydride (60% dispersion in paraffin liquid) in 30 ml of tetrahydrofuran was added 1.0 g of methyl(3,4,5-trifluorophenyl)-(3,3,3-trifluoropropylsulfonyl)acetate at room temperature. The mixture was stirred at room temperature for 0.5 hour and thereto 0.79 g of 1-fluoro-2,4,6-trimethylpyridinium trifluoromethanesulfonate was added. The reaction mixture was stirred at the same temperature for 2 hours, and thereto 10% hydrochloric acid was added, followed by extraction with ethyl acetate. The organic layer was dried over anhydrous sodium sulfate and concentrated under reduced pressure. The residue was subjected to silica gel column chromatography to obtain 0.99 g of methyl fluoro-(3,4,5-trifluorophenyl)-(3,3,3-trifluoropropylsulfonyl)acetate represented by the following formula:

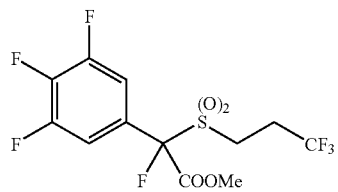

¹H-NMR (CDCl₃, TMS): δ (ppm) 7.50 (2H, dd), 4.00 (3H, s) 3.33-3.46 (2H, m), 2.61-2.76 (2H, m).

Reference Production Example 3

To a suspension of 0.11 g of sodium hydride (60% dispersion in paraffin liquid) in 30 ml of N,N-dimethylformamide was added 1.0 g of methyl(3,4,5-trifluorophenyl)-(3,3,3-trifluoropropylsulfonyl)acetate at room temperature. The mixture was stirred at room temperature for 0.5 hour and thereto 0.39 g of methyl iodide was added. The reaction mixture was stirred at the same temperature for 48 hours and, thereto 10% hydrochloric acid was added, followed by extraction with ethyl acetate. The organic layer was dried over anhydrous sodium sulfate and concentrated under reduced pressure. The residue was subjected to silica gel column chromatography to obtain 0.92 g of methyl 2-(3,4,5-trifluorophenyl)-2-(3,3,3-trifluoropropylsulfonyl)propanoate represented by the following formula:

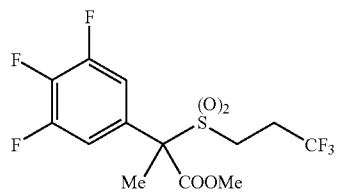

¹H-NMR (CDCl₃, TMS): δ (ppm) 7.20 (2H, dd), 3.94 (3H, s), 3.05-3.70 (2H, m), 2.39-2.73 (2H, m), 2.04 (3H, s).

Reference Production Example 4

To a solution of 3.0 g of 2-fluoro-4-iodochlorobenzene and 3.6 g of methyl(3,3,3-trifluoropropylsulfonyl)acetate in 100 ml of 1,4-dioxane were added 1.40 g of sodium hydride (60% dispersion in paraffin liquid), 242 mg of (dibenzylideneacetone)(chloroform)dipalladium(0) and 368 mg of triphenylphosphine at room temperature, and the mixture was stirred at 80° C. for 5 days. To the reaction mixture was added 10% hydrochloric acid, followed by extraction with ethyl acetate. The organic layer was dried over anhydrous sodium sulfate and concentrated under reduced pressure. The residue was subjected to silica gel column chromatography to obtain 1.8 g of methyl(4-chloro-3-fluorophenyl)-(3,3,3-trifluoropropylsulfonyl)acetate represented by the following formula:

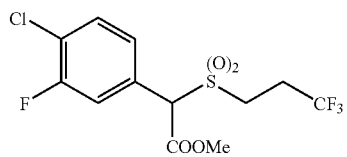

$^1$H-NMR (CDCl$_3$, TMS): δ (ppm) 7.43-7.53 (2H, m), 7.31 (1H, dd), 5.02 (1H, s), 3.90 (3H, s), 3.17-3.58 (2H, m), 2.44-2.77 (2H, m).

Reference Production Example 5

To a suspension of 0.11 g of sodium hydride (60% dispersion in paraffin liquid) in 30 ml of tetrahydrofuran was added 1.0 g of methyl(4-chloro-3-fluorophenyl)-(3,3,3-trifluoropropylsulfonyl)acetate at room temperature. The mixture was stirred at room temperature for 0.5 hour and thereto 0.79 g of 1-fluoro-2,4,6-trimethylpyridinium trifluoromethanesulfonate was added. The reaction mixture was stirred at the same temperature for 2 hours, and thereto 10% hydrochloric acid was added, followed by extraction with ethyl acetate. The organic layer was dried over anhydrous sodium sulfate and concentrated under reduced pressure. The residue was subjected to silica gel column chromatography to obtain 0.99 g of methyl(4-chloro-3-fluorophenyl)-fluoro-(3,3,3-trifluoropropylsulfonyl)acetate represented by the following formula:

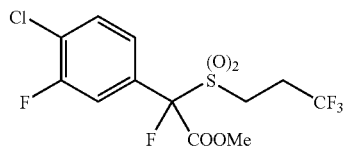

$^1$H-NMR (CDCl$_3$, TMS): δ (ppm) 7.52-7.66 (3H, m), 4.00 (3H, s), 3.28-3.38 (2H, m), 2.58-2.73 (2H, m).

Reference Production Example 6

To a solution of 2.8 g of 4-iodochlorobenzene and 3.56 g of methyl(3,3,3-trifluoropropylsulfonyl)acetate in 100 ml of 1,4-dioxane were added 1.4 g of sodium hydride (60% dispersion in paraffin liquid), 242 mg of tris(dibenzylideneacetone)(chloroform)dipalladium(0) and 368 mg of triphenylphosphine at room temperature, and the mixture was stirred at 80° C. for 48 hours. To the reaction mixture was added 10% hydrochloric acid, followed by extraction with ethyl acetate. The organic layer was dried over anhydrous sodium sulfate and concentrated under reduced pressure. The residue was subjected to silica gel column chromatography to obtain 2.6 g of methyl(4-chlorophenyl)-(3,3,3-trifluoropropylsulfonyl)acetate represented by the following formula:

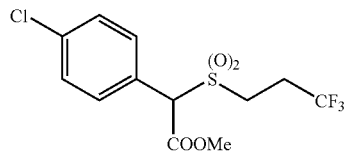

$^1$H-NMR (CDCl$_3$, TMS): δ (ppm) 7.53 (2H, d), 7.44 (2H, d), 5.05 (1H, s), 3.88 (3H, s), 3.15-3.55 (2H, m), 2.40-2.73 (2H, m).

Reference Production Example 7

To a suspension of 81 mg of sodium hydride (60% dispersion in paraffin liquid) in 30 ml of tetrahydrofuran was added 0.7 g of methyl(4-chlorophenyl)-(3,3,3-trifluoropropylsulfonyl)-acetate at room temperature. The mixture was stirred at room temperature for 0.5 hour and thereto 0.59 g of 1-fluoro-2,4,6-trimethylpyridinium trifluoromethanesulfonate was added. The reaction mixture was stirred at the same temperature for 2 hours, and thereto 10% hydrochloric acid was added, followed by extraction with ethyl acetate. The organic layer was dried over anhydrous sodium sulfate and concentrated under reduced pressure. The residue was subjected to silica gel column chromatography to obtain 0.67 g of methyl (4-chlorophenyl)-fluoro-(3,3,3-trifluoropropylsulfonyl)acetate represented by the following formula:

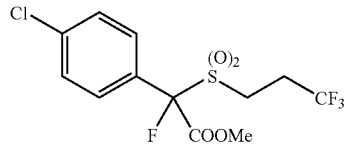

$^1$H-NMR (CDCl$_3$, TMS): δ (ppm) 7.74 (2H, dd), 7.49 (2H, dd), 3.99 (3H, s), 3.24-3.38 (2H, m), 2.52-2.72 (2H, m).

Reference Production Example 8

To a solution of 5.0 g of 4-trifluoromethyliodobenzene and 5.6 g of methyl(3,3,3-trifluoropropylsulfonyl)acetate in 100 ml of 1,4-dioxane were added 2.21 g of sodium hydride (60% dispersion in paraffin liquid), 579 mg of tris(dibenzylideneacetone)(chloroform)dipalladium(0) and 381 mg of triphenylphosphine at room temperature, and the mixture was stirred at 80° C. for 20 hours. To the reaction mixture was added 10% hydrochloric acid, followed by extraction with ethyl acetate. The organic layer was dried over anhydrous sodium sulfate and concentrated under reduced pressure. The residue was subjected to silica gel column chromatography to obtain 4.2 g of methyl(4-trifluoromethylphenyl)-(3,3,3-trifluoropropylsulfonyl)acetate represented by the following formula:

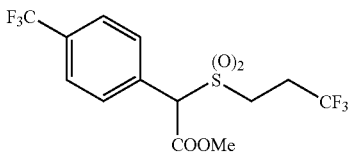

¹H-NMR (CDCl₃, TMS): δ (ppm) 7.73 (4H, s), 5.11 (1H, s), 3.90 (3H, s), 3.15-3.58 (2H, m), 2.43-2.75 (2H, m).

Reference Production Example 9

To a suspension of 106 mg of sodium hydride (60% dispersion in paraffin liquid) in 30 ml of tetrahydrofuran was added 1.0 g of methyl(4-trifluoromethylphenyl)-(3,3,3-trifluoropropylsulfonyl)-acetate at room temperature. The mixture was stirred at room temperature for 0.5 hour and thereto 0.77 g of 1-fluoro-2,4,6-trimethylpyridinium trifluoromethanesulfonate was added. The reaction mixture was stirred at the same temperature for 10 hours, and thereto 10% hydrochloric acid was added, followed by extraction with ethyl acetate. The organic layer was dried over anhydrous sodium sulfate and concentrated under reduced pressure. The residue was subjected to silica gel column chromatography to obtain 0.92 g of methyl fluoro-(4-trifluoromethylphenyl)-(3,3,3-trifluoropropylsulfonyl)acetate represented by the following formula:

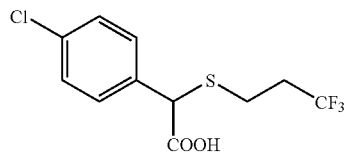

¹H-NMR (CDCl₃, TMS): δ (ppm) 7.96 (2H, d), 7.78 (2H, d) 4.00 (3H, s), 3.28-3.42 (2H, m), 2.56-2.80 (2H, m).

Reference Production Example 10

To a solution of 1.78 g of S-(3,3,3-trifluoropropyl)benzenethioate in 30 ml of tetrahydrofuran was added dropwise 1.5 ml of sodium methoxide (28% methanol solution) at room temperature, and then 2.0 g of methyl bromo-(4-chlorophenyl)acetate at room temperature. The mixture was stirred at the same temperature for 4 hours. To the reaction mixture was added 10% hydrochloric acid, followed by extraction with ethyl acetate. The organic layer was dried over anhydrous sodium sulfate and concentrated under reduced pressure. The residue was subjected to silica gel column chromatography to obtain 2.2 g of methyl(4-chlorophenyl)-(3,3,3-trifluoropropylsulfanyl)acetate represented by the following formula:

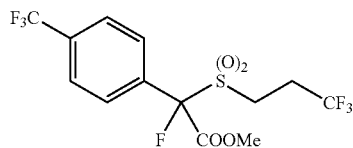

¹H-NMR (CDCl₃, TMS): δ (ppm) 7.40 (2H, dd), 7.34 (2H, dd) 4.57 (1H, s), 3.76 (3H, s), 2.61-2.78 (2H, m) 2.25-2.42 (2H, m).

Reference Production Example 11

To a solution of 1.88 g of methyl(4-chlorophenyl)-(3,3,3-trifluoropropylsulfanyl)acetate in 10 ml of methanol was added 5.0 ml of an aqueous 10% sodium hydroxide solution at room temperature, and the mixture was stirred at the same temperature for 0.5 hour. To the reaction mixture was added 12% hydrochloric acid, followed by extraction with ethyl acetate. The organic layer was dried over anhydrous sodium sulfate and concentrated under reduced pressure. The residue was subjected to silica gel column chromatography to obtain 1.70 g of (4-chlorophenyl)-(3,3,3-trifluoropropylsulfanyl) acetic acid represented by the following formula:

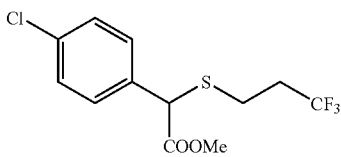

¹H-NMR (CDCl₃, TMS): δ (ppm) 7.41-7.35 (4H, m), 4.56 (1H, S), 2.80-2.67 (2H, m), 2.41-2.26 (2H, m).

Reference Production Example 12

To a suspension of 349 mg of sodium hydride (55% dispersion in paraffin liquid) in 6.0 ml of tetrahydrofuran was added dropwise a solution of 1.87 g of methyl(3,3,3-trifluoropropylsulfonyl)acetate in 3.0 ml of tetrahydrofuran at room temperature, and the mixture was stirred at the same temperature for 0.5 hour. Thereto a solution of 1.91 g of 4-trifluoromethylbenzyl bromide in 6.0 ml of tetrahydrofuran was added. The reaction mixture was stirred at room temperature for 4 hours, and thereto 12% hydrochloric acid was added, followed by extraction with ethyl acetate. The organic layer was dried over anhydrous sodium sulfate and concentrated under reduced pressure. The residue was subjected to silica gel column chromatography to obtain 1.80 g of methyl 3-(4-trifluoromethylphenyl)-2-(3,3,3-trifluoropropylsulfonyl)propanoate represented by the following formula:

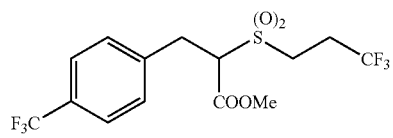

¹H-NMR (CDCl₃, TMS): δ (ppm) 7.60 (2H, d), 7.35 (2H, d), 4.11 (1H, dd), 3.76 (3H, s), 3.57-3.33 (4H, m), 2.80-2.66 (2H, m).

Reference Production Example 13

To a suspension of 104 mg of sodium hydride (55% dispersion in paraffin liquid) in 3.0 ml of tetrahydrofuran was added a solution of 0.85 g of methyl 3-(4-trifluoromethylphenyl)-2-(3,3,3-trifluoropropylsulfonyl)propanoate in 5.0 ml of tetrahydrofuran at room temperature. The mixture was stirred at room temperature for 0.5 hour, and thereto a solution of 0.42 g of N-chlorosuccinimide in 6.0 ml of tetrahydrofuran was added at room temperature. The reaction mixture was stirred at the same temperature for 19 hours, and thereto 10% hydrochloric acid was added, followed by extraction with ethyl acetate. The organic layer was dried over anhydrous sodium sulfate and concentrated under reduced pressure. The residue was subjected to silica gel column chromatography to obtain 0.33 g of methyl 2-chloro-3-(4-trifluoromethylphenyl)-2-(3,3,3-trifluoropropylsulfonyl)propanoate represented by the following formula:

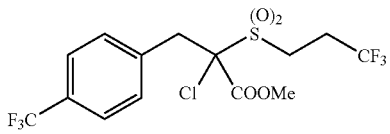

¹H-NMR (CDCl₃, TMS): δ (ppm) 7.60 (2H, d), 7.47 (2H, d), 4.05 (1H, d), 3.91 (3H, s), 3.81-3.72 (1H, m), 3.55 (1H, d), 3.54-3.50 (1H, m), 2.80-2.71 (2H, m).

Reference Production Example 14

To a suspension of 0.16 g of sodium hydride (55% dispersion in paraffin liquid) in 6.0 ml of tetrahydrofuran was added dropwise a solution of 0.95 g of methyl(3,3,3-trifluoropropylsulfonyl)acetate in 3.0 ml of tetrahydrofuran at room temperature, and the mixture was stirred at the same temperature for 0.5 hour. Thereto a solution of 0.94 g of 3-trifluoromethylbenzyl bromide in 6.0 ml of tetrahydrofuran was added. The reaction mixture was stirred at room temperature for 3 hours, and thereto 12% hydrochloric acid was added, followed by extraction with ethyl acetate. The organic layer was dried over anhydrous sodium sulfate and concentrated under reduced pressure. The residue was subjected to silica gel column chromatography to obtain 0.38 g of methyl 3-(3-trifluoromethylphenyl)-2-(3,3,3-trifluoropropylsulfonyl)propanoate represented by the following formula:

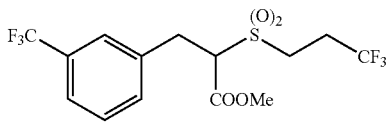

¹H-NMR (CDCl₃, TMS): δ (ppm) 7.57-7.56 (1H, m), 7.50-7.41 (3H, m), 4.10 (1H, dd), 3.75 (3H, s), 3.54 (1H, dd), 3.52-3.45 (1H, m), 3.44 (1H, dd), 3.42-3.32 (1H, m), 2.79-2.67 (2H, m).

Reference Production Example 15

To a suspension of 47 mg of sodium hydride (55% dispersion in paraffin liquid) in 3.0 ml of tetrahydrofuran was added a solution of 0.38 g of methyl 3-(3-trifluoromethylphenyl)-2-(3,3,3-trifluoropropylsulfonyl)propanoate in 5.0 ml of tetrahydrofuran at room temperature, and the mixture wad stirred at room temperature for 0.5 hour. Thereto a solution of 0.14 g of N-chlorosuccinimide in 6.0 ml of tetrahydrofuran was added at room temperature. The reaction mixture was stirred at the same temperature for 2 hours, and thereto 10% hydrochloric acid was then added, followed by extraction with ethyl acetate. The organic layer was dried over anhydrous sodium sulfate and concentrated under reduced pressure. The residue was subjected to silica gel column chromatography to obtain 0.31 g of methyl 2-chloro-3-(3-trifluoromethylphenyl)-2-(3,3,3-trifluoropropylsulfonyl)propanoate represented by the following formula:

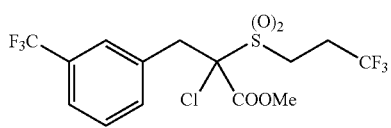

¹H-NMR (CDCl₃, TMS): δ (ppm) 7.58-7.48 (4H, m), 4.05 (1H, d), 3.90 (3H, s), 3.79-3.76 (1H, m), 3.55 (1H, d), 3.54-3.50 (1H, m), 2.82-2.69 (2H, m).

Reference Production Example 16

To a suspension of 349 mg of sodium hydride (55% dispersion in paraffin liquid) in 6.0 ml of tetrahydrofuran was added dropwise a solution of 1.87 g of methyl(3,3,3-trifluoropropylsulfonyl)acetate in 3.0 ml of tetrahydrofuran at room temperature, and the mixture was stirred at the same temperature for 0.5 hour. Thereto a solution of 1.99 g of 2-trifluoromethylbenzyl bromide in 6.0 ml of tetrahydrofuran was added. The reaction mixture was stirred at room temperature for 4 hours, and thereto 12% hydrochloric acid was added, followed by extraction with ethyl acetate. The organic layer was dried over anhydrous sodium sulfate and concentrated under reduced pressure. The residue was subjected to silica gel column chromatography to obtain 1.79 g of methyl 3-(2-trifluoromethylphenyl)-2-(3,3,3-trifluoropropylsulfonyl)propanoate represented by the following formula:

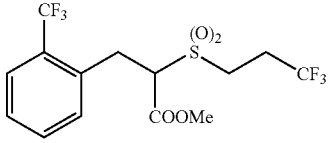

¹H-NMR (CDCl₃, TMS): δ (ppm) 7.70 (1H, d), 7.51 (1H, t), 7.42 (1H,t), 7.37 (1H, d), 4.16 (1H, dd), 3.76 (3H, s), 3.73 (1H, dd), 3.55-3.32 (3H, m), 2.75-2.69 (2H, m).

Reference Production Example 17

To a suspension of 206 mg of sodium hydride (55% dispersion in paraffin liquid) in 3.0 ml of tetrahydrofuran was added a solution of 1.21 g of methyl 3-(2-trifluoromethylphenyl)-2-(3,3,3-trifluoropropylsulfonyl)propanoate in 5.0 ml of tetrahydrofuran at room temperature, and the mixture was stirred at room temperature for 0.5 hour. Thereto a solution of 0.82 g of N-chlorosuccinimide in 6.0 ml of tetrahydrofuran was added at room temperature. The reaction mixture was stirred at the same temperature for 7 hours, and thereto 10% hydrochloric acid was then added, followed by extraction with ethyl acetate. The organic layer was dried over anhydrous sodium sulfate and concentrated under reduced pressure. The residue was subjected to silica gel column chromatography to obtain 0.72 g of methyl 2-chloro-3-(2-trifluoromethylphenyl)-2-(3,3,3-trifluoropropylsulfonyl)propanoate represented by the following formula:

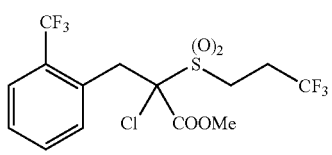

$^1$H-NMR (CDCl$_3$, TMS): δ (ppm) 7.73-7.71 (1H, m), 7.53-7.51 (1H, m), 7.45-7.38 (2H, m), 4.26 (1H, d), 3.91 (3H, s), 3.88 (1H, d), 3.82-3.78 (1H, m), 3.59-3.55 (1H, m), 2.84-2.71 (2H, m).

Next, Formulation Example is shown. The term "part(s)" means part(s) by weight. The compounds of the present invention are represented by the compound numbers as described above.

Formulation Example 1

Nine parts of any one of the present compounds (1) to (10) is dissolved in a mixture of 37.5 parts of xylene and 37.5 parts of N,N-dimethylformamide. Thereto 10 parts of polyoxyethylene styryl phenyl ether and 6 parts of calcium dodecylbenzenesulfonate are added, and mixed by stirring thoroughly to obtain an emulsifiable concentrate.

Formulation Example 2

Five parts of the present compound (1) and 4 parts of a compound selected from the following group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

The Group [A]:

aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos;

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb;

acrinathrin, allethrin, beta-cyfluthrin, bifenthrin, cyclopro-thrin, cyfluthrin, cyhalothrin, empenthrin, deltamethrin, esfenvalerate, ethofenprox, fenvalerate, flucythrinate, flufenoprox, flumethrin, fluvalinate, halfenprox, imiprothrin, prallethrin, pyrethrins, resmethrin, sigma-cypermethrin, silafluofen, tefluthrin, tralomethrin, transfluthrin, tetramethrin, lambda-cyhalothrin, gamma-cyhalothrin, furamethrin, tau-fluvalinate, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl) cyclopropanecarboxylate, 2,3,5,6-tetrafluoro-4-(methoxymethyl)benzyl 2,2,3,3-tetramethylcyclopropanecarboxylate;

cartap, bensultap, thiocyclam, monosultap, bisultap;

imidacloprid, nitenpyram, acetamiprid, thiamethoxam, thiacloprid;

chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron;

acetoprole, fipronil, vaniliprole, pyriprole, pyrafluprole;

chromafenozide, halofenozide, methoxyfenozide, tebufenozide;

aldrin, dieldrin, dienochlor, endosulfan, methoxychlor;

nicotine sulfate;

avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, chlorantraniliprole, tralopyril, a compound represented by the following formula (A):

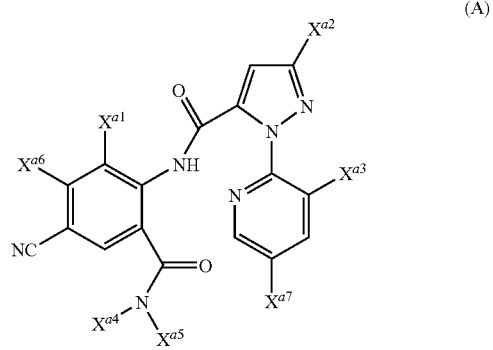

wherein $X^{a1}$ represents a methyl group, a chlorine atom, a bromine atom or a fluorine atom, $X^{a2}$ represents a fluorine atom, a chlorine atom, a bromine atom, a C1-C4 haloalkyl grop or a C1-C4 haloalkoxy group, $X^{a3}$ represents a fluorine atom, a chlorine atom or a bromine atom, $X^{a4}$ represents an optionally substituted C1-C4 alkyl group, an optionally substituted C3-C4 alkenyl group, an optionally substituted C3-C4 alkynyl group, an optionally substituted C3-C5 cycloalkylalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom, a compound represented by the following formula (B):

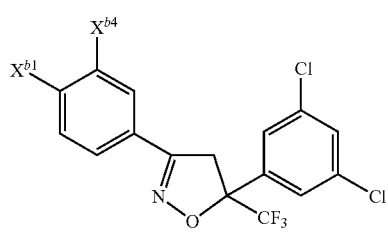

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group, or an optionally substituted 1,2,4-triazol-1-yl group, $X^{b2}$ represents an optionally substituted C1-C4 haloalkyl group such as a 2,2,2-trifluoroethyl group, or an optionally substituted C3-C6 cycloalkyl group such as a cyclopropyl group, $X^{b3}$ represents an optionally substituted C1-C4 alkyl group such as a methyl group, and $X^{b4}$ represents a hydrogen atom, a chlorine atom, a cyano group or a methyl group, a compound represented by the following formula (C):

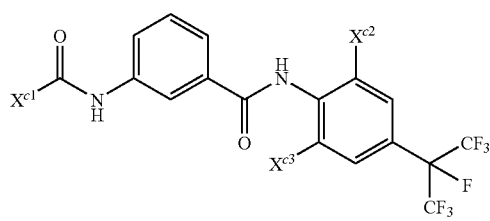

(C)

wherein $X^{c1}$ represents an optionally substituted C1-C4 alkyl group such as a 3,3,3-trifluoropropyl group, an optionally substituted C1-C4 alkoxy group such as a 2,2,2-trichloroethoxy group, an optionally substituted phenyl group such as a 4-cyanophenyl group, or an optionally substituted pyridyl group such as a 2-chloro-3-pyridyl group, $X^{c2}$ represents a methyl group or a trifluoromethylthio group, and $X^{c3}$ represents a methyl group or a halogen atom, acequinocyl, amitraz, benzoximate, bifenazate, bromopropylate, chinomethionat, chlorobenzilate, CPCBS (chlorfenson), clofentezine, cyflumetofen, kelthane (dicofol), fenbutatin oxide, fenothiocarb, fenpyroximate, fluacrypyrim, fluproxyfen, hexythiazox, propargite (BPPS), pyridaben, pyrimidifen, tebufenpyrad, tetradifon, spirodiclofen, spiromesifen, spirotetramat, amidoflumet, and cyenopyrafen.

Formulation Example 3

Five parts of the present compound (2) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 4

Five parts of the present compound (3) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 5

Five parts of the present compound (4) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 6

Five parts of the present compound (5) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 7

Five parts of the present compound (6) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 8

Five parts of the present compound (7) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 9

Five parts of the present compound (8) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 10

Five parts of the present compound (9) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 11

Five parts of the present compound (10) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 12

Five parts of SORPOL 5060 (registered trade name for TOHO Chemical Industry Co., LTD.) is added to 40 parts of any one of the present compounds (1) to (10) and mixed thoroughly. Then, 32 parts of CARPLEX #480 (registered trade name for Shionogi & Co., Ltd., synthetic hydrous silicon oxide fine powder) and 23 parts of 300 mesh diatomaceous earth are added thereto and mixed with a juice mixer to obtain a wettable powder.

Formulation Example 13

Three parts of any one of the present compounds (1) to (10), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 14

Four point five parts of any one of the present compounds (1) to (10), 1 part of synthetic hydrous silicon oxide fine powder, 1 part of Dorires B (manufactured by Sankyo) as a flocculant, and 7 parts of clay are mixed thoroughly with a mortar and then by stirring with a juice mixer. To the resultant mixture 86.5 parts of cut clay is added and mixed by stirring thoroughly to obtain a dust.

Formulation Example 15

Ten parts of any one of the present compounds (1) to (10), 35 parts of a mixture of white carbon with polyoxyethylene alkylether sulfate ammonium salt (weight ratio 50/50), and 55 parts of water are mixed and then finely-divided by a wet grinding method to obtain a formulation.

Formulation Example 16

Zero point five part of any one of the present compounds (1) to (10) is dissolved in 10 parts of dichloromethane. This solution is mixed with 89.5 parts of Isopar M (isoparaffin: registered trade name for Exxon Chemical) to obtain an oil solution.

Formulation Example 17

Zero point one part of any one of the present compounds (1) to (10) and 49.9 parts of NEO-THIOZOL (Chuo Kasei Co., Ltd.) are placed in an aerosol can. An aerosol valve is fitted to the can and the can is then charged with 25 parts of dimethyl ether and 25 parts of LPG. An actuator is fitted to the can to obtain an oily aerosol.

Formulation Example 18

An aerosol container is charged with 0.6 parts of any one of the present compounds (1) to (10), 0.01 part of BHT, 5 parts of xylene, a mixture of 3.39 parts of a deodorized kerosine and 1 part of an emulsifying agent [Atmos 300 (registered trade name for Atmos Chemical Ltd.)] and 50 parts of distilled water. A valve part is attached to the container and the container is then charged with 40 parts of a propellant (LPG) through the valve under increased pressure to obtain an aqueous aerosol.

Formulation Example 19

Five parts of any one of the present compounds (1) to (10) is dissolved in 80 parts of diethylene glycol monoethyl ether. Thereto 15 parts of propylene carbonate is mixed to obtain a spot-on liquid formulation.

Formulation Example 20

Ten parts of any one of the present compounds (1) to (10) is dissolved in 70 parts of diethylene glycol monoethyl ether. Thereto 20 parts of 2-octyldodecanol is mixed to obtain a pour-on liquid formulation.

Formulation Example 21

To 0.5 parts of any one of the present compounds (1) to (10) are added 60 parts of NIKKOL TEALS-42 (a 42% aqueous solution of triethanolamine lauryl sulfate, Nikko Chemicals) and 20 parts of propylene glycol. The mixture is stirred well to obtain a homogeneous solution. Thereto 19.5 parts of water is added and mixed by stirring thoroughly to obtain a homogeneous shampoo formulation.

Formulation Example 22

A porous ceramic plate with a length of 4.0 cm, a width of 0.4 cm and a thickness of 1.2 cm is impregnated with a solution of 0.1 g of any one of the present compounds (1) to (10) in 2 ml of propylene glycol to obtain a heating-type smoking pesticide.

Formulation Example 23

Five parts of any one of the present compounds (1) to (10) and 95 parts of an ethylene-methyl methacrylate copolymer (the proportion of methyl methacrylate in the copolymer: 10% by weight, ACRYFT WD301, Sumitomo Chemical) are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Formulation Example 24

Five parts of any one of the present compounds (1) to (10) and 95 parts of a flexible polyvinyl chloride resin are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Next, effectiveness of the compound of the present invention as the active ingredient of a pesticidal composition is shown by Test Examples.

Test Example 1

A formulation of any one of the present compounds (1) to (10) obtained according to Formulation Example 15 was diluted so that the active ingredient concentration was 500 ppm to obtain a test solution.

At the same time, 50 g of culture soil, Bonsol No. 2 (manufactured by Sumitomo Chemical Co., Ltd.) was put into a polyethylene cup, and 10 to 15 seeds of rice were planted therein. The rice plants were grown until the second foliage leaf was developed, and then cut so as to have the same height of 5 cm. The test solution was sprayed on the rice plants in an amount of 20 ml/cup. After the test solution sprayed on the rice plants was dried, the rice plants were placed in a plastic cup for the purpose of preventing test worms from escaping. Thirty first-instar larvae of brown rice planthopper were released into the cup, and the cup was sealed with a lid. Then the cup was placed in a greenhouse at 25° C. for 6 days. Then, the number of parasitic brown rice planthoppers on the rice plants was examined.

As a result, on the plants treated with any one of the present compounds (1), (2), (3), (4), (5) and (6), the number of the parasitic pests was 3 or smaller.

Test Example 2

A formulation of any one of the present compounds (1) to (10) obtained according to Formulation Example 15 was diluted so that the active ingredient concentration was 55.6 ppm to obtain a test solution.

At the same time, 50 g of culture soil, Bonsol No. 2 (manufactured by Sumitomo Chemical Co., Ltd.) was put into a polyethylene cup with five holes of 5 mm diameter at the bottom, and 10 to 15 seeds of rice were planted therein. The rice plants were grown until the second foliage leaf was developed, and then treated with 45 ml of the test solution by allowing the plants to absorb the test solution from the bottom of the cup. The rice plants were placed in a greenhouse at 25° C. for 6 days and then cut into the same height of 5 cm. Thirty first-instar larvae of brown rice planthopper were released into the greenhouse at 25° C. and left for 6 days. Then, the number of parasitic brown rice planthoppers on the rice plants was examined.

As a result, on the plants treated with any one of the present compounds (1), (2), (3), (4), (5), (6) and (7), the number of the parasitic pests was 3 or smaller.

Test Example 3

A formulation of any one of the present compounds (1) to (10) obtained according to Formulation Example 15 was diluted with water so that the active ingredient concentration was 500 ppm to obtain a test solution.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 10 female imagoes of Musca domestica were released and the cup was sealed with a lid. After 24 hours, the number of surviving Musca domestica was examined and the death rate of the pest was calculated.

As a result, the treatments with any one of the present compounds (1), (3), (4) and (5) showed a pest death rate of 90% or more. The treatments with any one of the present compounds (2) and (10) showed a pest death rate of 40% or more.

Test Example 4

A formulation of any one of the present compounds (1) to (10) obtained according to Formulation Example 15 was diluted with water so that the active ingredient concentration was 500 ppm to obtain a test solution.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 2 male imagoes of Blattalla germanica were released and the cup was sealed with a lid. After 6 days, the number of surviving Blattalla germanica was examined and the death rate of the pest was calculated.

As a result, the treatments with any one of the present compounds (1), (2), (3), (4) and (5) showed a pest death rate of 100%. The treatment with the present compound (9) showed a pest death rate of 50% or more.

Test Example 5

A formulation of any one of the present compounds (1) to (10) obtained according to Formulation Example 15 was diluted with water so that the active ingredient concentration was 500 ppm to obtain a test solution.

To 100 mL of ion-exchanged water, 0.7 ml of the test solution was added (active ingredient concentration: 3.5 ppm). Into the solution, 20 last-instar larvae of Culex pipiens pallens were released. One day after, the number of surviving Culex pipiens pallens was examined and the death rate of the pest was calculated.

As a result, the treatments with any one of the present compounds (1), (3), (4), (5), (6) and (10) showed a pest death rate of 95% or more. The treatments with any one of the present compounds (6), (7) and (9) showed a pest death rate of 10% or more.

Test Example 6

In this Test Example, as a comparative compound, a compound disclosed in JP-A 2005-179321 (Compound No. 37 in Table 2) and represented by the formula:

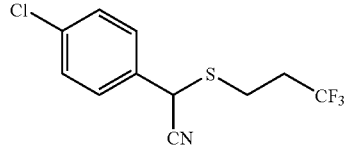

(hereinafter, referred to as the comparative compound (1)) was used.

Each formulation of the present compound (6) and the comparative compound (1) was obtained according to Formulation Example 15. The formulation was diluted so that the active ingredient concentration was 175 ppm to obtain a test solution.

At the same time, 50 g of culture soil, Bonsol No. 2 (manufactured by Sumitomo Chemical Co., Ltd.) was put into a polyethylene cup, and 10 to 15 seeds of rice were planted therein. The rice plants were grown until the second foliage leaf was developed, and then cut so as to have the same height of 5 cm. The test solution was sprayed on the rice plants in an amount of 20 ml/cup. After the test solution sprayed on the rice plants was dried, the rice plants were placed in a plastic cup for the purpose of preventing test worms from escaping. Thirty first-instar larvae of brown rice planthopper were released into the cup, and the cup was sealed with a lid. Then the cup was placed in a greenhouse at 25° C. for 6 days. Then, the number of parasitic brown rice planthoppers on the rice plants was examined.

As a result, on the plants treated with the present compound (6), the number of the parasitic pests was 3 or smaller. On the plants treated with the comparative compound (1), the number of the parasitic pests was 21 or larger.

Industrial Applicability

The compound of the present invention has an excellent controlling effect on arthropod pests, and thus it is useful as an active ingredient for a pesticidal composition.

The invention claimed is:

1. A fluorine-containing organosulfur compound represented by the formula (I):

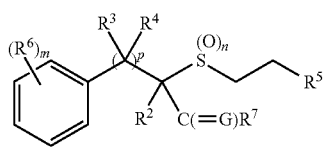

wherein G represents an oxygen atom or a sulfur atom;
$R^2$ represents a halogen atom, a hydrogen atom, or a C1-C4 chain hydrocarbon group which is optionally substituted with a halogen atom;
$R^3$ and $R^4$ independently represent a C1-C4 chain hydrocarbon group or a hydrogen atom;
$R^5$ represents a fluorine atom, or a C1-C5 haloalkyl group containing at least one fluorine atom;
$R^6$ represents a halogen atom, a cyano group, a nitro group, or a $-(G^1)_q-R^8$ group;
$R^7$ represents an amino group, a C1-C4 alkylamino group which is optionally substituted with a halogen atom, a di(C1-C4 alkyl)amino group which is optionally substituted with a halogen atom, or a C2-C5 cyclic amino group;
$R^8$ represents a C1-C4 chain hydrocarbon group which is optionally substituted with a halogen atom;
m represents an integer of 0 to 5, provided that $R^6$'s are optionally the same as or different from each other when m is from 2 to 5;
n represents an integer of 0 to 2;
p represents 0 or 1;
q represents 0 or 1; and
$G^1$ represents an oxygen atom, a sulfur atom, a —SO— group, or —SO$_2$— group.

2. The fluorine-containing organosulfur compound according to claim 1, wherein p is 0.

3. The fluorine-containing organosulfur compound according to claim 1 or 2, wherein G is an oxygen atom.

4. The fluorine-containing organosulfur compound according to claim 1 or 2, wherein G is an oxygen atom and $R^7$ is an amino group.

5. The fluorine-containing organosulfur compound according to claim 1, wherein $R^2$ is a halogen atom.

6. The fluorine-containing organosulfur compound according to claim 1, wherein n is 2.

7. A pesticidal composition comprising the fluorine-containing organosulfur compound according to claim 1 as an active ingredient.

8. A method of controlling an arthropod pest which comprises applying an effective amount of the fluorine-containing organosulfur compound according to claim 1 to the arthropod pest or a place where the arthropod pest inhabits.

* * * * *